United States Patent
Kerkvliet et al.

(10) Patent No.: US 10,308,649 B2
(45) Date of Patent: Jun. 4, 2019

(54) COMPOUNDS AND METHODS TO SUPPRESS AUTOIMMUNE RESPONSE

(71) Applicant: Oregon State University, Corvallis, OR (US)

(72) Inventors: Nancy I. Kerkvliet, Corvallis, OR (US); Siva Kumar Kolluri, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/522,241

(22) PCT Filed: Oct. 28, 2015

(86) PCT No.: PCT/US2015/057873
§ 371 (c)(1),
(2) Date: Apr. 26, 2017

(87) PCT Pub. No.: WO2016/069780
PCT Pub. Date: May 6, 2016

(65) Prior Publication Data
US 2018/0030048 A1     Feb. 1, 2018

Related U.S. Application Data

(60) Provisional application No. 62/069,723, filed on Oct. 28, 2014.

(51) Int. Cl.
*A61K 31/407* (2006.01)
*C07D 471/04* (2006.01)

(52) U.S. Cl.
CPC .......... *C07D 471/04* (2013.01); *A61K 31/407* (2013.01)

(58) Field of Classification Search
CPC ..................... A61K 31/407; C07D 471/04
See application file for complete search history.

(56) References Cited

U.S. PATENT DOCUMENTS

2010/0324109 A1   12/2010   Saurat et al.

FOREIGN PATENT DOCUMENTS

WO         2013/033657 A2       3/2013

OTHER PUBLICATIONS

International Preliminary Report on Patentability dated May 11, 2017, issued in corresponding International Application No. PCT/US2015/057873, filed Oct. 28, 2015, 5 pages.
International Search Report and Written Opinion dated Jan. 21, 2016, issued in corresponding International Application No. PCT/US2015/057873, filed Oct. 28, 2015, 9 pages.
Kerkvliet, N.I., et al., "Activation of Aryl Hydrocarbon Receptor by TCDD Prevents Diabetes in NOD Mice and Increases Foxp3+ T Cells in Pancreatic Lymph Nodes," Immunotherapy 1(4):539-547, Jul. 2009. (Author Manuscript provided, PMCID: PMC2823486, available in PMC May 1, 2010, 14 pages.)
Punj, S., et al., "Benzimidazoisoquinolines: A New Class of Rapidly Metabolized Aryl Hydrocarbon Receptor (AhR) Ligands That Induce AhR-Dependent Tregs and Prevent Murine Graft-Versus-Host Disease," PLOS One 9(2):e88726, Feb. 2014, pp. 1-10.
Extended European Search Report dated May 4, 2018, issued in corresponding European Application No. 15855322.2, filed Oct. 28, 2015, 6 pages.
Hanieh, H., "Toward Understanding the Role of Aryl Hydrocarbon Receptor in the Immune System: Current Progress and Future Trends," BioMed Research International, vol. 2014, Article ID 520763, pp. 1-14.
Reply to Communication pursuant to Rules 70(2) and 70a(2) EPC, dated Nov. 28, 2018, in corresponding European Application No. 158553222, filed Oct. 28, 2015, 8 pages.

*Primary Examiner* — Zohreh A Fay
(74) *Attorney, Agent, or Firm* — Christensen O'Connor Johnson Kindness PLLC

(57) ABSTRACT

A composition and method for treating autoimmune disease includes administering an effective amount of an aryl hydrocarbon receptor (AhR) ligand. The AhR ligand includes 11-Cl-BBQ, 10-Cl-BBQ, an analog of 11-Cl-BBQ, or combination thereof. The AhR ligand is administered topically, orally, transdermally, intravenously, subcutaneously, or with a nanoparticle. The AhR ligand induces regulatory T cells (AhR-Tregs). AhR-Treg cells block the differentiation of cytotoxic T-lymphocytes (CTL). The AhR ligand activates AhR in CD4+ T cells to induce CD4+ AhR-Tregs that suppress the development of effector CTL, thereby suppressing the development of CTL that attack host cells in graft versus host disease (GVHD) or β-cells in the pancreas in diabetes mellitus type 1 (T1DM). The AhR ligand can also suppress development of CTL independently of Foxp3+ regulatory T cell induction. The AhR ligand can therefore be used to treat autoimmune diseases characterized by an absence of functional Foxp3+ regulatory T cell.

9 Claims, 50 Drawing Sheets

COMPOUNDS AND METHODS TO SUPPRESS AUTOIMMUNE RESPONSE

CLAIMS OF DOMESTIC PRIORITY

The present application is a national stage of International Application No. PCT/US2015/057873, filed Oct. 28, 2015, which claims the benefit of U.S. Provisional Application No. 62/069,723, filed Oct. 28, 2014, which applications are incorporated herein by reference.

FEDERALLY-SPONSORED RESEARCH OR DEVELOPMENT

The present invention was made with government support under 5R01ES016651 awarded by National Institutes of Health. The government has certain rights in the invention.

FIELD OF THE INVENTION

The present invention relates to methods and compositions for treating autoimmune diseases and, more particularly, to a method of altering T cell differentiation and function to suppress autoimmune destruction of healthy cells.

BACKGROUND OF THE INVENTION

Autoimmune disease is caused by a failure of the immune system to recognize the difference between healthy tissue and harmful substances in the body. The immune system attacks healthy tissue and causes damage that may affect one or more tissue type or organ. For example, type 1 diabetes (T1DM), also known as diabetes mellitus type 1, is an autoimmune disease in which cytotoxic T-lymphocytes (CTL) attack and destroy the insulin-producing beta cells (β-cells) in the pancreas. Current management of T1DM involves administration of insulin and various formulations of insulin. Currently, an estimated 80,000 children develop T1DM each year and approximately 3 million people have T1DM in the United States. Complications from T1DM include heart disease, stroke, kidney failure, foot ulcers, and diabetic retinopathy. In addition, insulin treatment can lead to low blood sugar, or hypoglycemia, which can result in coma and death. Another immune-mediated disease, graft versus host disease (GVHD), can occur after a tissue transplant or blood transfusion. GVHD develops when grafted donor cells recognize the recipient's cells as foreign and differentiate into CTL that attack a recipient's healthy cells. GVHD can cause a range of symptoms from mild to severe, including death.

Current immune-suppressing drug therapies for GVHD, T1DM, and other autoimmune disorders produce global immune suppression throughout the body in order to reduce the autoimmune activity of CTL. Such immune suppression results in undesirable side effects associated with general immune suppression including an increased risk of infection and certain cancers. Thus, conventional immunosuppressive treatments of autoimmune diseases fail to provide long-term remission without severe side effects.

Targeting T cells is a promising therapeutic strategy for the prevention or treatment of autoimmune diseases. The aryl hydrocarbon receptor (AhR) represents a potential drug target as a ligand-activated transcription factor that directly alters T cell differentiation without cytotoxicity. 2,3,7,8-tetrachlorodibenzo-p-dioxin (TCDD) is a potent AhR ligand. Studies with TCDD have shown that AhR signaling during the early stages of cluster of differentiation 4 positive (CD4+) T cell activation results in induction of CD4+ regulatory T cells (Treg cells or Tregs) and premature cessation of cluster of differentiation 8 positive (CD8+) effector CTL differentiation. Treating mice with TCDD has been shown to prevent or ameliorate several different types of autoimmune and allergic diseases supporting the therapeutic potential of the AhR pathway and AhR as a potential therapeutic target. However, TCDD has unfavorable pharmacological properties due to TCDD's high lipid solubility and resistance to metabolism, which leads to a TCDD half-life of approximately seven years in humans. Additionally, the notoriety of TCDD as an environmental toxicant is likely to limit TCDD's acceptance for pharmacologic uses.

SUMMARY OF THE INVENTION

A need exists for a non-toxic therapy to suppress an autoimmune response without inducing general immune suppression. Accordingly, in one embodiment, the present invention is a method of treating an autoimmune disease comprising the step of administering a therapeutically effective amount of an AhR ligand including 11-chloro-7H-benzimidazo[2,1-a]benzo[de]Iso-quinolin-7-one (11-Cl-BBQ) or an analog of 11-Cl-BBQ.

In another embodiment, the present invention is a method of treating an autoimmune disease comprising the step of administering a therapeutically effective amount of an AhR ligand.

In another embodiment, the present invention is a method of altering T cell differentiation comprising the step of administering a therapeutically effective amount of an aryl hydrocarbon receptor (AhR) ligand including 11-Cl-BBQ or an analog of 11-Cl-BBQ.

In another embodiment, the present invention is a method of altering T cell differentiation comprising the step of administering a therapeutically effective amount of an AhR ligand.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Targeting T cells is a promising therapeutic strategy for the prevention or treatment of autoimmune diseases. The AhR is a ligand-activated transcription factor that plays multiple roles in regulation of immune and inflammatory responses. AhR represents a target as a ligand-activated transcription factor that directly alters T cell differentiation without cytotoxicity. Activation of AhR has been implicated in the development of innate lymphoid cells in the gut, induction of tolerogenic dendritic cells, and modulation of several aspects of T cell differentiation, including the induction of regulatory T cells. For example, AhR-deficient mice are hyper-responsive to inflammatory stimuli, showing increased production of inflammatory cytokines and increased immunopathology, supporting an immunoregulatory role for the AhR. Treatment of mice with the potent AhR ligand TCDD has been shown to prevent or ameliorate several different types of autoimmune and allergic diseases supporting AhR as a therapeutic target.

The activation of AhR by an AhR ligand can alter T cell differentiation. AhR ligands activate the AhR in alloantigen-responsive T cells, which induces AhR-dependent Tregs. AhR-dependent Tregs are a phenotype identified during initial activation and expansion of the naïve allospecific CD4+ T cells and are characterized by high expression of cluster of differentiation 25 (CD25), cytotoxic T-lymphocyte-associated protein 4 (CTLA-4), and several other molecules associated with regulatory T cells, but not expression of transcription factor forkhead box P3 (Foxp3). AhR-induced Tregs (AhR-Tregs) showed potent suppression of naïve and allogeneic T cell proliferation in vitro. The induction of AhR-Tregs suppresses the development of effector CTL in vivo, thereby suppressing the development of CTL that attack host cells in GVHD or β-cells in the pancreas in T1DM. As shown herein, activation of AhR by an AhR ligand can also alter T cell differentiation and suppress effector CTL accumulation independently of Treg induction.

Figure 1A:
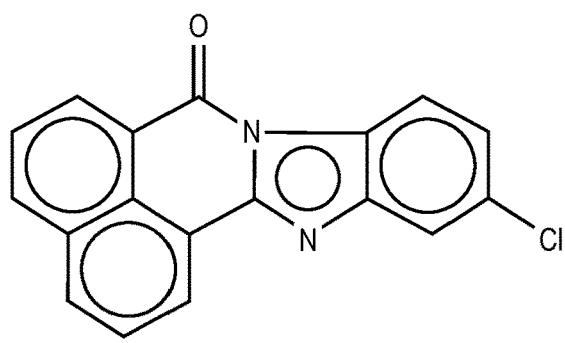
FIGS. 1a-1b illustrate the chemical structure of 11-Cl-BBQ and 10-Cl-BBQ.

A small-molecule screening was performed to identify high-affinity AhR ligands with a more favorable pharmacokinetic profile than the metabolism-resistant TCDD. FIG. 1a shows the chemical structure of 11-Cl-BBQ. 11-Cl-BBQ is a nontoxic AhR ligand with favorable pharmacologic properties and an in vivo serum half-life of approximately two hours. Like TCDD, 11-Cl-BBQ targets and activates AhR in CD4+ T cells.

Figure 1B:
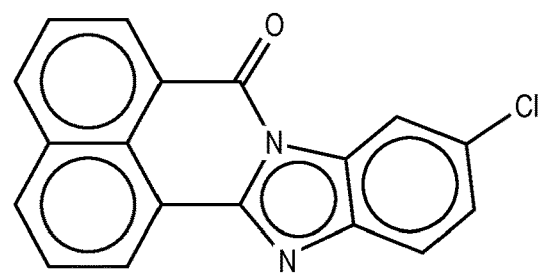

FIG. 1b shows the chemical structure 10-chloro-7H-benzimidazo[2,1-a]benzo[de]Iso-quinolin-7-one (10-Cl-BBQ). 10-Cl-BBQ is another AhR ligand that targets and activates AhR in CD4+ T cells, similar to TCDD and 11-Cl-BBQ. 10-Cl-BBQ also has favorable pharmacologic properties and an in vivo serum half-life of approximately two hours. 10-Cl-BBQ represents an analog of 11-Cl-BBQ. As used herein, the term "analog" refers to a chemical compound that is structurally similar to another, but differs slightly in composition (as in the replacement of one atom by an atom of a different element, or the replacement of an atom by a functional group, or the replacement of one functional group by another functional group). Thus, an analog is a compound that is similar or comparable in function and appearance, but not in structure or origin to the reference compound.

Figure 15A:
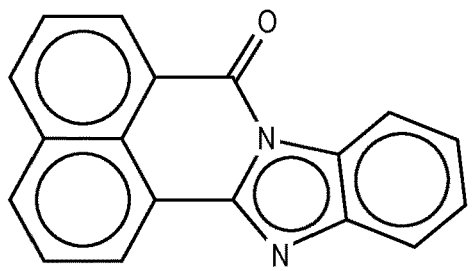
FIGS. 15a-15e illustrate the chemical structure of several analogs of 11-Cl-BBQ.

FIG. 15a shows the chemical structure of 7H-Benzimidazo[2,1-a]benzo[de]isoquinolin-7-one (BBQ). 10-Cl-BBQ represents a substituted BBQ molecule, i.e., a BBQ molecule having a chlorine (Cl) substitution on the 10 carbon (a 10-chloro substitution). 11-Cl-BBQ represents another substituted BBQ molecule, i.e., a BBQ molecule having a Cl substitution on the 11 carbon (an 11-chloro substitution). The basis of the present invention is that treatment of individuals having an autoimmune or other immune-mediated disease with 11-Cl-BBQ, 10-Cl-BBQ, an analog of 11-Cl-BBQ (e.g., an unsubstituted BBQ molecule or a BBQ molecule having a substitution other than or in addition to 11-chloro), or combinations thereof will alter T cell differentiation and suppress CTL production. For example, treatment during the early stages of T1DM with 11-Cl-BBQ, 10-Cl-BBQ, an 11-Cl-BBQ analog, or combination thereof will prevent the autoimmune destruction of pancreatic β-cells and consequently prevent the progression and development of T1DM into full-blown T1DM. Similarly, treatment of an individual after a tissue transplant with 11-Cl-BBQ, 10-Cl-BBQ, an 11-Cl-BBQ analog, or combination thereof will suppress GVHD.

FIGS. 2a-2e illustrate results of a NOD mouse model showing treatment with an AhR ligand compound (AHRL1) comprised of a mixture of approximately 60% 11-Cl-BBQ molecules and 40% 10-Cl-BBQ molecules suppresses islet infiltration by inflammatory CTL cells. NOD/LtJ mice were purchased from the Jackson Laboratory (Bar Harbor, Me.). The mice were bred and maintained under specific pathogen-free conditions at Oregon State University facilities. All experimental procedures using animals were approved by the Institutional Animal Care and Use Committee at Oregon State University.

The effective dose of AHRL1 was calculated empirically by determining what concentration of AHRL1 would induce a cytochrome P450 1A1 (CYP1A1) expression level equivalent to the CYP1A1 expression level produced by 25 micrograms per kilogram (µg/kg) TCDD, which is a therapeutically effect dose of TCDD in NOD mice. AHRL1 was dissolved in a 30% dimethyl sulfoxide (DMSO), 20% CREMAPHOR, 50% PECEOL solution and administered by oral gavage. CYP1A1 expression was measured by isolating ribonucleic acid (RNA) from mouse liver samples using RNEASY RNA purification spin columns (QIAGEN), and cDNA was synthesized using a REACTION READY first strand cDNA synthesis kit (SUPERARRAY). PCR reactions were performed on an ABI PRISM 7500 Real-Time PCR system (APPLIED BIOSYSTEMS) using SYBR Green/ROX Master Mix (SA Biosciences). CYP1A1 levels were normalized to beta-actin (β-actin) using primers from SA Biosciences.

Figure 2A:
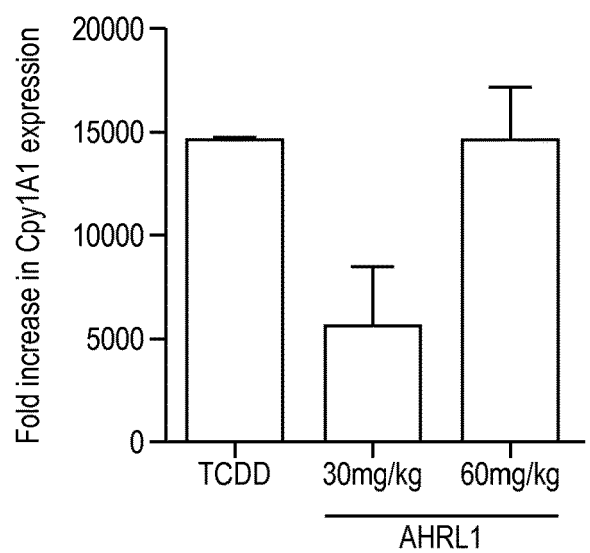
FIGS. 2a-2e illustrate treatment with AHRL1 suppresses islet infiltration in non-obese diabetic (NOD) mice.

FIG. 2a shows oral treatment with 60 milligram per kilogram (mg/kg) AHRL1 induced an expression of CYP1A1 commensurate with the therapeutic dose (25 μg/kg) of TCDD in NOD mice. Various dosing regimens, e.g., administering alternating 60 mg/kg and 30 mg/kg doses daily, administering 60 mg/kg every other day, administering 60 mg/kg 3-times per week, were tested to determine an optimal dosing schedule that would minimize the number of doses of AHRL1 that needed to be administered while maintaining activation of AhR. AhR activation was confirmed by measuring CYP1A1 expression. 60 mg/kg treatment with AHRL1 3-times per week was found to be an optimal dosing schedule.

Figure 2B:
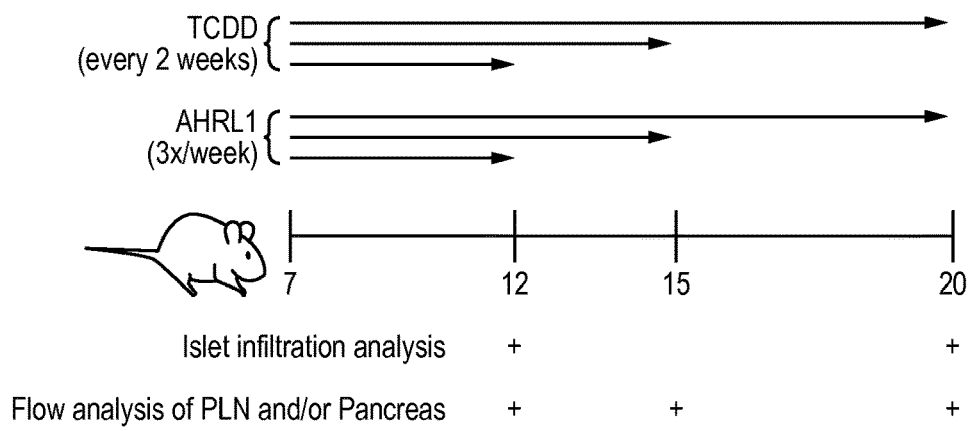

FIG. 2b illustrates details of the NOD mouse model used to test therapeutic effects of treatment with AHRL1. Starting at 7 weeks of age, NOD mice were treated with AHRL1, TCDD, or vehicle. 60 mg/kg of AHRL1 was administered 3-times per week by oral gavage. The carrier for AHRL1 was a 30% DMSO, 20% CREMAPHOR, 50% PECEOL solution. TCDD treated mice were used as a positive control group. An initial loading dose of 50 μg/kg of TCDD was administered by oral gavage, followed by 15 μg/kg every other week. The vehicle administered was the carrier for the AHRL1 compound, i.e., a 30% DMSO, 20% CREMAPHOR, 50% PECEOL solution. Blood glucose was measured weekly. At 12 weeks of age and 20 weeks of age, the mice were sacrificed and the pancreases of the mice were excised, sectioned, and stained with hematoxylin and eosin for analysis of islet infiltration by inflammatory CTL cells. Islet infiltration was scored on sequential hematoxylin and eosin stained pancreas sections separated by 200 micrometers (μm). Islets were scored as no infiltration, less than 50% (<50%) infiltration, or greater than or equal to 50% (≥50%) infiltration. For statistical comparisons of degree of islet infiltration between groups, chi-squared analyses were performed. A sample size of n=7-9 mice per group was used. A single asterisk (*) signifies a p≤0.05; a double asterisk () signifies a p≤0.01; a triple asterisk (*) signifies a p≤0.001.

The leukocyte composition of the pancreas and draining lymph nodes was analyzed at 12, 15, and 20 weeks of age using flow cytometry. Mice were sacrificed at 12, 15, and 20 weeks of age, draining lymph nodes and pancreata were excised, and single cell suspensions were prepared for analysis with flow cytometry. Fc receptors were blocked with rat immunoglobulin G (IgG) acquired from Jackson ImmunoResearch. The cells were stained with the following antibodies: CD4 (RM4, eBioscience), CD8 (53-6.7, eBioscience), CD19 (1D3, eBioscience), CD45 (30-F11, BD Biosciences), Foxp3 (FJK-16s, eBioscience), Nrp1 (3DS304M, eBioscience), CD25 (PC61.5, eBioscience), RORγt (AFKJS-9, eBioscience). For intracellular staining, cells were fixed and permeabilized using a Foxp3 Fixation/Permeabilization buffer acquired from eBioscience (San Diego, Calif.). Data were acquired using a FC-500 flow cytometer (BECKMAN COULTER) and compensated and analyzed using FLOWJO software. Fluorescence minus one (FMO) controls were used for setting gates for analysis.

Figure 2C:
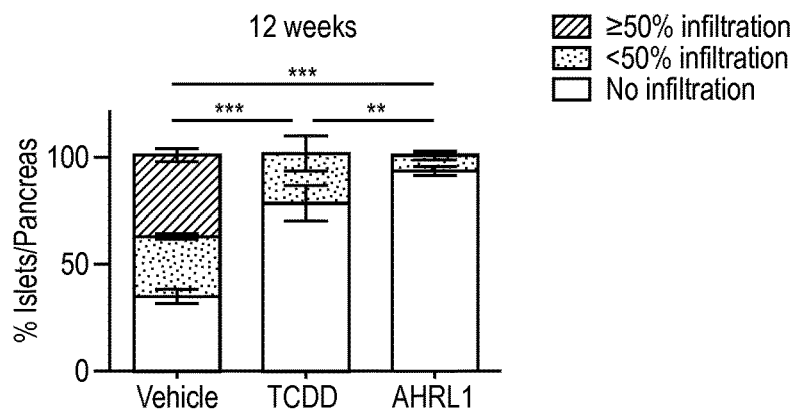
Figure 2D:
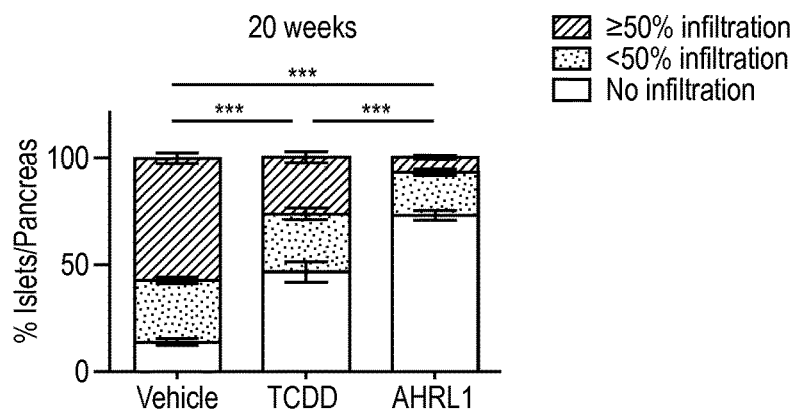
Figure 2E:
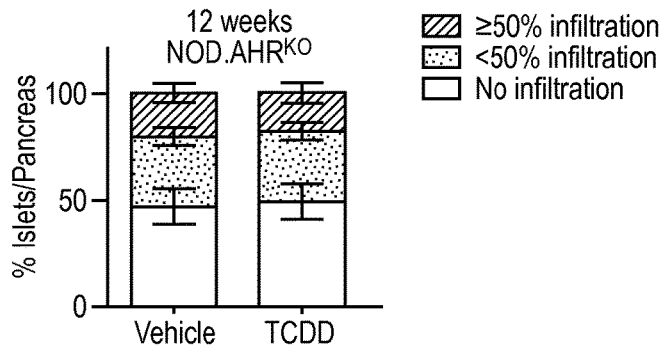

FIGS. 2c-2e illustrate treatment with AHRL1 prevents islet infiltration by inflammatory CTL cells at both early (12 weeks of age) and later (20 weeks of age) stages of disease progression.

FIG. 2c compares islet infiltration by inflammatory CTL cells in AHRL1 treated, TCDD treated, and vehicle treated mice at 12 weeks of age. FIG. 2c shows at 12 weeks of age, 65±3.4% of islets in the pancreas of vehicle treated mice were infiltrated with inflammatory CTL cells with 27.9±1.2% of the infiltrated islets having less than 50% islet infiltration and 37.5±3.1% of the infiltrated islets having greater than or equal to 50% islet infiltration. FIG. 2c further shows at 12 weeks of age, 92±2.0% of islets in the pancreas of AHRL1 treated mice were free from infiltration with the remaining 8% of the islets showing less than 50% infiltration. FIG. 2c also shows that mice treated with AHRL1 had a larger percentage of islets free from infiltration than mice treated with TCDD, illustrating that at the doses used, treatment with AHRL1 was more effective at preventing islet infiltration than TCDD.

FIG. 2d compares islet filtration by inflammatory CTL cells in AHRL1 treated, TCDD treated, and vehicle treated mice at 20 weeks of age. FIG. 2d shows at 20 weeks of age, vehicle treated mice had 85.6% of islets in the pancreas infiltrated with inflammatory CTL cells with 28.8±4.5% of the infiltrated islets having less than 50% infiltration and 56.8±7.8% of the infiltrated islets having greater than or equal to 50% infiltration. FIG. 2d further shows at 20 weeks of age, AHRL1 treated mice had 73.1±6.2% of islets free from infiltration. FIG. 2d also shows that mice treated with AHRL1 had a greater percentage of islets free from infiltration than mice treated with TCDD. The increased suppression of islet infiltration in AHRL1 treated mice indicates AHRL1 is more effective at preventing islet infiltration than TCDD.

The ability of AHRL1 to activate AhR and prevent or decrease islets infiltration by CTL indicates treatment with AHRL1, 11-Cl-BBQ, 10-Cl-BBQ, an 11-Cl-BBQ analog, or combinations thereof will be effective in suppressing pancreatic insulitis, the pathogenic mechanism underlying the development of T1DM.

FIG. 2e compares islet infiltration at 12 weeks of age in non-obese diabetic AhR deficient mice (NOD.AhR$^{-/-}$ mice) treated with AHRL1 to NOD.AhR$^{-/-}$ mice treated with vehicle. The NOD.AhR$^{-/-}$ mice were generated by backcrossing B6.129-AHR$^{tm1Bra}$/J onto the NOD/LtJ background for 13 generations. Starting at 7 weeks of age, NOD.AhR$^{-/-}$ mice were treated with AHRL1 or vehicle. 60 mg/kg AHRL1 was administered 3-times per week by oral gavage. The vehicle administered was the carrier for the AHRL1 compound. The carrier for the AHRL1 compound included a 30% DMSO, 20% CREMAPHOR, and 50% PECEOL solution. At 12 weeks of age, the NOD.AhR$^{-/-}$ mice were sacrificed, and the pancreases were excised, sectioned, and stained with hematoxylin and eosin for analysis of islet infiltration by inflammatory CTL cells. Islet infiltration was scored on sequential hematoxylin and eosin stained pancreas sections separated by 200 μm. Islets were scored as no infiltration, less than 50% infiltration, or greater than or equal to 50% infiltration. For statistical comparisons of degree of islet infiltration between groups, chi-squared analyses were performed. A sample size of n=7-9 mice per group was used. A single asterisk (*) signifies p≤0.05; a double asterisk () signifies p≤0.01; a triple asterisk (*) signifies p≤0.001.

FIG. 2e shows the percentage of total islets in the pancreas infiltrated, the percentage of islets infiltrated <50%, and the percentage of islets infiltrated ≤50% in AHRL1 treated NOD.AhR$^{-/-}$ mice were commensurate to vehicle treated NOD.AhR$^{-/-}$ mice. FIG. 2e illustrates treatment with AHRL1 did not affect islet infiltration in AhR-deficient mice as compared to vehicle treated AhR-deficient mice. FIG. 2e further shows a smaller percentage of islets were free from infiltration in AHRL1 treated NOD.AhR$^{-/-}$ as compared to the non-AhR-deficient mice (i.e., wild type NOD mice) treated with AHRL1 (FIG. 2c). The results illustrated in FIGS. 2c and 2e demonstrate AhR expression is required for AHRL1 to produce a therapeutic effect on insulitis.

Since the extent of islet infiltration is directly linked to development of elevated blood glucose and overt diabetes, islet infiltration provides a reliable biomarker for demonstrating the therapeutic efficacy of treatment with AHRL1. The strong suppression of islet infiltration in AHRL1 treated mice demonstrates the therapeutic potential of AHRL1, 11-Cl-BBQ, 10-Cl-BBQ, an 11-Cl-BBQ analog, or combination thereof to activate AhR and treat and/or prevent T1DM.

The therapeutic potential of AHRL1, 11-Cl-BBQ, 10-Cl-BBQ, an 11-Cl-BBQ analog, or combinations thereof is further demonstrated by the absence of clinical signs of toxicity associated with prolonged treatment with AHRL1. The results listed in Table 1 illustrate an absence of clinical signs of toxicity after prolonged treatment with AHRL1. Table 1 lists the results of a clinical chemistry profile from a toxicology screen of the AHRL1 treated, TCDD treated, and vehicle treated mice. The clinical chemistry panel includes tests for substances in the blood that have biological functions, metabolites or waste products, and substances that indicate cell damage or disease. The concentrations of the substances listed in Table 1 were measured at 20 weeks of age. The concentrations are reported as milligrams per deciliter (mg/dl), grams per deciliter (g/dl), units per liter (U/L), or milli equivalents per liter (mEq/L).

TABLE 1

| Substance Measured | Vehicle Treated Mice | TCDD Treated Mice | AHRL1 treated Mice |
| --- | --- | --- | --- |
| Blood Urine Nitrogen (BUN) (mg/dl) | 20.5 ± 2.6 | 20.0 ± 2.7 | 18.6 ± 7.3 |
| Creatinine (mg/dl) | 0.3 ± 0.1 | 0.3 ± 0.1 | 0.2 ± 0.1 |
| Cholesterol (mg/dl) | 96.4 ± 12.3 | 91.9 ± 5.1 | 94.9 ± 10.4 |
| Total Protein (g/dl) | 5.5 ± 0.5 | 5.6 ± 0.2 | 5.7 ± 0.3 |
| Albumin (g/dl) | 3.5 ± 0.1 | 3.4 ± 0.1 | 3.5 ± 0.3 |
| Bilirubin, Total (mg/dl) | 0.21 ± 0.04 | 0.43 ± 0.64 | 0.16 ± 0.05* |
| Creatinine Kinase (CK) (U/L) | 423.0 ± 396.3 | 398.3 ± 248.7 | 445.3 ± 241.0 |
| Alkaline Phosphatase (U/L) | 77.6 ± 18.9 | 80.0 ± 14.7 | 72.9 ± 17.4 |
| Gamma-glutamyl transferase (GGT) (U/L) | 0.0 ± 0.0 | 0.0 ± 0.0 | 0.0 ± 0.0 |
| Alanine Aminotransferase (ALT) (U/L) | 22.3 ± 6.2 | 24.0 ± 2.5 | 28.0 ± 4.9 |
| Sodium (mEq/L) | 153.1 ± 2.4 | 151.9 ± 2.4 | 154.6 ± 1.4 |
| Potassium (mEq/L) | 9.9 ± 0.2 | 9.7 ± 0.4 | 9.8 ± 0.6 |
| Chloride (mEq/L) | 108.9 ± 2.5 | 109.5 ± 1.7 | 110.8 ± 2.1 |
| Calcium (mg/dl) | 11.0 ± 0.4 | 10.8 ± 0.4 | 11.2 ± 0.3 |
| Phosphorous (mg/dl) | 8.3 ± 1.0 | 8.2 ± 1.2 | 8.1 ± 3.4 |
| Bicarbonate (tCO2) (mEq/L) | 18.6 ± 2.9 | 18.6 ± 1.4 | 16.9 ± 2.7 |
| Anion Gap (mEq/L) | 36.5 ± 2.4 | 34.0 ± 1.2* | 37.9 ± 3.0 |

Figure 18A:
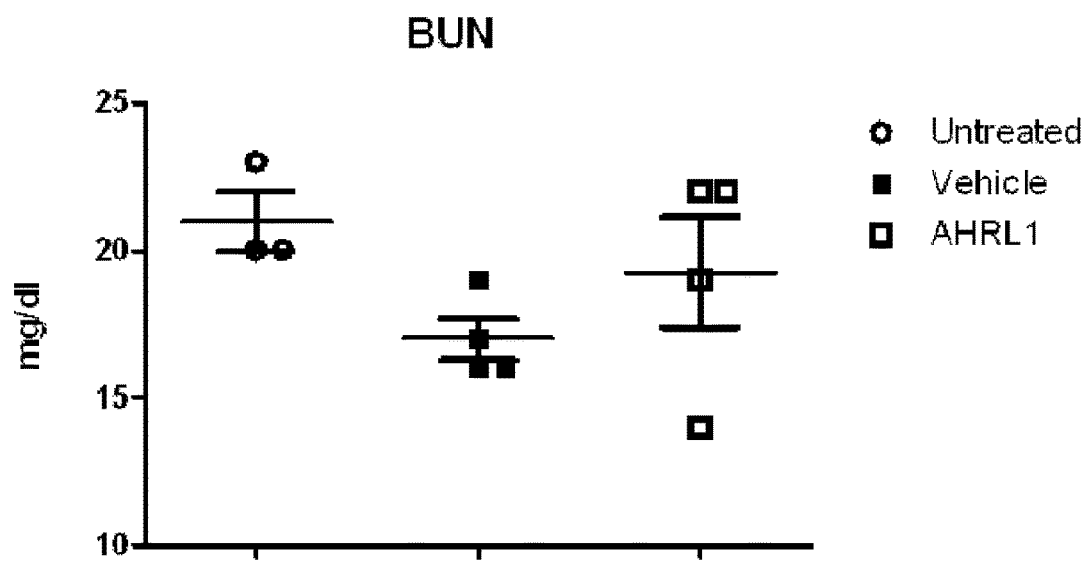
FIGS. 18a-18r illustrate the clinical chemistry profile from a toxicology screen for the tested NOD mice.
Figure 18B:
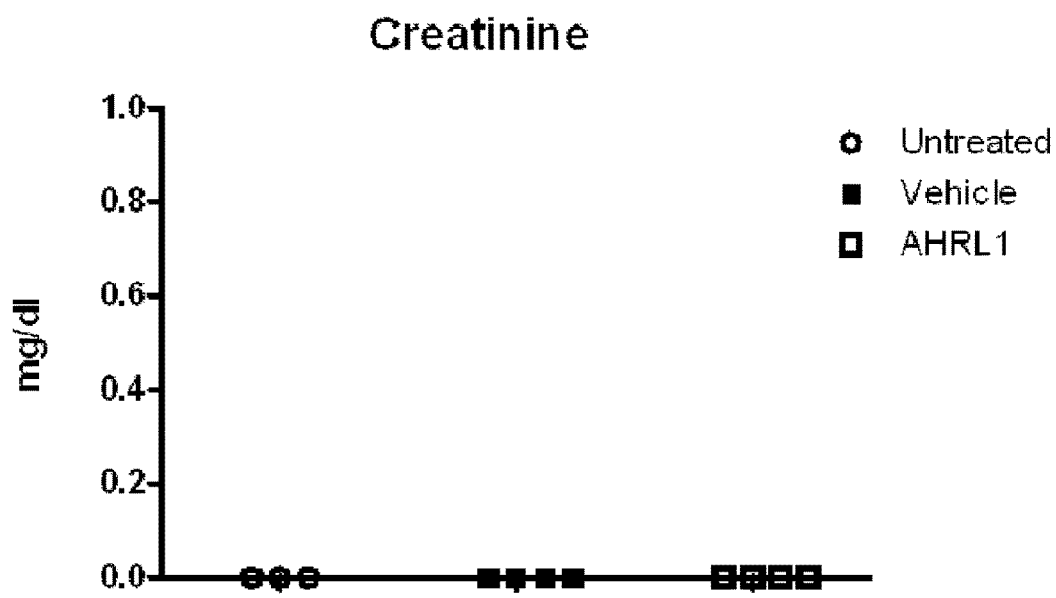
Figure 18C:
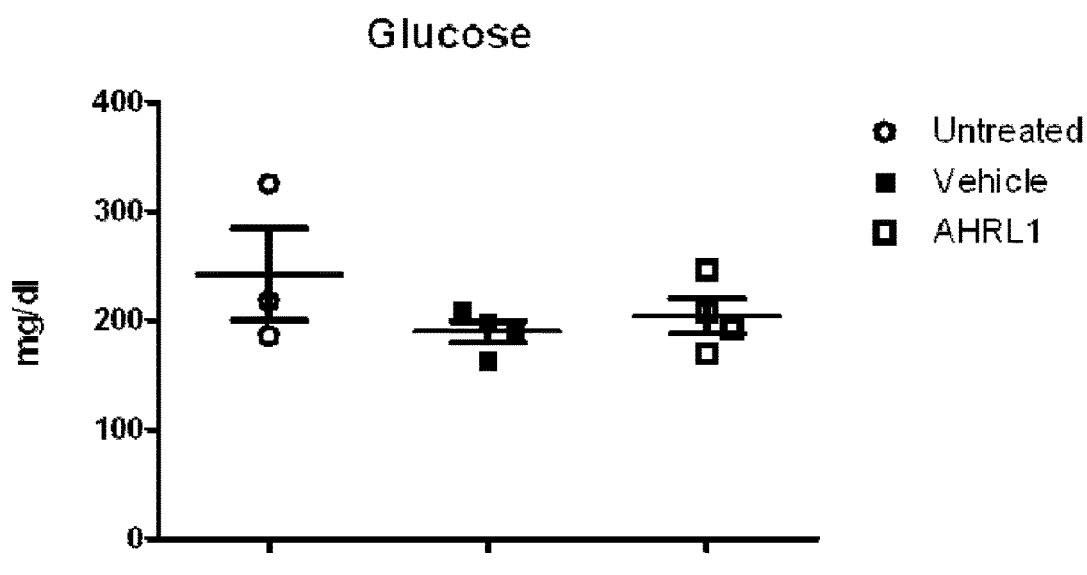
Figure 18D:
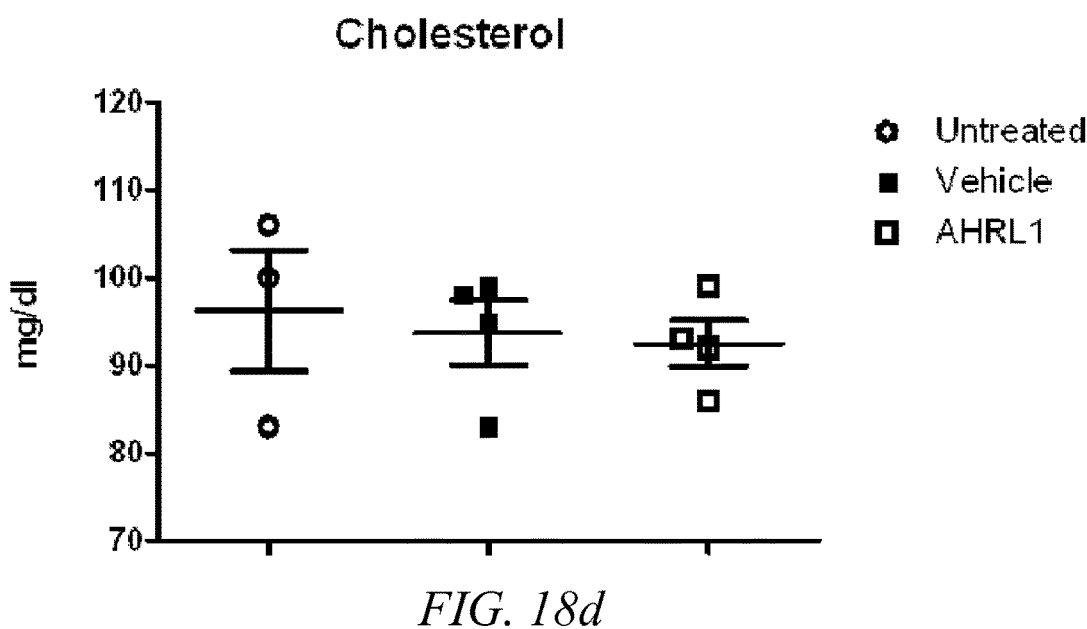
Figure 18E:
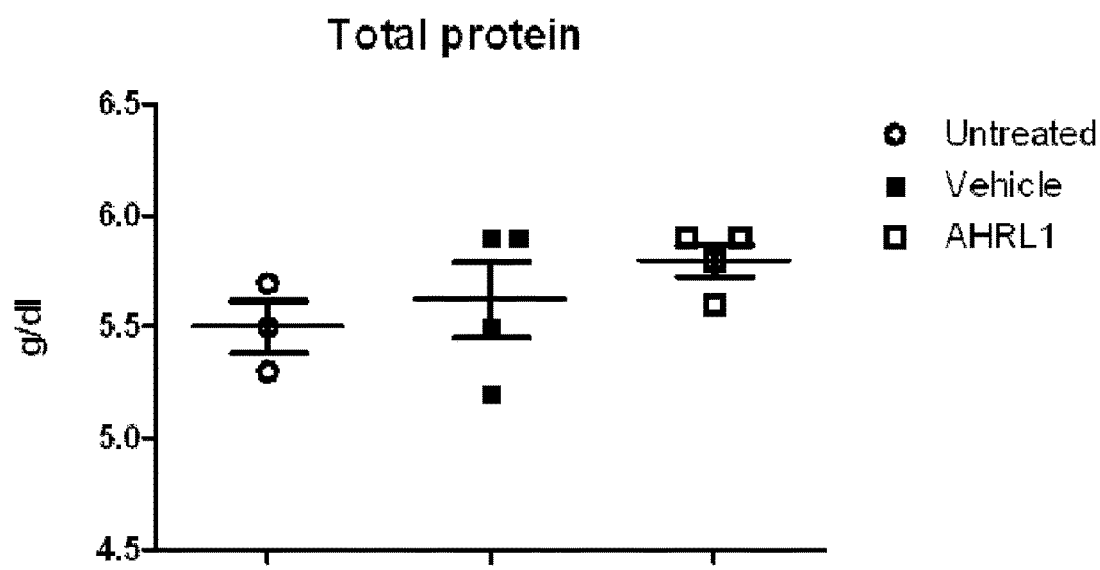
Figure 18F:
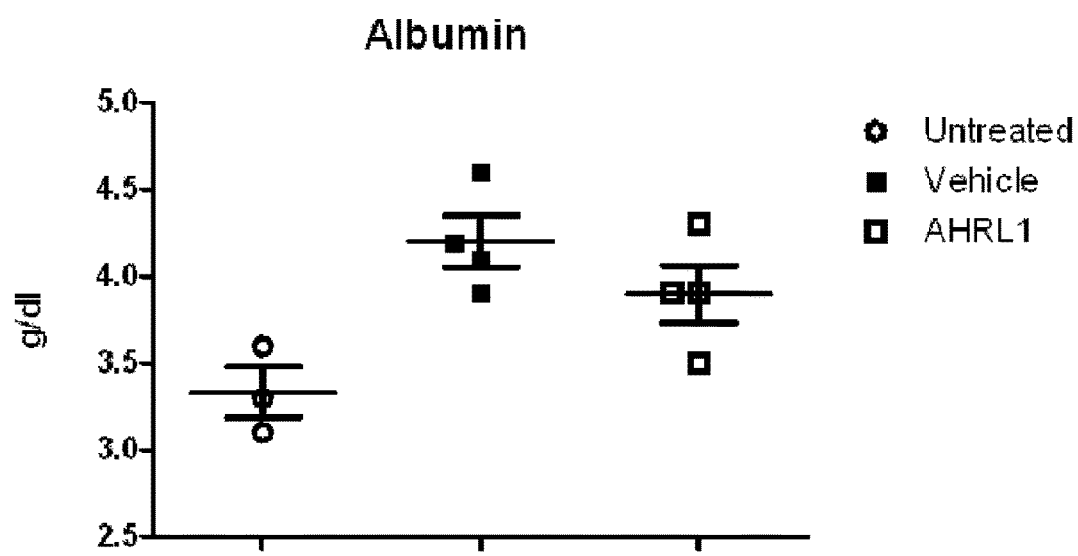
Figure 18G:
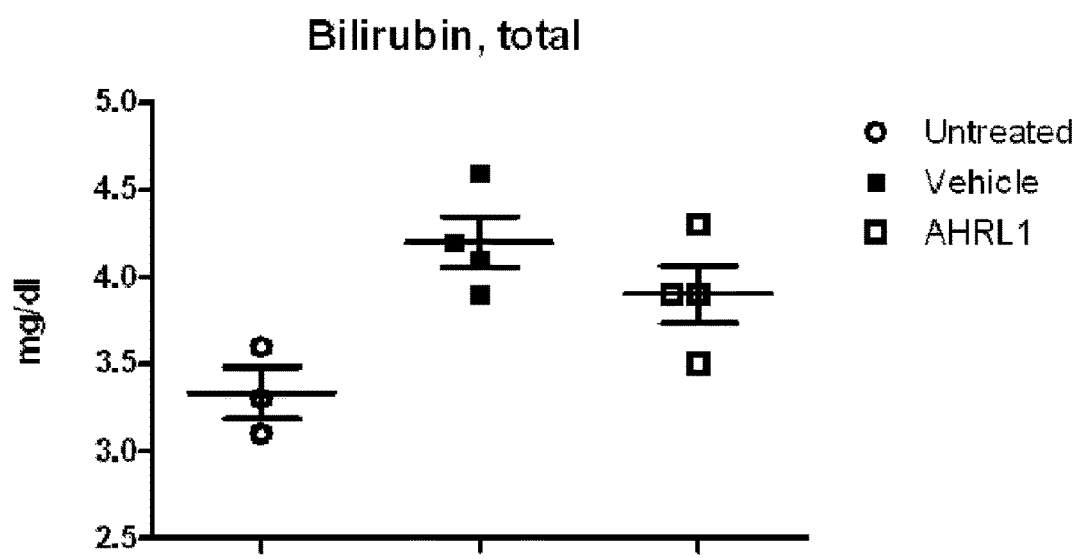
Figure 18H:
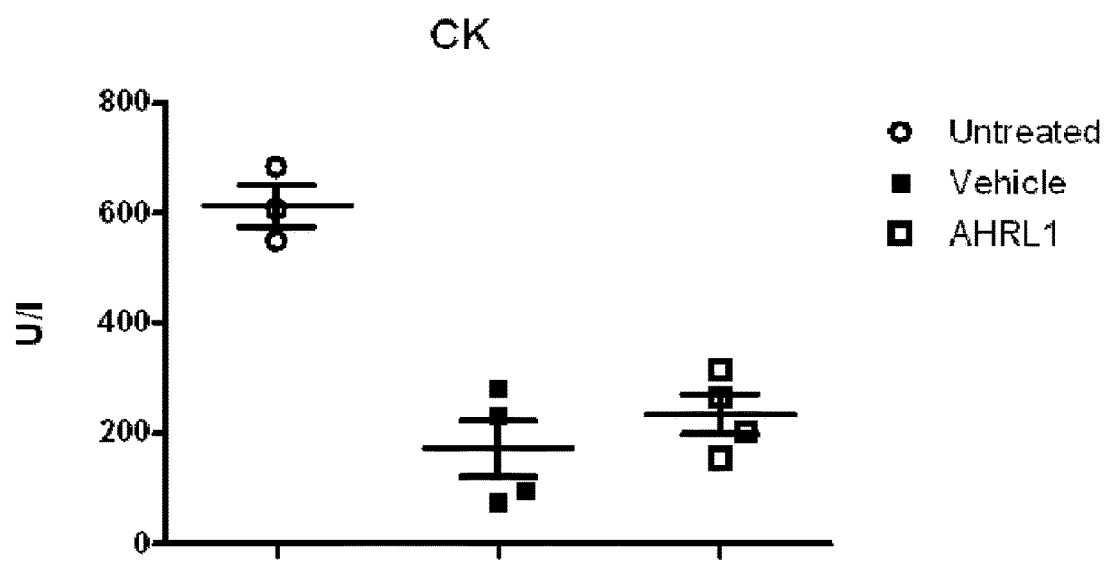
Figure 18I:
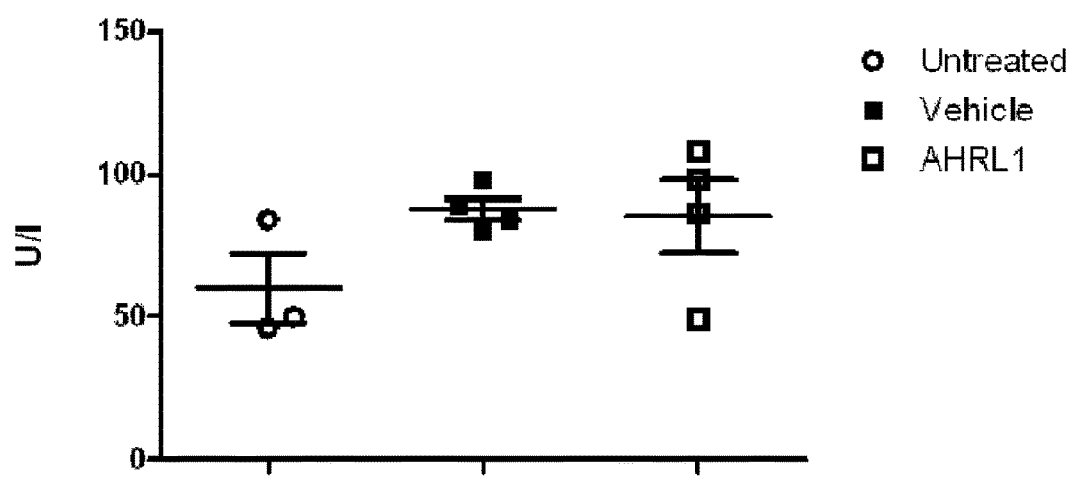
Figure 18J:
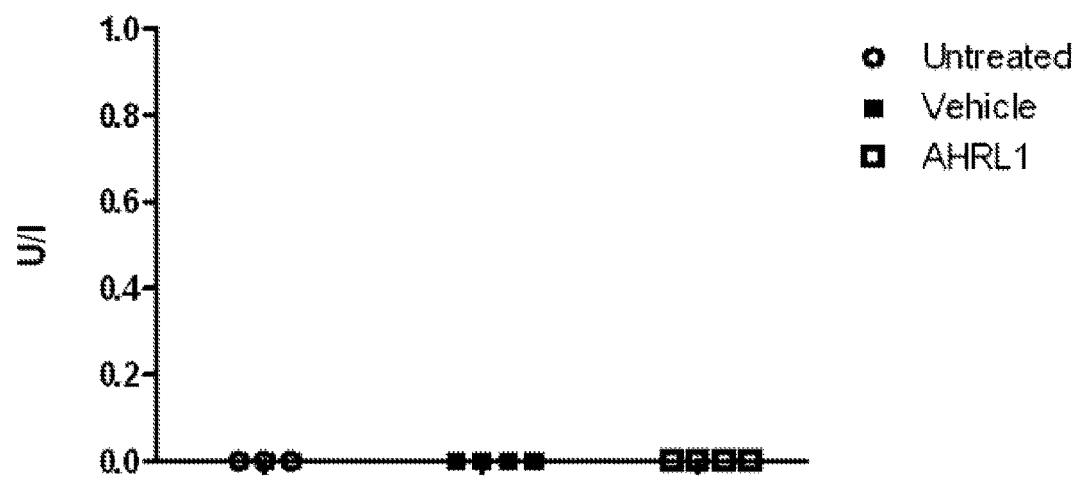
Figure 18K:
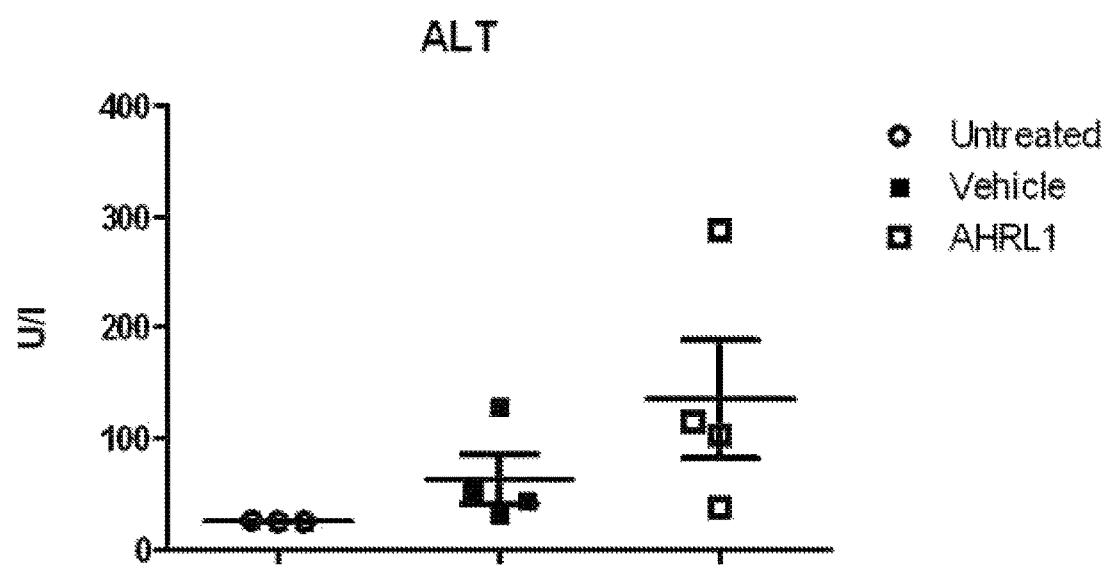
Figure 18L:
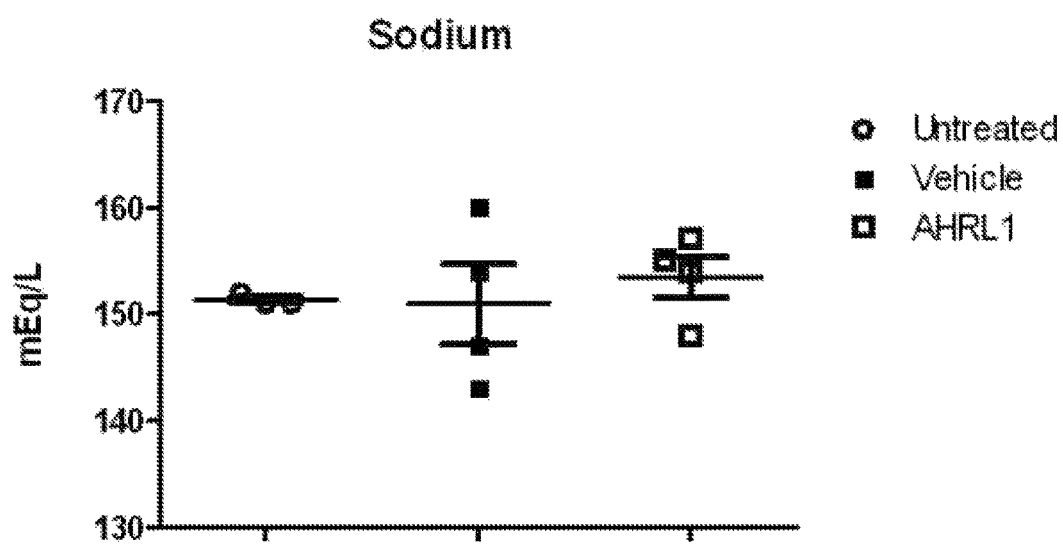
Figure 18M:
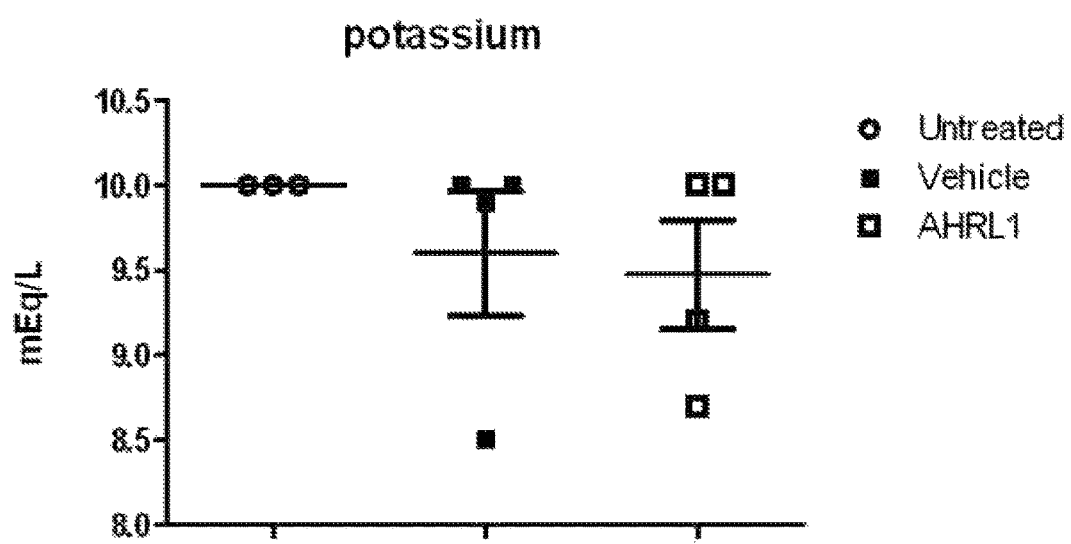
Figure 18N:
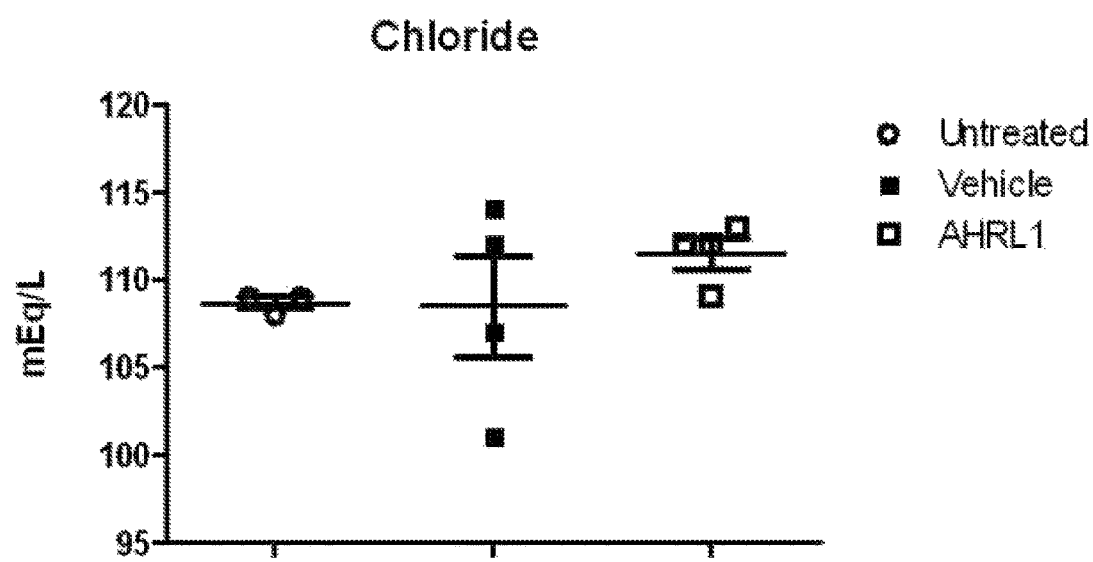
Figure 18O:
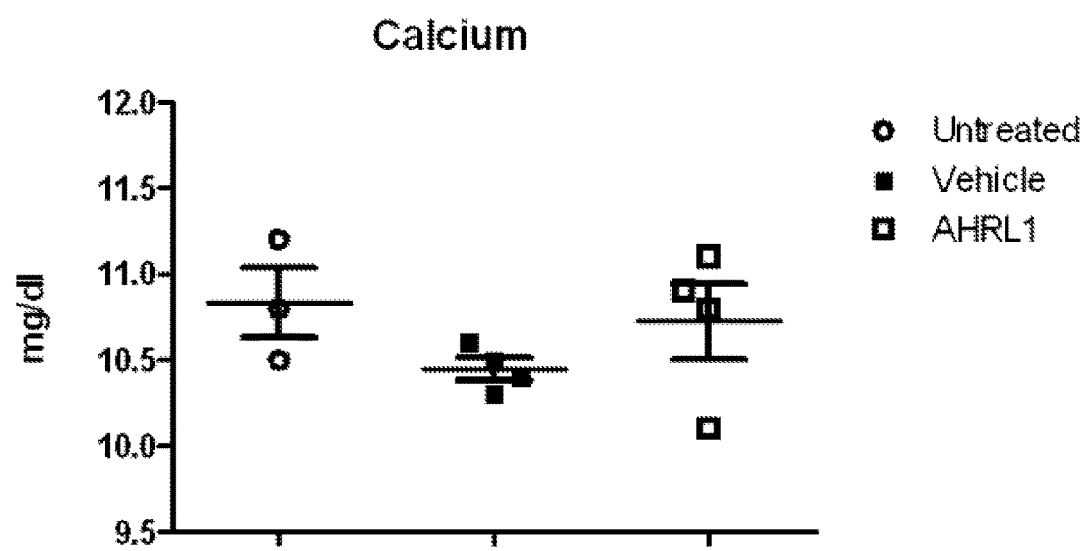
Figure 18P:
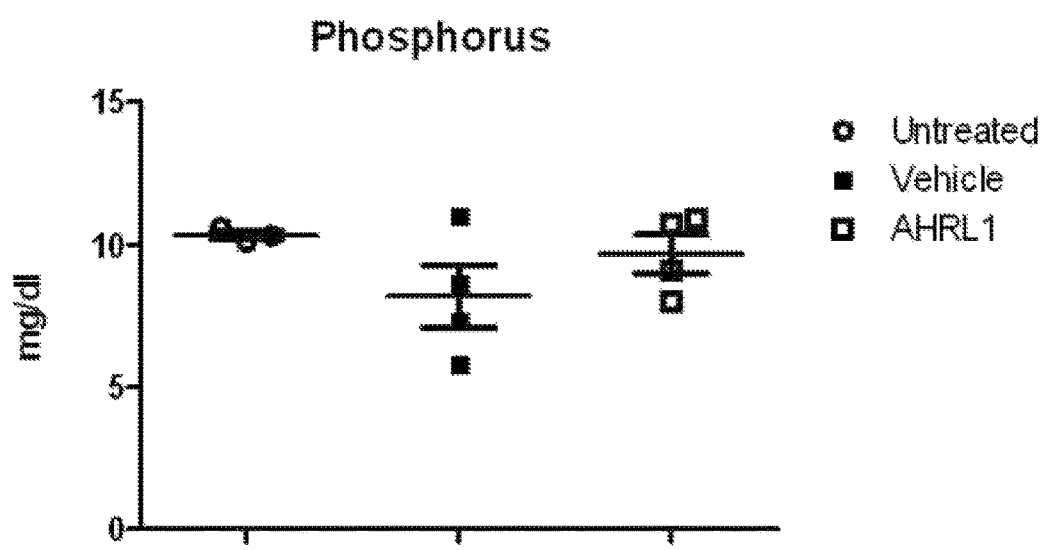
Figure 18Q:
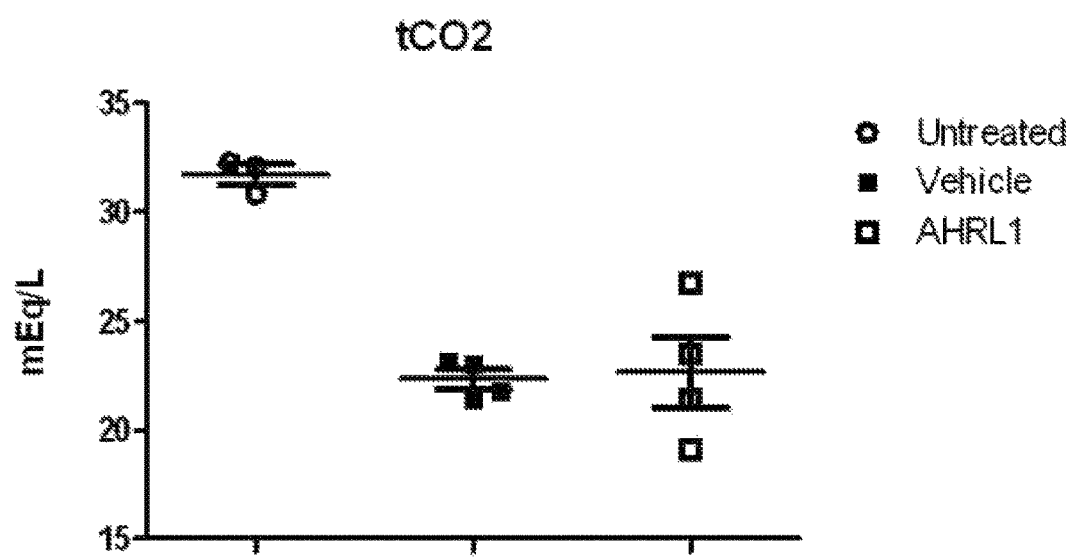
Figure 18R:
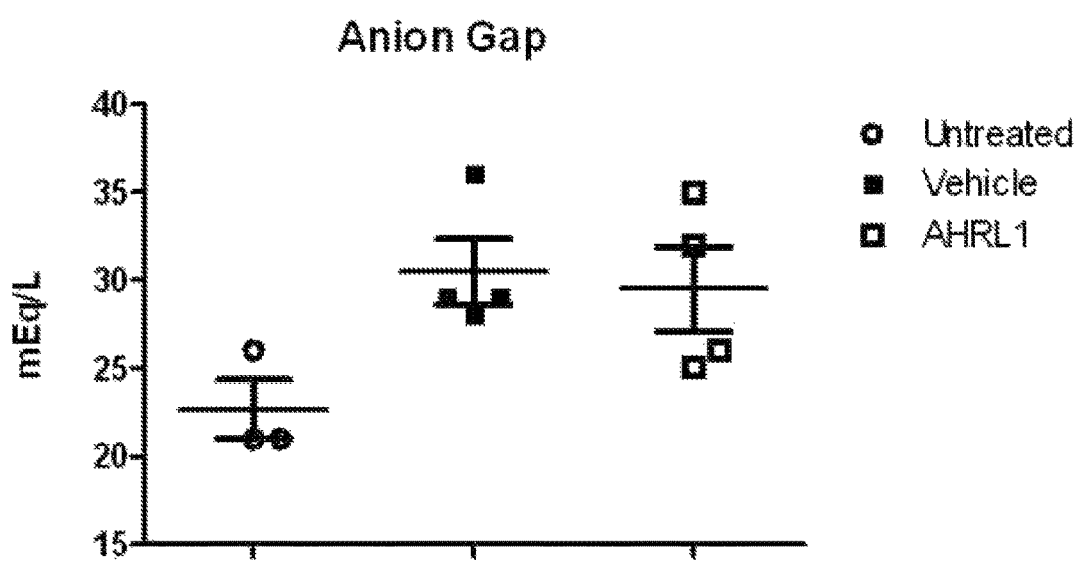

The commensurate substance concentrations in vehicle treated mice as compared to AHRL1 treated mice indicate treatment with AHRL1 does not produce toxicity. The consistency in the concentrations of the substances listed in Table 1 after chronic treatment with AHRL1 supports the potential use of AHRL1, 11-Cl-BBQ, 10-Cl-BBQ, an 11-Cl-BBQ analog, or combination thereof as a non-toxic therapeutic for treatment of autoimmune disease. FIGS. 18a-18r further illustrate an absence of clinical signs of toxicity after treatment with AHRL1.

Suppression of insulitis and diabetes in TCDD treated NOD mice is associated with an increased population of Foxp3 positive (Foxp3+) Tregs in the PLN at 30 weeks of age. To determine if suppression of insulitis by AHRL1 was also associated with an increased Foxp3+ Tregs population, the leukocyte composition of the pancreas and draining lymph nodes of AHRL1 treated mice were compared to vehicle treated mice.

FIGS. 3a-3f illustrate results comparing the leukocyte composition of the vehicle treated NOD mice to the ARHL1 treated NOD mice from FIG. 2b. The leukocyte composition of the vehicle treated NOD mice to the ARHL1 treated NOD mice was analyzed at 12 weeks of age. Student's t-test was used for analysis. Sample size of n=5-9 mice per group was used. A single asterisk (*) signifies p≤0.05; a double asterisk () signifies p≤0.01; a triple asterisk (*) signifies p≤0.001.

Figure 3A:
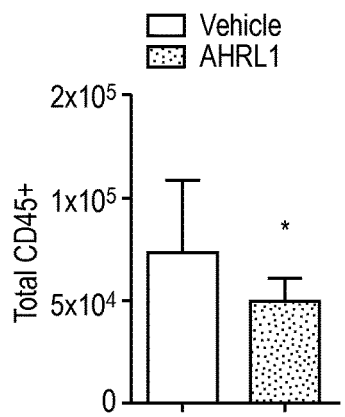
FIGS. 3a-3f illustrate treatment with AHRL1 increases a percentage rather than total number of pancreatic CD4+ Foxp3+ cells.

FIG. 3a compares the total number of cluster of differentiation 45 positive (CD45+) cells in the pancreas of ARHL1 treated mice to vehicle treated mice. FIG. 3a shows the total number of CD45+ cells infiltrating the pancreas was decreased in AHRL1 treated mice as compared to vehicle treated mice. The reduction in the number of CD45+ cells infiltrating the pancreas of AHRL1 treated mice correlates with, and further supports, the results showing AHRL1 treatment prevented islet infiltration by CTL (FIG. 2c).

Figure 3B:
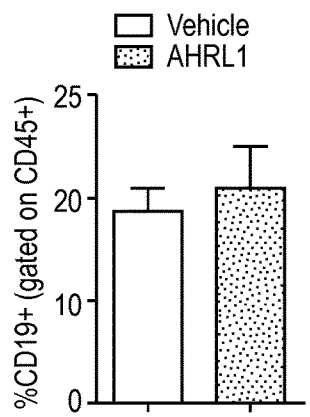

FIG. 3b compares the percentage of cluster of differentiation 19 positive (CD19+) B cells gated on CD45+ cells, i.e., the percentage of CD45+ cells that were CD19+, in vehicle treated mice to AHRL1 treated mice. FIG. 3b shows the percentage of pancreatic CD45+CD19+ B cells in AHRL1 treated mice was commensurate with the percentage of pancreatic CD45+CD19+ B cells in vehicle treated mice. The commensurate percentages of CD45+CD19+ B cells in AHRL1 treated mice and vehicle treated mice indicates activation of AhR by AHRL1, 11-Cl-BBQ, 10-Cl-BBQ, an 11-Cl-BBQ analog, or combinations thereof does not alter the proportion of pancreatic CD45+CD19+ B cells.

Figure 3C:
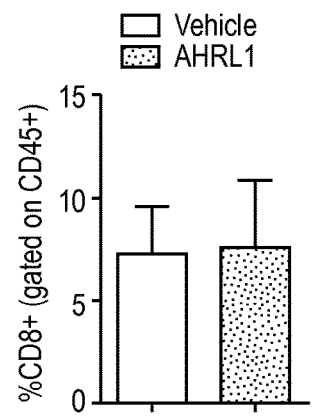

FIG. 3c compares the percentage of CD8+ cells gated on CD45+ cells, i.e., the percentage of CD45+ cells that were CD8+, in vehicle treated mice to AHRL1 treated mice. FIG. 3c shows the percentage of pancreatic CD45+CD8+ cells in AHRL1 treated mice was commensurate with the percentage of pancreatic CD45+CD8+ cells in vehicle treated mice. The commensurate percentages of CD45+CD8+ cells in AHRL1 treated mice and vehicle treated mice indicates activation of AhR with AHRL1, 11-Cl-BBQ, 10-Cl-BBQ, an 11-Cl-BBQ analog, or combinations thereof does not alter the proportion of pancreatic CD45+CD8+ cells.

Figure 3D:
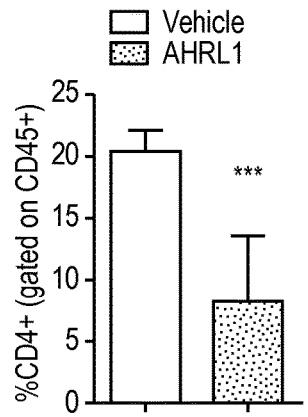

FIG. 3d compares the percentage of CD4+ cells gated on CD45+ cells, i.e., the percentage of CD45+ cells that were CD4+, in vehicle treated mice to AHRL1 treated mice. FIG. 3d shows the percentage of pancreatic CD45+CD4+ cells in AHRL1 treated mice was significantly reduced as compared to the percentage of pancreatic CD45+CD4+ cells in vehicle treated mice. The reduced percentage of CD45+CD4+ and reduced total number of CD45+ cells in AHRL1 treated mice as compared to vehicle treated mice indicates activation of AhR by AHRL1, 11-Cl-BBQ, 10-Cl-BBQ, an 11-Cl-BBQ analog, or combinations thereof reduces the number of CD45+CD4+ cells in the pancreas.

Figure 3E:
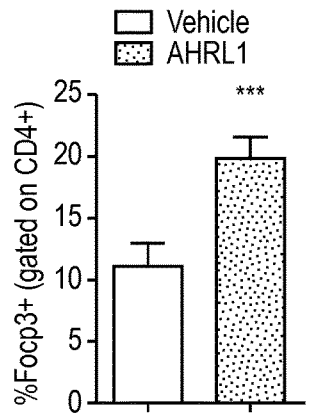

FIG. 3e compares the percentage of Foxp3+ cells gated on CD4+ cells, i.e., the percentage of CD4+ cells that were Foxp3+, in vehicle treated mice to AHRL1 treated mice.

FIG. 3e shows the percentage of pancreatic CD4+Foxp3+ cells in AHRL1 treated mice was significantly increased as compared to the percentage of pancreatic CD4+Foxp3+ cells in vehicle treated mice. The increased percentage of CD4+Foxp3+ cells in AHRL1 treated mice as compared to vehicle treated mice indicates activation of AhR by AHRL1, 11-Cl-BBQ, 10-Cl-BBQ, an 11-Cl-BBQ analog, or combinations thereof increases a percentage of CD4+Foxp3+ cells. Thus, administering AHRL1, 11-Cl-BBQ, 10-Cl-BBQ, an 11-Cl-BBQ analog, or combinations thereof can increase a percentage of pancreatic Foxp3+ Tregs.

Figure 3F:

FIG. 3f compares a total number of CD4+Foxp3+ cells in the pancreas of vehicle treated mice to AHRL1 treated mice. FIG. 3f shows the total number of CD4+Foxp3+ cells in the pancreas of vehicle treated mice was commensurate with the total number of CD4+Foxp3+ cells in the pancreas of AHRL1 treated mice. The consistency in the total number of CD4+Foxp3+ cells in vehicle treated mice as compared AHRL1 treated mice, even though CD4+Foxp3+ percentage was higher in AHRL1 treated mice, is attributable to AHRL1 decreasing the total number of CD45+ cells and the percentage of CD45+ cells that were CD4+. Thus, AHRL1 reduces the total number of CD45+ and CD45+CD4+ cells, but increases the percentage of CD4+ cells that express Foxp3+. In other words, AHRL1 reduces the number of CD4+ cells that are Foxp3 negative (CD4+Foxp3– cells) in the pancreas. The increased percentage of CD4+Foxp3+ cells in AHRL1 treated mice as compared to vehicle treated mice and commensurate total number of CD4+Foxp3+ cells in AHRL1 treated mice as compared to vehicle treated mice indicates activation of AhR by AHRL1, 11-Cl-BBQ, 10-Cl-BBQ, an 11-Cl-BBQ analog, or combination thereof increases the proportion, rather than total number, of Foxp3+ Tregs in the pancreas.

To further study the effects of AHRL1 on T cell differentiation, the leukocyte composition of draining lymph nodes of the vehicle treated, AHRL1 treated, and TCDD treated NOD mice were analyzed at 12, 15, and 20 weeks of age.

Figure 4A:
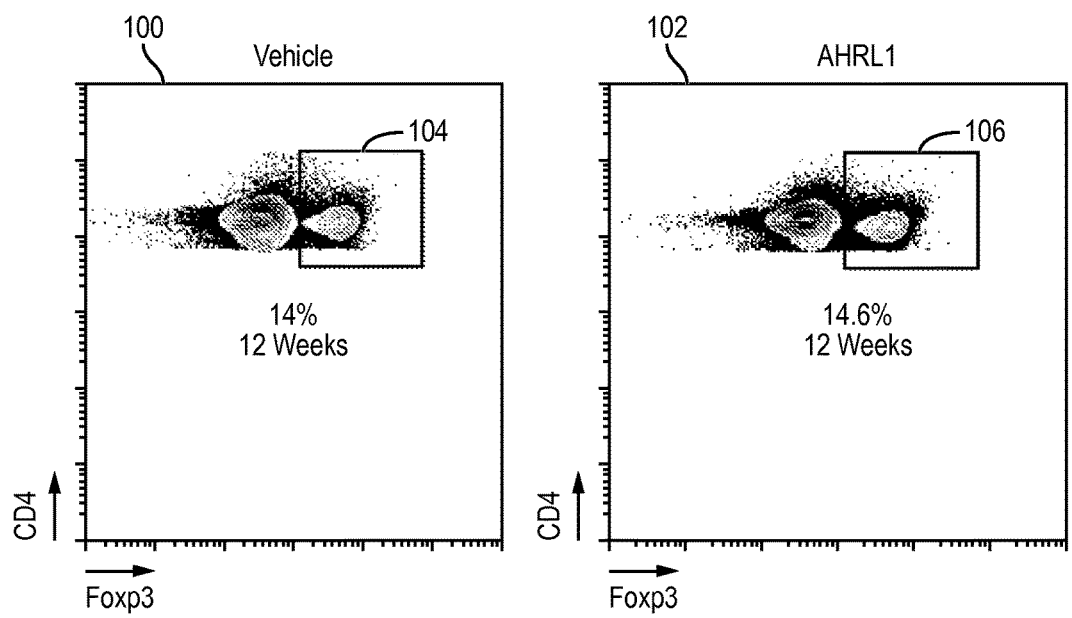
FIGS. 4a-4t illustrate treatment with AHRL1 increases a percentage rather than total number of CD4+Foxp3+ cells in the pancreatic lymph node (PLN)
Figure 4B:
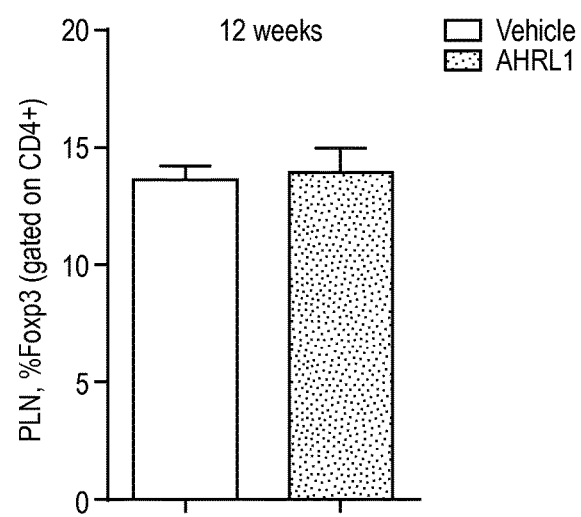
Figure 4C:
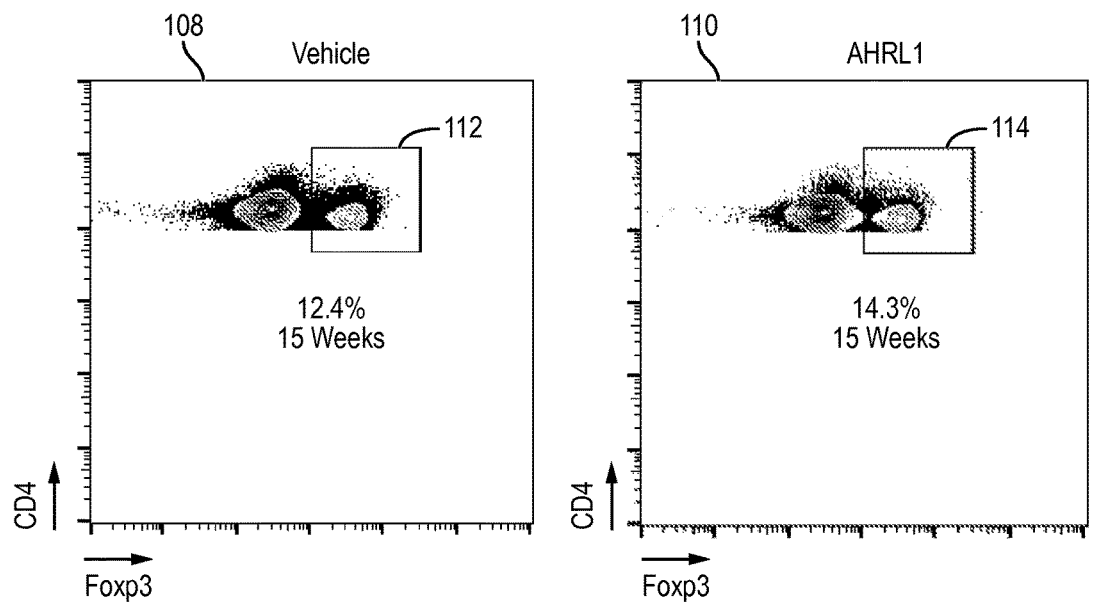
Figure 4D:
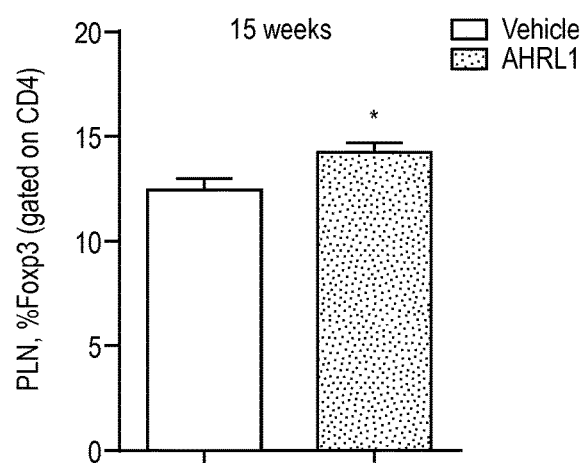
Figure 4E:
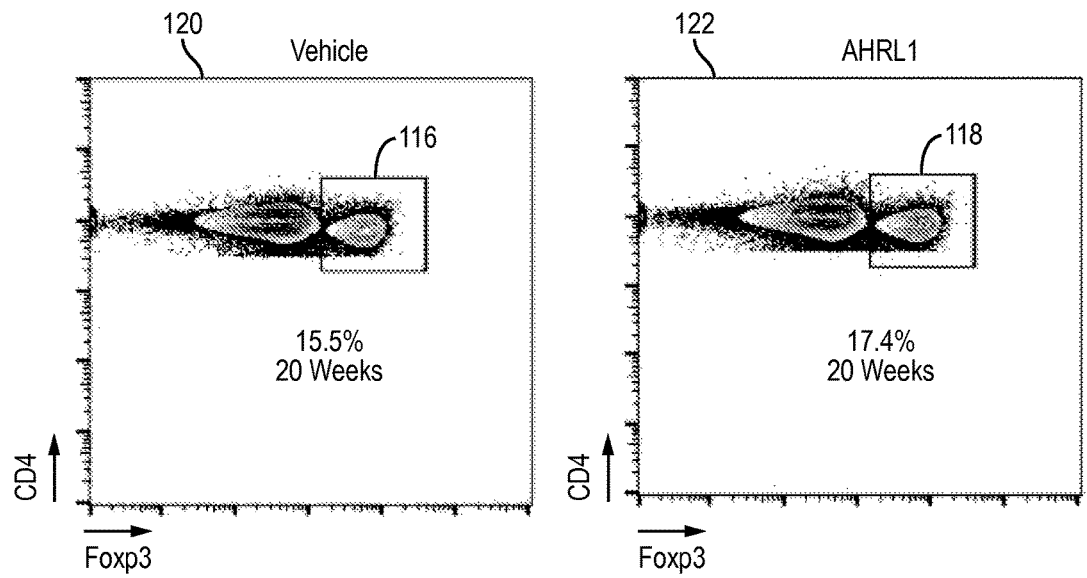
Figure 4F:
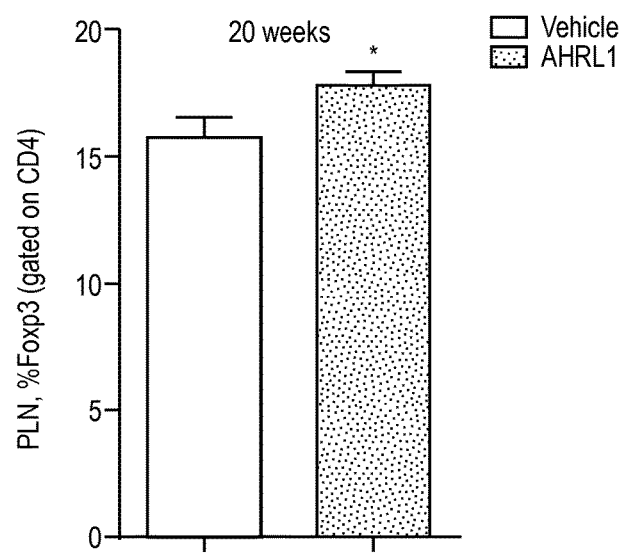
Figure 4G:
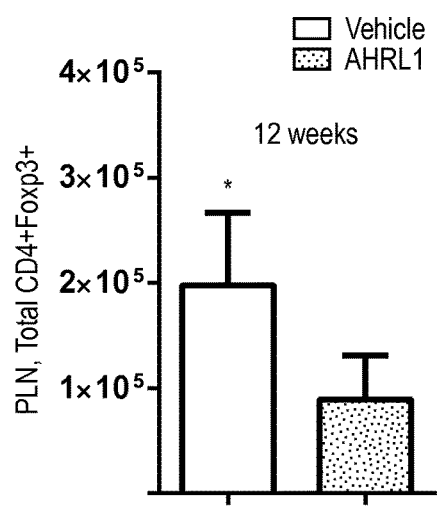
Figure 4H:
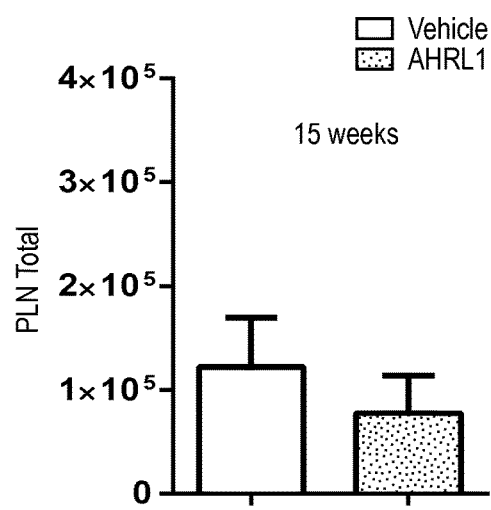
Figure 4I:
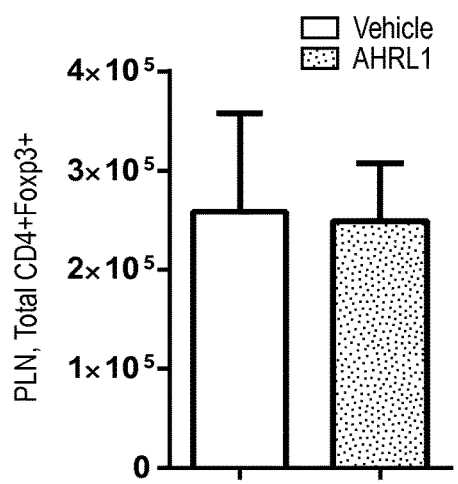
Figure 4J:
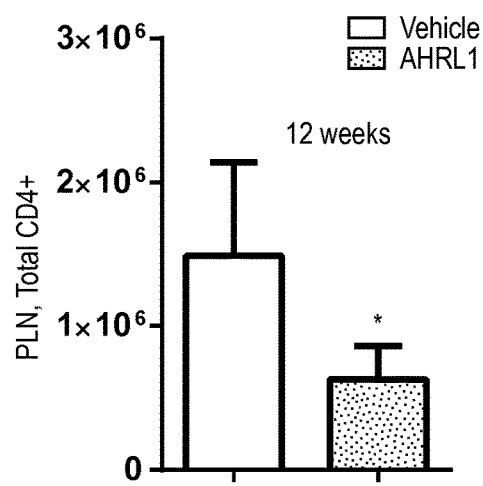
Figure 4K:
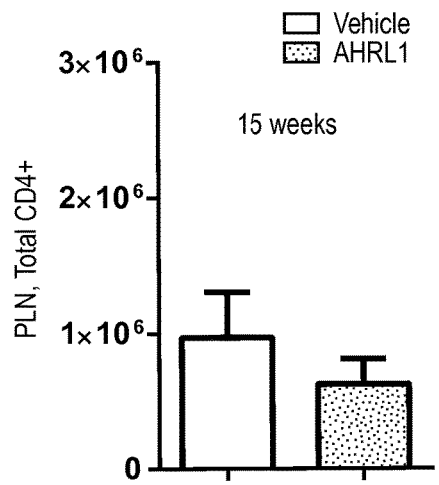
Figure 4L:
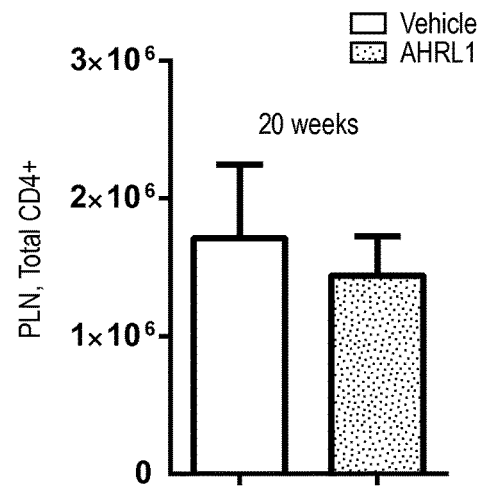
Figure 4M:
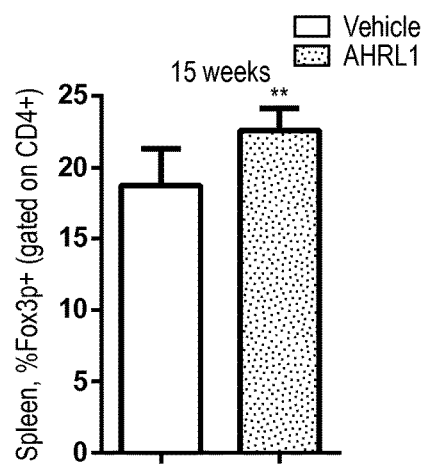
Figure 4N:
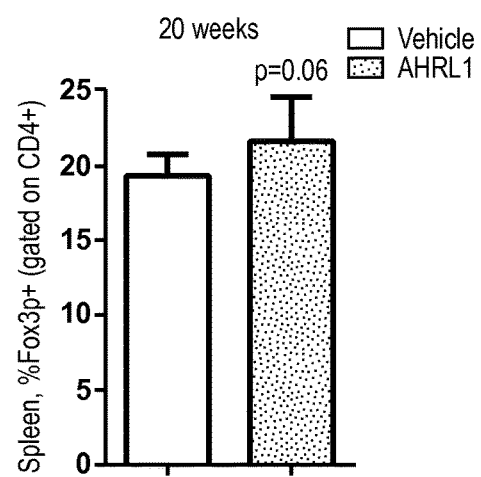
Figure 4O:
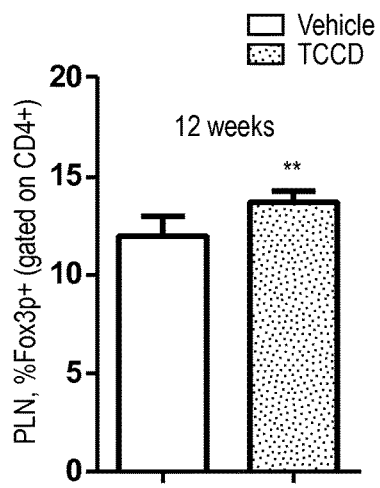
Figure 4P:
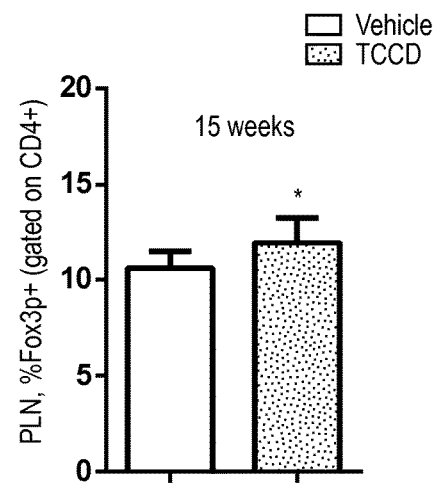
Figure 4Q:
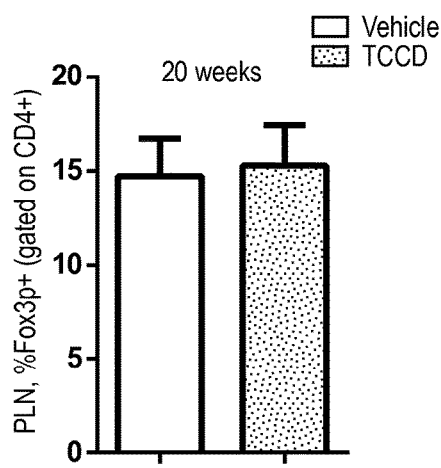
Figure 4R:
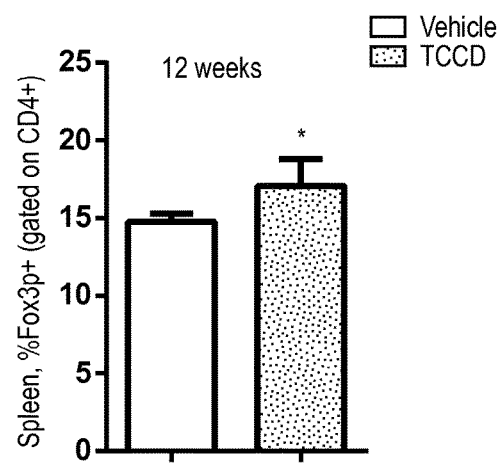
Figure 4S:
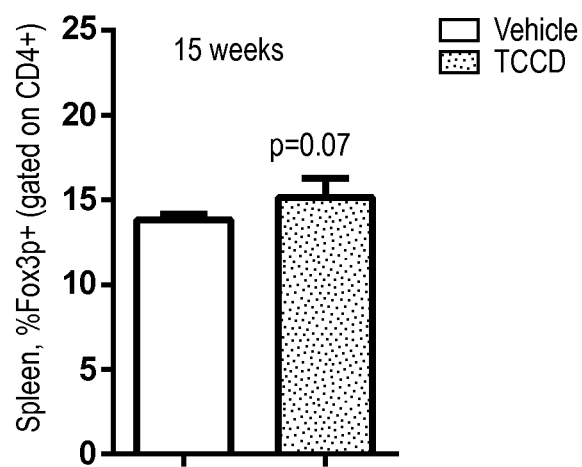
Figure 4T:
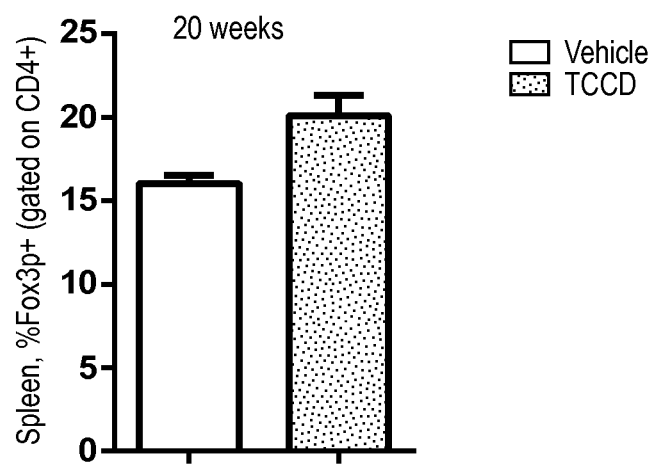

FIGS. 4a-4t illustrate results comparing leukocyte composition of draining lymph nodes in vehicle treated, AHRL1 treated, and TCDD treated NOD mice at 12, 15, and 20 weeks of age. Seven-week-old NOD mice were treated with vehicle, AHRL1, or TCDD as described with reference to FIG. 2b. At 12 weeks of age, 15 weeks of age, and 20 weeks of age, the draining lymph nodes were excised from the mice and stained with CD4 antibodies and Foxp3 antibodies. The results were analyzed by flow cytometry and plotted as average +/−standard deviation (s.d.). A sample size of n=5-9 mice per group was used. A single asterisk (*) signifies $p \leq 0.05$.

FIGS. 4a and 4b compare the percentage of Foxp3+ cells gated on CD4+ cells (i.e., the percentage of CD4+ cells that were Foxp3+) in the PLN of vehicle treated mice to AHRL1 treated mice at 12 weeks of age. Rectangular region 104 in histogram 100 of FIG. 4a shows 14.0% of CD4+ cells in the PLN of vehicle treated mice were Foxp3+. Rectangular region 106 in histogram 102 of FIG. 4a shows 14.6% of CD4+ cells in the PLN of AHRL1 treated mice were Foxp3+. FIG. 4b illustrates the data shown in histograms 100 and 102 as a bar graph.

FIGS. 4c and 4d compare the percentages of Foxp3+ cells gated on CD4+ cells in the PLN of vehicle treated mice to AHRL1 treated mice at 15 weeks of age. Rectangular region 112 in histogram 108 of FIG. 4c shows 12.4% of CD4+ cells in the PLN of vehicle treated mice were Foxp3+. Rectangular region 114 in histogram 110 of FIG. 4c shows 14.3% of CD4+ cells in the PLN of AHRL1 treated mice were Foxp3+. FIG. 4c illustrates the data of histograms 108 and 110 as a bar graph.

FIGS. 4e and 4f compare the percentages of Foxp3+ cells gated on CD4+ cells in the PLN of vehicle treated and AHRL1 treated mice at 20 weeks of age. Rectangular region 116 in histogram 120 of FIG. 4e shows 15.5% of CD4+ cells in the PLN of vehicle treated mice were Foxp3+. Rectangular region 118 in histogram 122 of FIG. 4e shows 17.4% of CD4+ cells in the PLN of AHRL1 treated mice were Foxp3+. FIG. 4f illustrates the data shown in histograms 120 and 122 as a bar graph.

FIGS. 4c-4e show that at 15 and 20 weeks of age, there was an increase in the percentage of CD4+ cells that were Foxp3+(i.e., Foxp3+ Tregs) in the PLN of AHRL1 treated mice as compared to vehicle treated mice. The increase in the percentage of Foxp3+ Tregs in AHRL1 treated mice indicates that activating AhR with AHRL1, 11-Cl-BBQ, 10-CL-BBQ, an 11-Cl-BBQ analog, or combination thereof can alter T cell differentiation and increase a percentage Foxp3+ Tregs in the PLN.

FIGS. 4g, 4h, and 4i compare a total number of CD4+Foxp3+ cells in the PLN of vehicle treated mice to AHRL1 treated mice at 12, 15, and 20 weeks of age, respectively. FIG. 4g shows that at 12 weeks of age, the total number of CD4+Foxp3+ cells was lower in AHRL1 treated mice as compared to vehicle treated mice. The increased percentage of CD4+ cells expressing Foxp3+, but lower or commensurate number of total CD4+Foxp3+ cells in the PLN of AHRL1 treated mice as compared to vehicle treated mice demonstrates that activation of AhR by AHRL1, 11-Cl-BBQ, 10-Cl-BBQ, an 11-Cl-BBQ analog, or combinations thereof increases the percentage, but not total number, of CD4+Foxp3+ cells in the PLN. Thus, treatment with AHRL1, 11-Cl-BBQ, 10-Cl-BBQ, an 11-Cl-BBQ analog, or combinations thereof may be used to alter T cell differentiation and increase the percentage, but not total number, of Foxp3+ Tregs in the PLN.

FIGS. 4j, 4k, and 4l compare a total number of CD4+ cells, i.e., CD4+Foxp3– cells, in the PLN of vehicle treated mice to AHRL1 treated mice at 12, 15, and 20 weeks of age, respectively. FIGS. 4j, 4k, and 4l show mice treated with AHRL1 had a lower total number of CD4+Foxp3– cells as compared to vehicle treated mice. FIGS. 4j, 4k, and 4l demonstrate that activation of AhR by AHRL1, 11-Cl-BBQ, 10-Cl-BBQ, an 11-Cl-BBQ analog, or combinations thereof decreases the total number of CD4+Foxp3– cells in the PLN. A decrease in the total number of CD4+Foxp3– cells in AHRL1 treated mice further demonstrates that treatment with AHRL1, 11-Cl-BBQ, 10-Cl-BBQ, an 11-Cl-BBQ analog, or combinations thereof can lead to an increase in the percentage, rather than number, of Foxp3+ Tregs in the PLN.

FIGS. 4m and 4n compare the percentage of Foxp3+ cells gated on CD4+ cells in the spleen of vehicle treated mice to AHRL1 treated mice at 15 and 20 weeks of age, respectively. FIG. 4m shows there was a higher percentage of CD4+Foxp3+ cells in the spleen of AHRL1 treated mice as compared to vehicle treated mice at 15 weeks of age. FIG. 4n shows there was a higher percentage of CD4+Foxp3+ cells in the spleen of AHRL1 treated mice as compared to vehicle treated mice at 20 weeks of age. The increased percentage of CD4+ cells expressing Foxp3+ in AHRL1 treated mice indicates activation of AhR by 11-Cl-BBQ, 10-Cl-BBQ, an 11-Cl-BBQ analog, or combinations thereof can increase a percentage of CD4+Foxp3+ Tregs in the spleen.

FIGS. 4o, 4p, and 4q compare the percentage of Foxp3+ cells gated on CD4+ cells in the PLN of vehicle treated mice to TCDD treated mice at 12, 15, and 20 weeks of age, respectively. FIG. 4o shows there was a higher percentage of CD4+Foxp3+ cells in the PLN of TCDD treated mice as compared to vehicle treated mice at 12 weeks of age. FIG. 4p shows there was a higher percentage of CD4+Foxp3+ cells in the PLN of TCDD treated mice as compared to vehicle treated mice at 15 weeks of age. FIG. 4q shows a higher percentage of CD4+Foxp3+ cells in the PLN of TCDD treated mice as compared to vehicle treated mice at 20 weeks of age. The increased percentage of CD4+Foxp3+ cells in the PLN of TCDD tested mice as compared to vehicle treated mice demonstrates activation of AhR by an AhR ligand increases the percentage of CD4+Foxp3+ Tregs in the PLN.

FIGS. 4r, 4s, and 4t compare the percentage of Foxp3+ cells gated on CD4+ cells in the spleen of vehicle treated mice to TCDD treated mice at 12, 15, and 20 weeks of age, respectively. FIG. 4r shows a higher percentage of CD4+Foxp3+ cells in the spleen of TCDD treated mice as compared to vehicle treated mice at 12 weeks of age. FIG. 4s shows at 15 weeks of age, TCDD treated mice had a higher percentage of CD4+Foxp3+ cells in the spleen than vehicle treated mice. FIG. 4t shows at 20 weeks of age, TCDD treated mice had a higher percentage of CD4+Foxp3+ cells in the spleen as compared to vehicle treated mice. The increased percentage of CD4+Foxp3+ cells in the spleen of TCDD treated mice as compared to vehicle treated mice indicates activation of AhR by an AhR ligand is increasing the percentage of Foxp3+ Tregs in the spleen.

To further characterize the CD4+Foxp3+ Tregs induced by activation of AhR by AhR ligands, co-expression of Foxp3 with the high affinity interleukin-2 (IL-2) receptor CD25, and co-expression of Foxp3 with neuropilin-1 (Nrp1) were assessed in the PLN of vehicle treated mice and AHRL1 treated mice at 20 weeks of age.

Figure 5A:
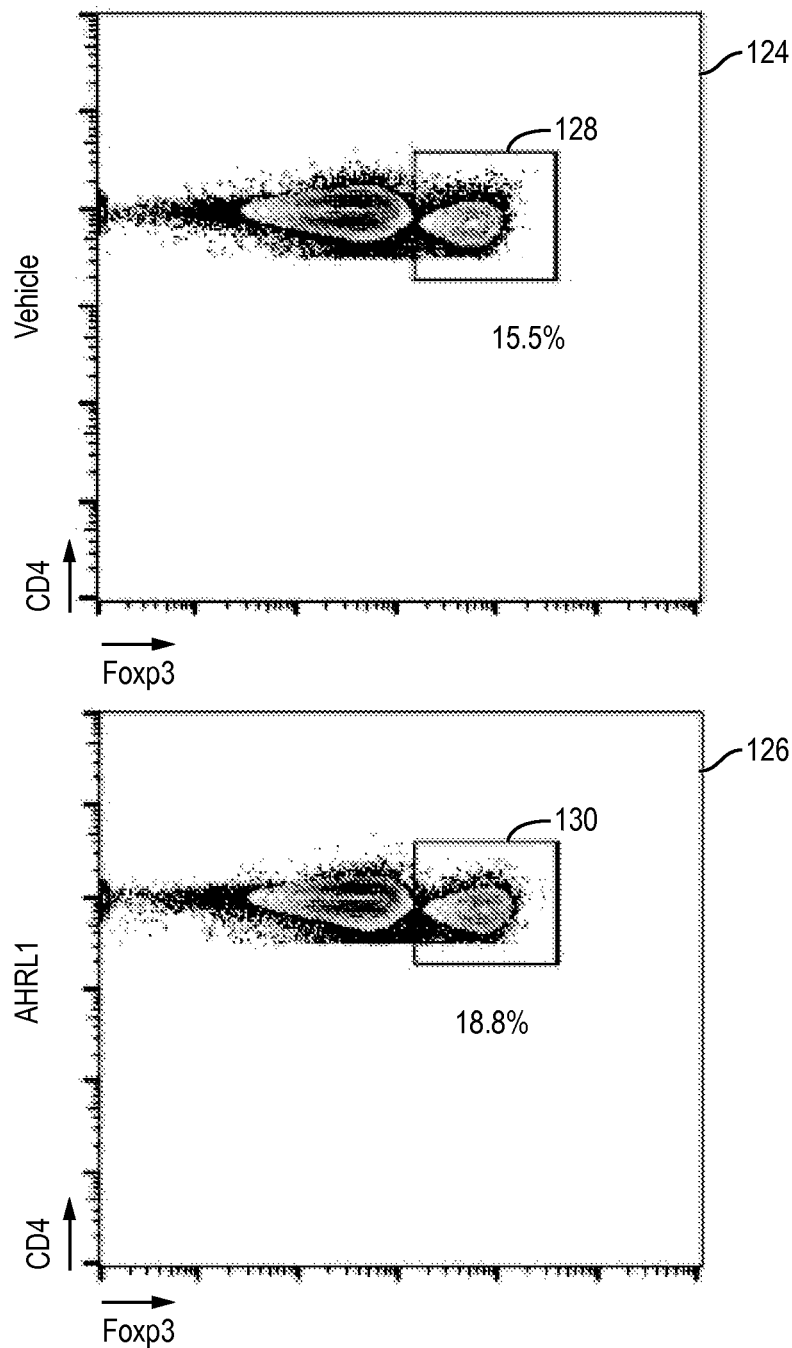
FIGS. 5a-5e illustrate treatment with AHRL1 increases a percentage of CD4+Foxp3+Nrp1− cells in the PLN.

FIGS. 5a-5e compare expression levels of CD25 and Nrp1 in Foxp3+ cells in the PLN of AHRL1 treated NOD mice to vehicle treated NOD mice. FIG. 5a illustrates a percentage of Foxp3+ cells gated on in CD4+ cells in the PLN of vehicle treated mice (histogram 124) and AHRL1 treated mice (histogram 126). Data were taken at 20 weeks of age. Rectangular region 128 in histogram 124 shows 15.5% of CD4+ cells in vehicle treated mice were Foxp3+. Rectangular region 130 in histogram 126 shows 18.8% of CD4+ cells in AHRL1 treated mice were Foxp3+.

Figure 5B:
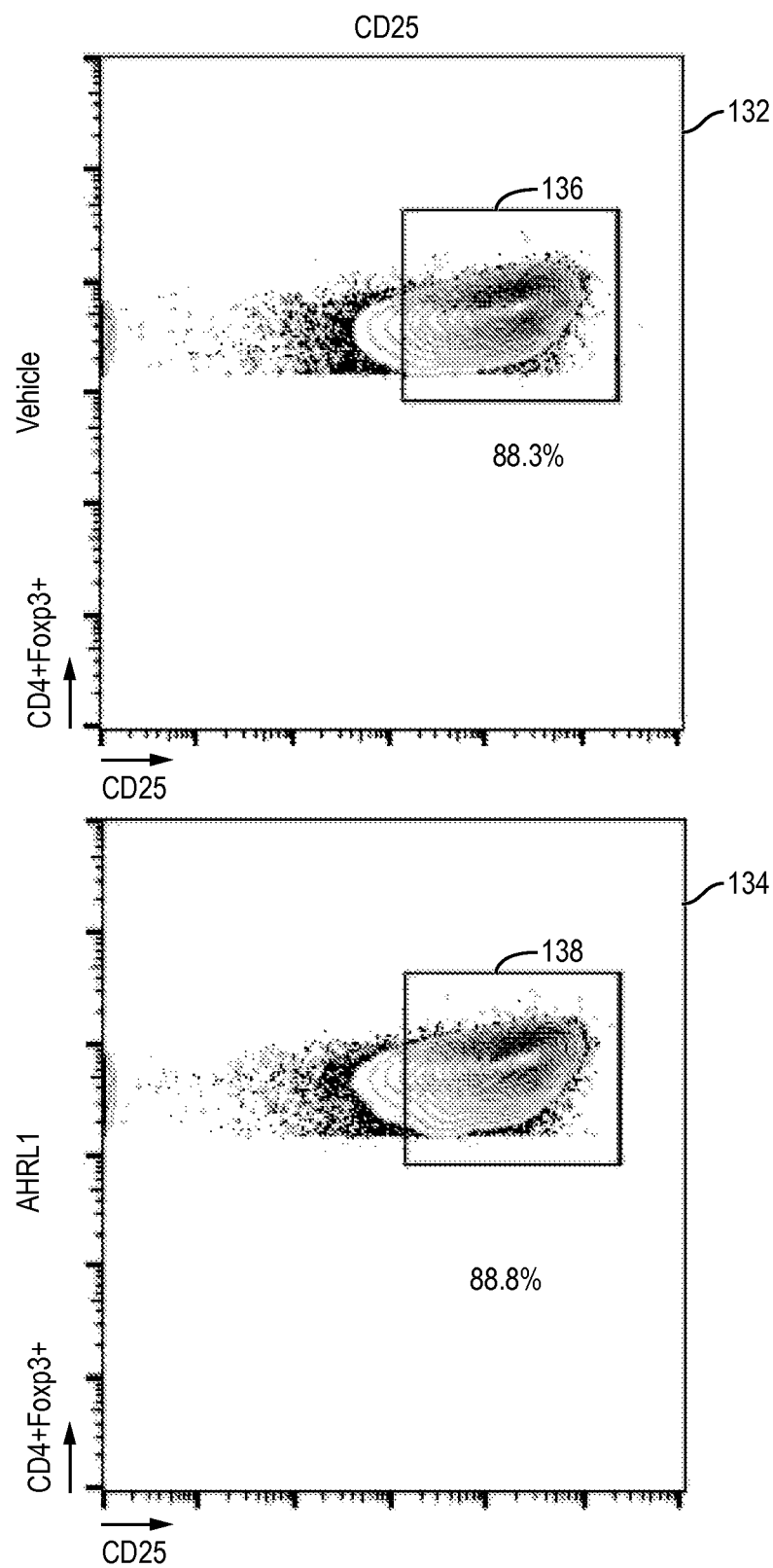
Figure 5C:
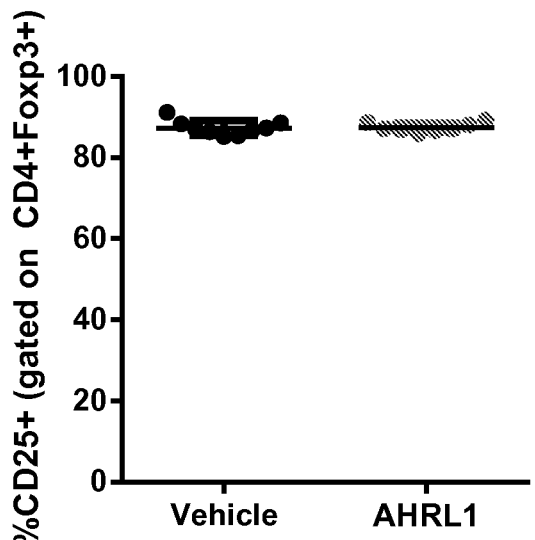

FIGS. 5b and 5c illustrate the percentage of CD25 positive (CD25+) cells gated on the CD4+Foxp3+ PLN cells of FIG. 5a, i.e., the percentage of CD4+Foxp3+ PLN cells that were CD25+. Rectangular region 136 in histogram 132 of FIG. 5b shows 88.3% of CD4+Foxp3+ cells from region 128 in FIG. 5a were CD25+. Rectangular region 138 in histogram 134 of FIG. 5b shows 88.8% of CD4+Foxp3+ cells from region 130 in FIG. 5a were CD25+. FIG. 5c illustrates the data shown in histograms 132 and 134 of FIG. 5b. FIGS. 5b and 5c show CD4+Foxp3+ cells in AHRL1 treated and vehicle treated mice had commensurate percentages of CD25 expression. The commensurate percentage of CD4+Foxp3+CD25+ cells in the PLN of AHRL1 treated mice as compared to vehicle treated mice demonstrates activation of AhR by AHRL1, 11-Cl-BBQ, 10-Cl-BBQ, an 11-Cl-BBQ analog, or combination thereof does not alter expression of CD25+ in CD4+Foxp3+ PLN cells.

Figure 5E:
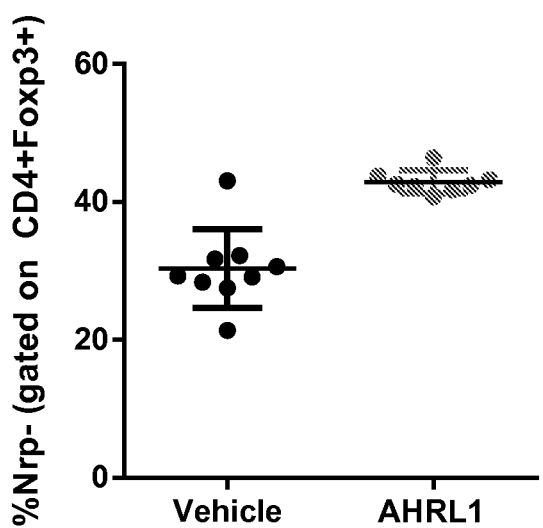
Figure 5D:
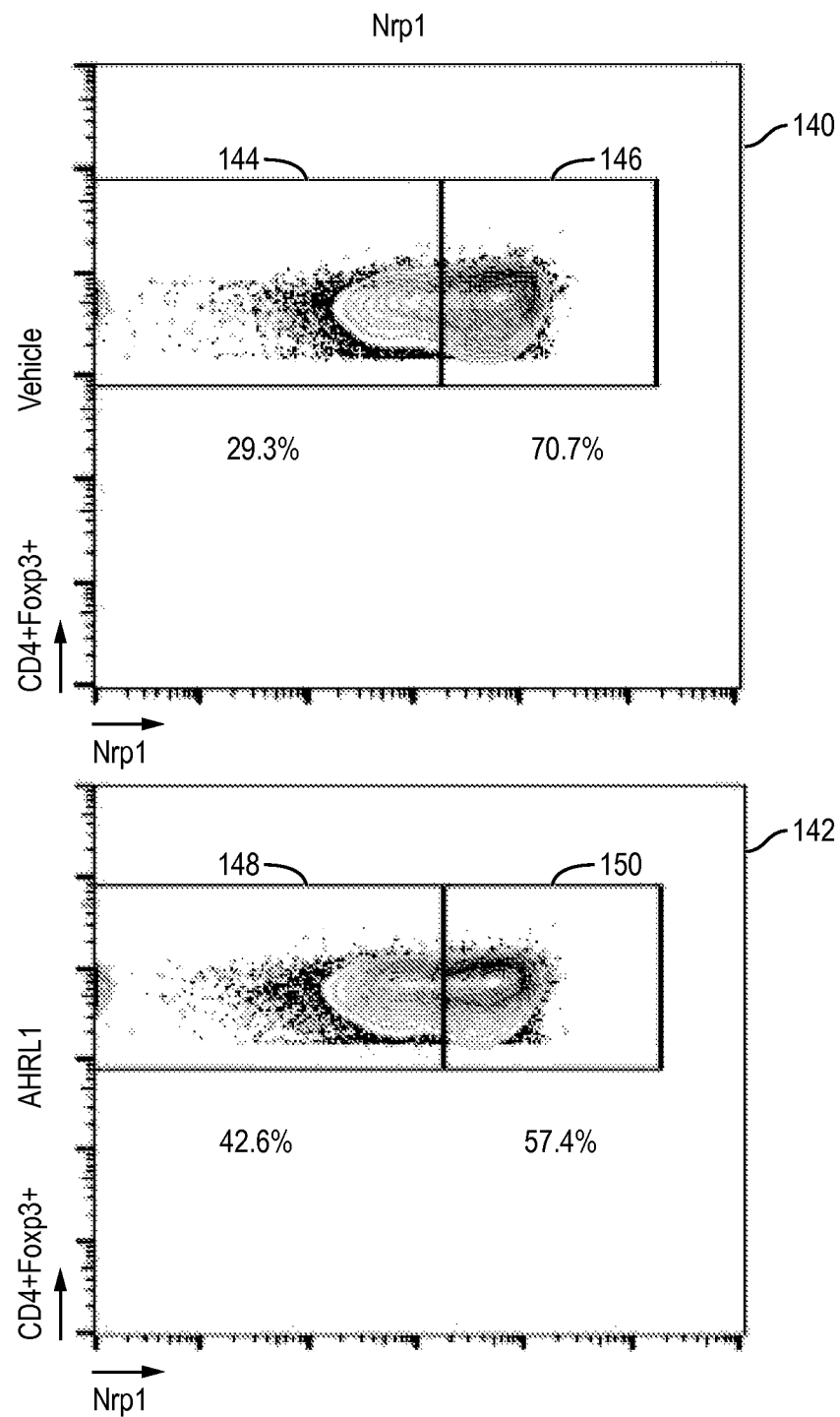

FIGS. 5d and 5e illustrate percentages of Nrp1 positive (Nrp1+) and Nrp1 negative (Nrp1−) cells gated on the CD4+Foxp3+ cells of FIG. 5a, i.e., the percentage of the CD4+Foxp3+ cells that were Nrp1+ and the percentage of CD4+Foxp3+ cells that were Nrp1−. Rectangular region 144 in histogram 140 of FIG. 5d shows 29.3% of the CD4+Foxp3+ cells from region 128 in FIG. 5a were Nrp1−. Rectangular region 146 in histogram 140 of FIG. 5d shows 70.7% of the CD4+Foxp3+ cells from region 128 in FIG. 5a were Nrp1+. Rectangular region 148 in histogram 142 of FIG. 5d shows 42.6% of CD4+Foxp3+ cells from region 130 in FIG. 5a were Nrp1−. Rectangular region 150 in histogram 142 of FIG. 5d shows 57.4% of the CD4+Foxp3+ cells from region 130 in FIG. 5a were Nrp1+. FIG. 5e illustrates the data shown in region 144 and region 148, i.e., the percentage of CD4+Foxp3+ cells that were Nrp1− in the PLN of AHRL1 treated mice and vehicle treated mice. FIGS. 5d and 5e illustrate AHRL1 treatment shifted the proportion of Foxp3+ cells from an approximately equal proportion of Nrp1+ and Nrp1− in Foxp3+ cells of vehicle treated mice to predominately Nrp1− negative population of Foxp3+ cells.

Taken together, FIGS. 5a-5e illustrate AhR activation by AHRL1 is not expanding the population of thymic-derived nTregs, but is instead inducing or predominantly maintaining peripherally-induced pTregs.

AHRL1 treatment resulted in an increased percentage of Foxp3+ cells in the pancreas and PLN of NOD mice. To further analyze the therapeutic effects and mechanisms of AHRL1 treatment of autoimmune disease, a non-obese diabetic Foxp3 deficient (NOD.Foxp3−) mouse model experiment was conducted.

FIGS. 6a-6e illustrate the therapeutic effects of treatment with an AhR ligand on a Foxp3 deficient subject using a NOD.Foxp3− mouse model. To directly determine if Foxp3+ Tregs are functionally required for suppression of insulitis by AhR ligands, islet infiltration was measured in NOD.Foxp3− mice treated with vehicle, AHRL1, or TCDD. NOD.Foxp3− mice were obtained by treating non-obese diabetic Foxp3 diphtheria toxin receptor mice (NOD.Foxp3DTR mice)) with diphtheria toxin (DT). NOD.Foxp3$^{DTR}$ mice were obtained from the Juvenile Diabetes Research Foundation Center (JDRF) for Immune Tolerance in Diabetes at Harvard (CITDH). Mice were bred and maintained under specific pathogen-free conditions at Oregon State University facilities. All experimental procedures using animals were approved by the Institutional Animal Care and Use Committee at Oregon State University.

Figure 6A:
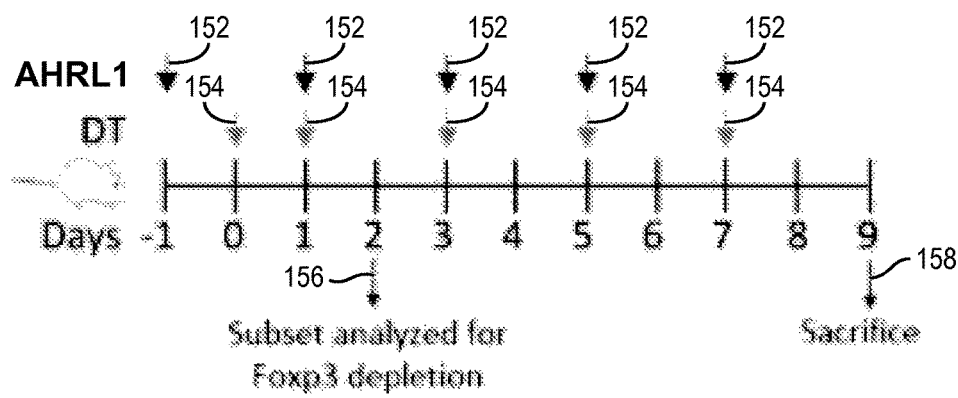
FIGS. 6a-6e illustrate AhR ligands do not require Foxp3+ Treg cells to suppress pancreatic islet infiltration.

FIG. 6a illustrates details of the mouse model used to analyze the therapeutic effects and mechanisms by which AhR activation alters T cell differentiation. Arrows 154 show that on days 0, 1, 3, 5, and 7 NOD.Foxp3$^{DTR}$ mice between 4 and 6 weeks of age were injected with DT. Arrows 152 illustrate the NOD.Foxp3$^{DTR}$ mice were orally dosed with 60 mg/kg AHRL1 on days −1, 1, 3, 5, and 7 relative to DT treatment on day 0. The carrier for AHRL1 was a 30% DMSO, 20% CREMAPHOR, 50% PECEOL solution. Data was also collected from NOD.Foxp3$^{DTR}$ mice treated with TCDD on day −1 relative to DT treatment on day 0. Arrow 156 shows two days following the initiation of DT treatment a subset of mice (n=3) was analyzed for Foxp3 depletion. Non-obese diabetic Foxp3 wild type (NOD.Foxp3$^{WT}$) mice treated with DT and NOD.Foxp3$^{DTR}$ mice treated with vehicle were used as controls. The vehicle was the carrier for AHRL1. Arrow 158 illustrates sacrifice of the mice on day 9.

The pancreases from the sacrificed mice were excised, sectioned, and stained with hematoxylin and eosin for analysis of islet infiltration by inflammatory CTL cells. Islet infiltration was scored on sequential hematoxylin and eosin stained pancreas sections separated by 200 µm. Islets were scored as no infiltration, less than 50% infiltration, or greater than 50% infiltration. For statistical comparisons of degree of islet infiltration between groups, chi-squared analyses were performed. A sample size of n=7-9 mice per group was used. A single asterisk (*) signifies a p≤0.05; a double asterisk () signifies a p≤0.01; a triple asterisk (*) signifies a p≤0.001.

The leukocyte composition of the pancreas and draining lymph nodes was analyzed using flow cytometry. Draining lymph nodes and pancreata were excised from the sacrificed mice, and single cell suspensions were prepared for analysis with flow cytometry. Fc receptors were blocked with rat IgG (Jackson ImmunoResearch) and the cells were stained with the following antibodies: CD4 (RM4, eBioscience), CD8 (53-6.7, eBioscience), CD19 (1D3, eBioscience), CD45 (30-F11, BD Biosciences), Foxp3 (FJK-16s, eBioscience), Nrp1 (3DS304M, eBioscience), CD25 (PC61.5, eBioscience), RORγt (AFKJS-9, eBioscience). For intracellular staining, cells were fixed and permeabilized using the Foxp3 Fixation/Permeabilization buffer (eBioscience, San Diego, Calif.). Data were acquired using an FC-500 flow cytometer (BECKMAN COULTER) and compensated and analyzed using FLOWJO software. FMO controls were used for setting gates for analysis. Student's t-test was used for analysis of the data. Sample sizes of n=7-9 mice per group was used. A single asterisk (*) signifies p≤0.05; a double asterisk () signifies p≤0.01; a triple asterisk (*) signifies p≤0.001.

Figure 6B:
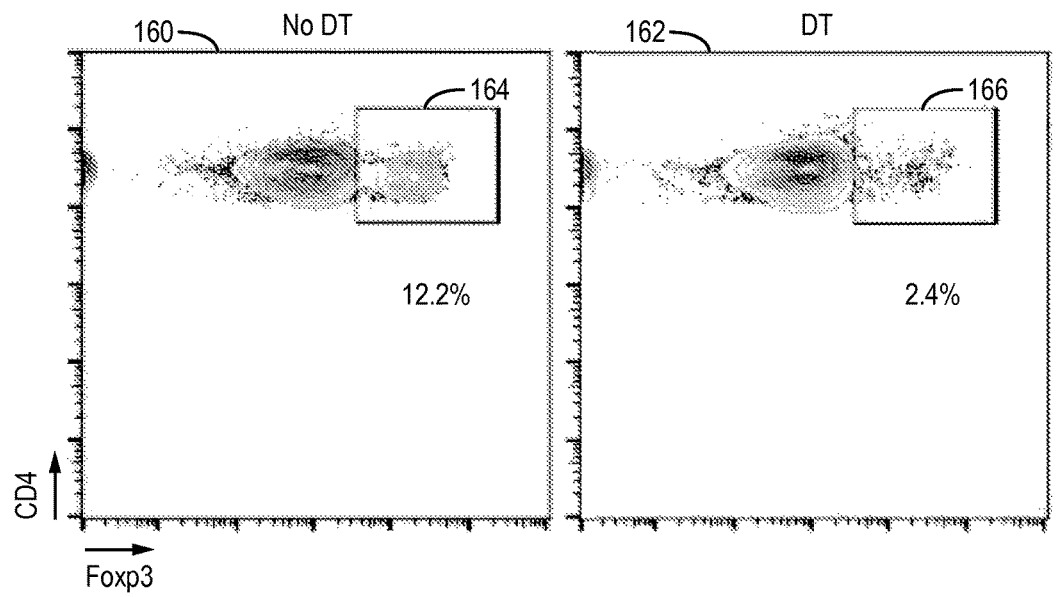
Figure 6C:
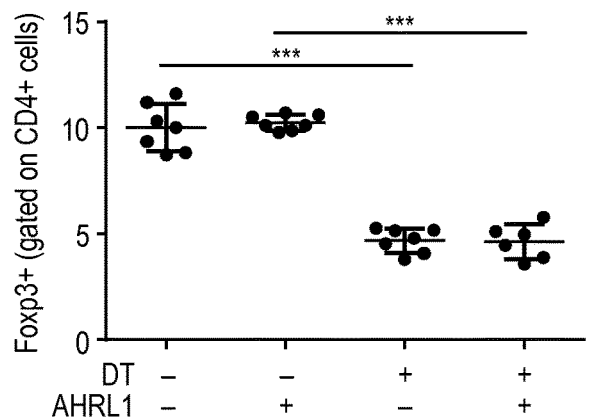

FIG. 6b show analysis of Foxp3 depletion from the subset of mice sacrificed on day 2. Rectangular region 164 in histogram 160 of FIG. 6b shows the percentage of Foxp3+ cells gated on CD4+ cells on day 2 in non-DT treated NOD.Foxp3$^{DTR}$ mice was 12.2%. Rectangular region 166 in histogram 162 of FIG. 6b shows the percentage of Foxp3+ gated on CD4+ cells on day 2 in DT treated NOD.Foxp3$^{DTR}$ mice was 2.4%. FIG. 6b illustrates that after two days following the initiation of DT treatment, approximately 80% of Foxp3+ cells were depleted. FIG. 6c shows the percentage of CD4+Foxp3+ cells in non-DT treated mice, the percentage of CD4+Foxp3+ cells in DT treated mice, and the level of decrease in percentage of CD4+Foxp3+ cells in DT treated mice as compared to non-DT treated mice were consistent between vehicle treated mice and AHRL1 treated mice. FIG. 6c shows treatment of NOD.Foxp3$^{DTR}$ mice with AHRL1 did not alter the Foxp3 depletion efficacy of the DT.

Figure 6D:
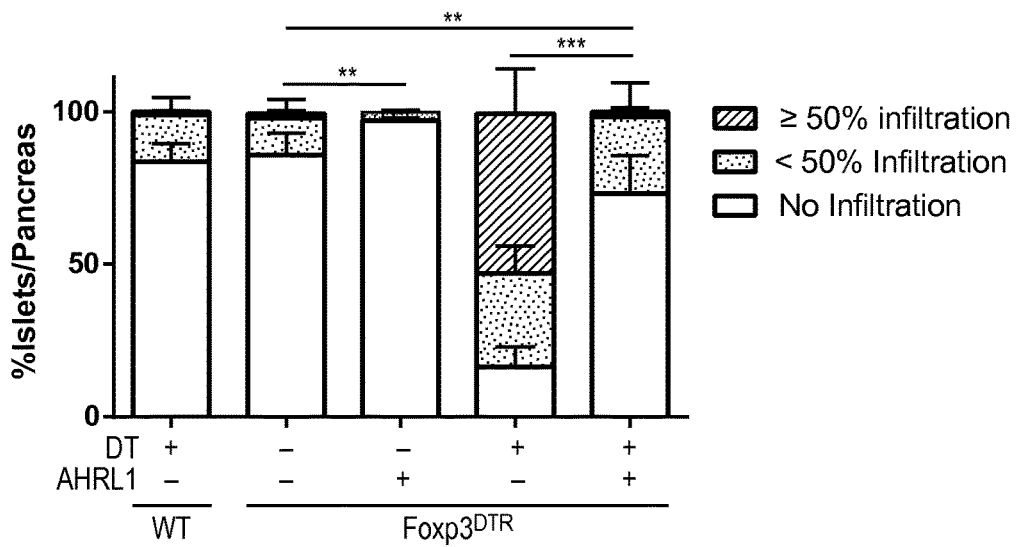

FIG. 6d shows analysis of islet infiltration in DT treated NOD.Foxp3$^{WT}$ mice treated with vehicle, in non-DT treated NOD.Foxp3$^{DTR}$ mice treated with vehicle, in non-DT treated NOD.Foxp3$^{DTR}$ mice treated with AHRL1, in DT treated NOD.Foxp3$^{DTR}$ mice treated with vehicle, and DT treated NOD.Foxp3$^{DTR}$ mice treated with AHRL1. Mice with depleted Foxp3, (i.e., DT treated NOD.Foxp3$^{DTR}$ mice) that were not treated with AHRL1 showed rapid and extensive infiltration in the pancreas with 83.5±16.5% of islets showing infiltration and with 30.5±23.5% of infiltrated islets having less than 50% infiltration and 52.4±38.8% of infiltrated islets having greater than or equal to 50% infiltration. AHRL1 treatment of mice with depleted Foxp3 resulted in 73.2±25.2% of the islets showing no infiltration. FIG. 6d shows AHRL1 treatment significantly decreased infiltration of CTL in mice with depleted Foxp3 as compared to vehicle treated mice with depleted Foxp3.

Figure 6E:
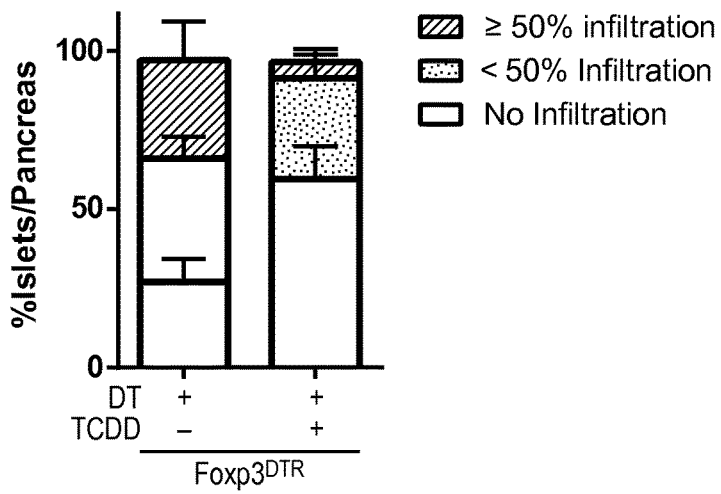

FIG. 6e shows treatment with TCDD also resulted in a greater percentage of islets being free from infiltration in Foxp3 depleted mice, as compared to vehicle treated Foxp3 depleted mice.

FIGS. 6a-6e demonstrate AhR activation suppresses insulitis independently of Foxp3+ Tregs and treatment with AhR ligands does not require Foxp3+ Tregs to suppress pancreatic islet infiltration. The decrease in islet filtration in absence of Foxp3+ Tregs illustrates the ability of AhR activation and treatment with AhR ligands to suppress CTL independently of Foxp3+ Tregs. The ability to suppress CTL independently of Foxp3+ Tregs illustrates the therapeutic potential of AhR ligands to alter T cell differentiation and treat diseases characterized by a decreased number, or absence of, functional Foxp3+ Tregs. Thus, treatment with AHRL1 or other AhR ligands provides a therapeutic strategy for treatment of diseases characterized by an absence or decreased population of Foxp3+ Treg cells.

An acute GVHD model, and in vitro studies, have shown AhR activation can induce a Type 1 regulatory (Tr1)-like Treg. Tr1-like Tregs are characterized by CD25 expression in conjunction with CTLA4, glucocorticoid-induced transferrin receptor family-regulated gene (GITR), and interleukin-10 (IL-10) expression. CD25 expression in NOD-.Foxp3− mice was measured to determine if the suppression of CTL independently of Foxp3+ Tregs was attributable to activation of AhR by AhR ligands inducing Tr1-like Tregs. CD25 expression levels were thus analyzed to ascertain if AhR activation by AHRL1 was causing induction of CD25+ Foxp3− T cells.

Figure 7A:
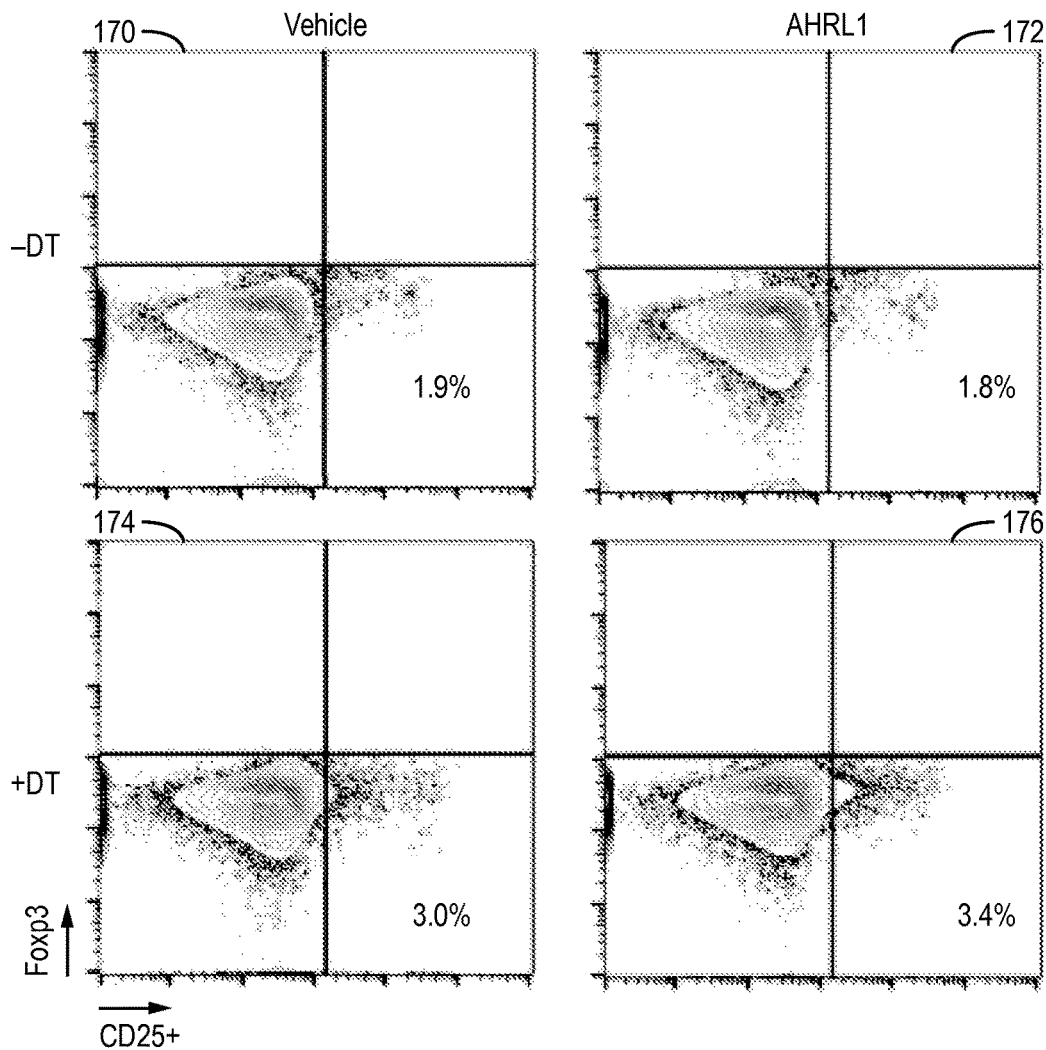
FIGS. 7a-7b illustrate treatment with AHRL1 does not induce compensatory CD25+ Treg cells during Foxp3 depletion.
Figure 7B:
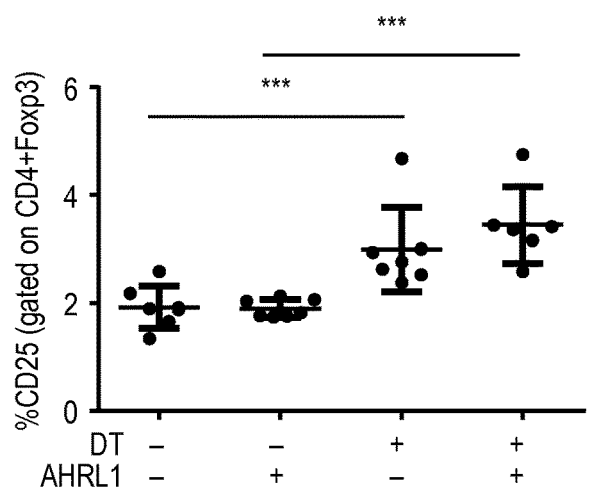

FIGS. 7a and 7b illustrate analysis of CD25+ expression levels in the PLN of NOD.Foxp3− mice. FIG. 7a shows histograms 170, 172, 174, and 176 illustrating CD25+ expression gated on CD4+Foxp3− cells, i.e., the percentage of CD4+Foxp3-cells that were CD25+. In histograms 170, 172, 174, and 176, Foxp3 expression is shown along the y-axis, and CD25 expression is shown along the x-axis. Histogram 170 shows that 1.9% of CD4+Foxp3− cells in non-DT treated NOD.Foxp3DTR mice treated with vehicle were CD25+(i.e., 1.9% were in the bottom right quadrant). Histogram 172 shows that 1.8% of CD4+Foxp3− cells in non-DT treated NOD.Foxp3$^{DTR}$ mice treated with AHRL1 were CD25+. The commensurate percentages of CD4+ Foxp3− cells expressing CD25+ shown in histograms 170 and 172 demonstrates AHRL1 is not inducing CD4+CD25+ Foxp3− cells. Histogram 174 shows that 3.0% of CD4+ Foxp3− cells in DT treated NOD.Foxp3$^{DTR}$ mice treated with vehicle were CD25+. Histogram 176 shows that 3.4% of CD4+Foxp3-cells in DT treated NOD.Foxp3$^{DTR}$ mice treated with AHRL1 were CD25+. The commensurate percentages of CD4+Foxp3− cells expressing CD25+ shown in histograms 174 and 176 demonstrates AHRL1 is not inducing CD4+CD25+Foxp3− cells. FIG. 7b illustrates the CD4+ CD25+Foxp3− data shown in histograms 170, 172, 174, and 176.

FIGS. 7a and 7b show that while the percentage of Foxp3− cells expressing CD25+ cells increased in the PLN after DT treatment (i.e., after depleting Foxp3 cells), AHRL1 treatment did not alter the expression of CD25+ Foxp3− cells as compared to vehicle treated mice. The consistency in percentages of CD25+Foxp3− cells in vehicle treated mice as compared to AHRL1 treated mice demonstrates AHRL1 is suppressing islet infiltration during Foxp3 depletion by a mechanism other than induction of Tr1-like Tregs.

Figure 8A:
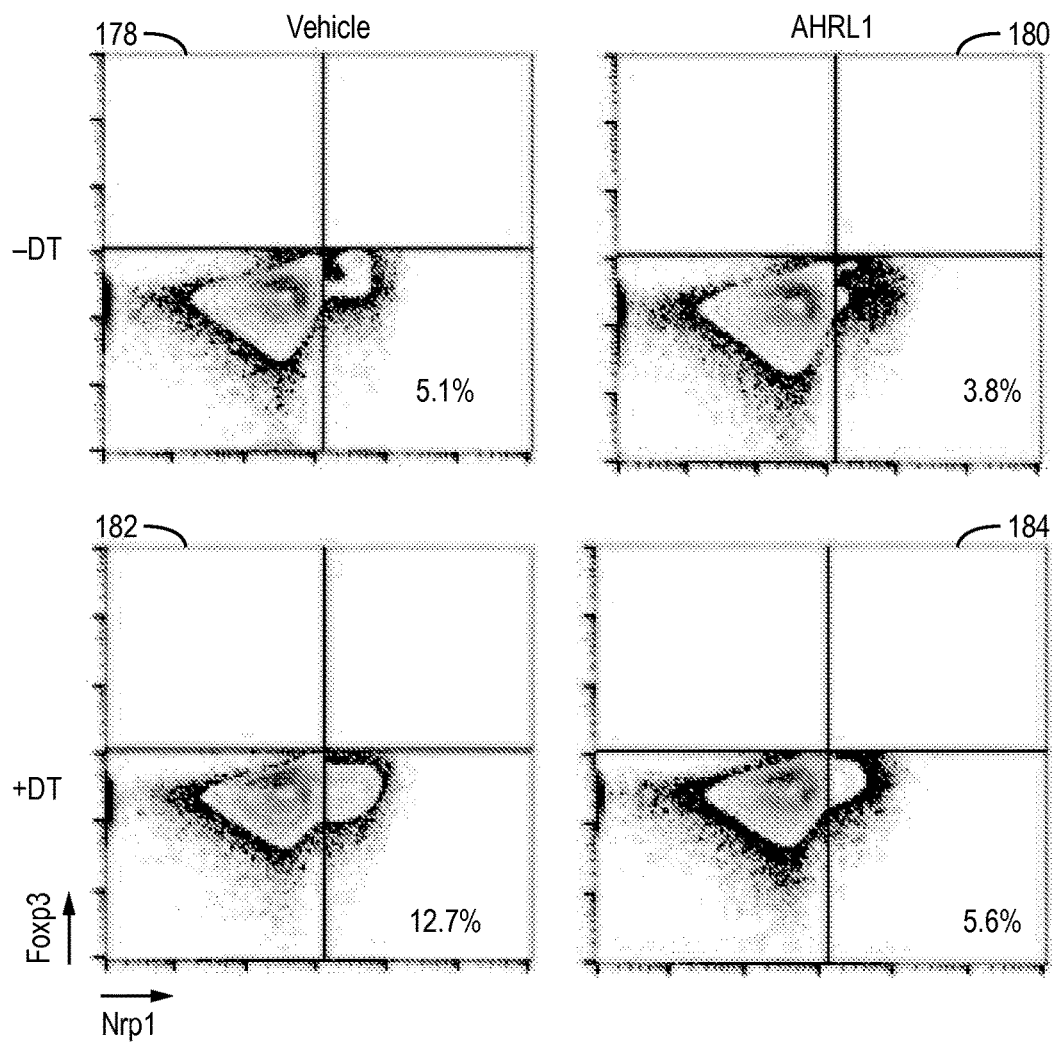
FIGS. 8a-8i illustrate treatment with an AhR ligand reduces disease-associated CD4+Nrp1+Foxp3− cells.
Figure 8B:
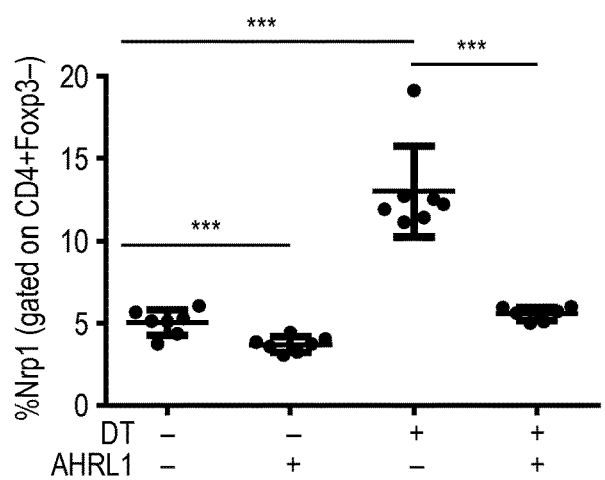

FIGS. 8a-8i illustrate AhR activation by AHRL1 inhibits the expression of disease associated CD4+Nrp1+Foxp3-retinoic acid receptor-related orphan receptor gamma t (RORγt+) cells. Nrp1 expression in CD4+Foxp3− cells is associated with an activated pathogenic effector T cell phenotype. Nrp1 expression in NOD.Foxp3− mice was analyzed to determine whether Nrp1 expression was altered by AhR activation. FIG. 8a shows histograms 178, 180, 182, and 184 illustrating Nrp1+ expression gated on CD4+ Foxp3− cells, i.e., the percentage of CD4+Foxp3-cells that were Nrp1+. In histograms 178, 180, 182, and 184, Foxp3 expression is shown along the y-axis, and Nrp1 expression is shown along the x-axis. Histogram 178 shows that 5.1% of CD4+Foxp3− cells in non-DT treated NOD.Foxp3$^{DTR}$ mice treated with vehicle were Nrp1+(i.e., 5.1% were in the bottom right quadrant). Histogram 180 shows that 3.8% of CD4+Foxp3− cells in non-DT treated NOD.Foxp3$^{DTR}$ mice treated with AHRL1 were Nrp1+(i.e., 3.8% were in the bottom right quadrant). Histogram 182 shows that 12.7% of CD4+Foxp3− cells in DT treated NOD.Foxp3$^{DTR}$ mice treated with vehicle were Nrp1+. Histogram 184 shows that 5.6% of CD4+Foxp3− cells in DT treated NOD.Foxp3$^{DTR}$ mice treated with AHRL1 were Nrp1+. FIG. 8b illustrates a plot of the data from FIG. 8a. Comparison of histograms 178 and 182 shows mice having a depleted CD4+Foxp3+ cell population (i.e., DT treated NOD.Foxp3$^{DTR}$ mice), had an increased percentage of CD4+Nrp1+Foxp3− cells as compared to mice not having a depleted CD4+Foxp3+ cell population (i.e., non-DT treated NOD.Foxp3$^{DTR}$ mice). Comparison of histograms 182 and 184 shows CD4+Foxp3+ depleted mice treated with AHRL1 had a decreased percentage of CD4+Nrp1+Foxp3− cells as compared to CD4+ Foxp3+ depleted mice treated with vehicle. FIGS. 8a and 8b indication treatment with AHRL1 can suppress accumulation of CD4+Nrp1+Foxp3− cells.

Figure 8C:
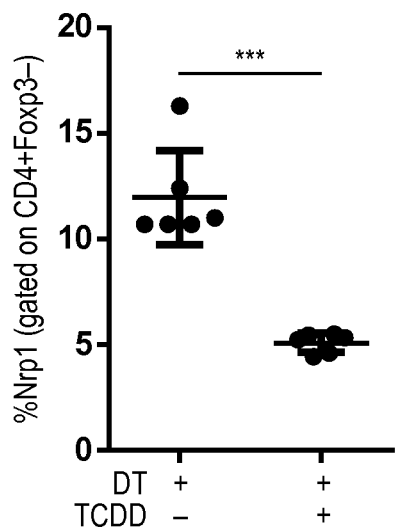

FIG. 8c compares the percentage of NRP1+ cells gated on CD4+Foxp3− cells in DT treated NOD.Foxp3DTR mice treated with TCDD to the percentage of NRP1+ cells gated on CD4+Foxp3− cells in DT treated NOD.Foxp3$^{DTR}$ mice not treated with vehicle. FIG. 8c shows treatment with TCDD decreased the percentage of CD4+Foxp3− cells expressing Nrp1+. FIGS. 8a-8c show treatment with an AhR ligand, e.g., AHRL1 or TCDD, can inhibit expression of CD4+Nrp1+Foxp3− cells in Foxp3 depleted mice.

Figure 8D:
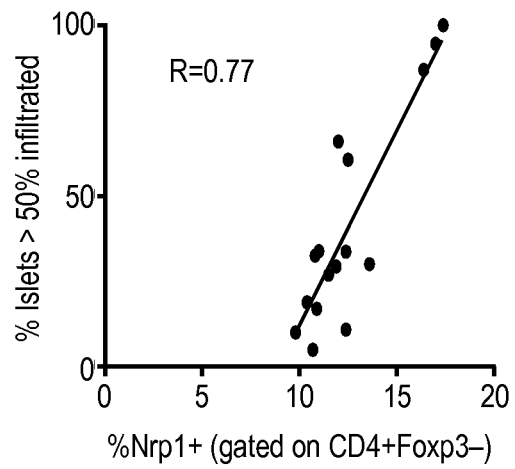

To test if CD4+Nrp1+Foxp3− cells correlated to development of a pathogenic effector T cell population (e.g., CTL) the percentage of CD4+Nrp1+Foxp3− cells was plotted versus the percentage of highly infiltrated islets (i.e., islet with ≥50% inflammatory CTL cell infiltration) for each of the vehicle treated NOD.Foxp3$^{DTR}$ mice injected with DT. FIG. 8d shows the percentage of highly infiltrated islets increased as the percentage of CD4+Foxp3− cells expressing NRP1 increased. FIG. 8d shows increased percentage of CD4+Nrp1+Foxp3− cells correlates with an increase in disease severity, i.e., an increased percentage of highly infiltrated islets. The correlation between increased proportions of CD4+Nrp1+Foxp3-cells and disease severity suggests that CD4+Nrp1+Foxp3− cells are associated with the development of pathogenic T cell populations.

The decrease in percentage of CD4+Nrp1+Foxp3− cells observed in both AHRL1 treated Foxp3 depleted mice and TCDD treated Foxp3 depleted mice as compared to vehicle treated Foxp3 depleted mice further demonstrates treatment with an AhR ligand can suppress the percentage of CD4+ Nrp1+Foxp3− cells, which, as shown in FIG. 8d, directly correlates to islet infiltration. The decrease in percentage of CD4+Nrp1+Foxp3− cells observed in both AHRL1 treated and TCDD treated Foxp3 depleted mice as compared to vehicle treated Foxp3 depleted mice further demonstrates treatment with an AhR ligand can suppress islet infiltration independently from, and in the absence of, CD4+Foxp3+ Tregs. The ability to prevent islet infiltration independently from CD4+Foxp3+ Tregs indicates AhR activation by AHRL1, TCDD, and other AhR ligands suppresses effector CTL cell populations independently of Treg induction.

Figure 8E:
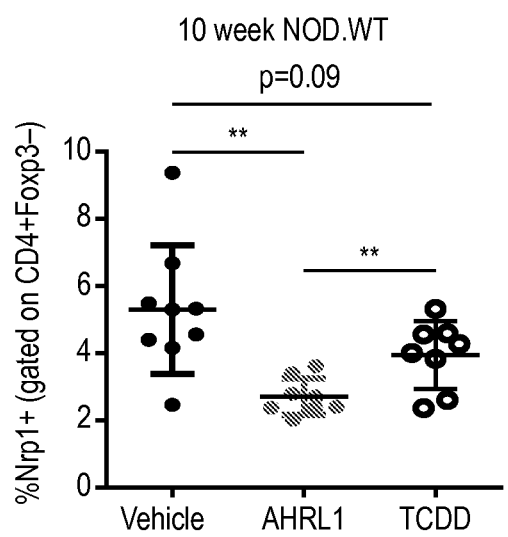

FIG. 8e compares the percentage of CD4+Foxp3− cells that were Nrp1+ in vehicle treated, AHRL1 treated, and TCDD treated NOD.Foxp3$^{WT}$ mice at 20 weeks of age. The lower percentage of CD4+Nrp1+Foxp3− cells in AHRL1 treated mice as compared to TCDD treated mice illustrates a higher efficacy of AHRL1 to suppress islet infiltration. The decrease in percentage of CD4+Nrp1+Foxp3− cells observed in both AHRL1 treated and TCDD treated mice as compared to vehicle treated mice further demonstrates treatment with an AhR ligand can suppress the percentage of CD4+Nrp1+Foxp3− cells, which, as shown in FIG. 8d, directly correlates to disease severity and islet infiltration.

Figure 8F:
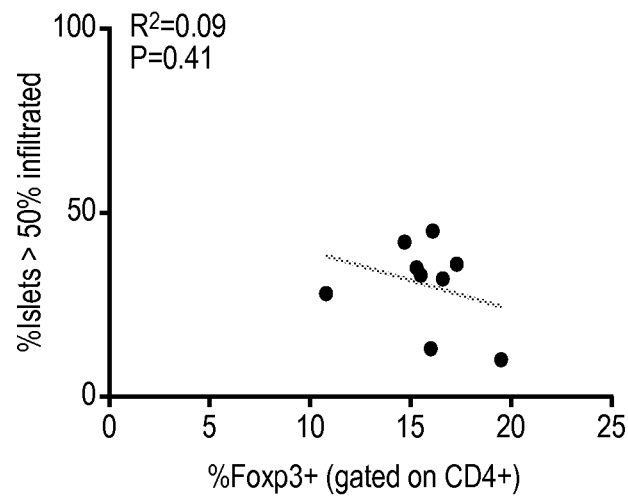

FIG. 8f compares percentage of Foxp3+ cells gated on CD4+ cells to the percentage of islets having greater than 50% infiltration. FIG. 8f shows that as the percentage of CD4+Foxp3+ cells increased the percentage of islets having greater than 50% infiltration decreased. FIG. 8f illustrates increased percentage of CD4+Foxp3+ cells did not correlate with increased severity of insulitis.

T helper 17 (Th17) cells have been shown to play a detrimental role in exacerbating TIDM. RORγt is a transcription factor for Th17 cells. Co-expression of RORγt with CD4+Nrp1+Foxp3− cells was assessed to illustrate if AhR activation inhibits the induction of Th17 cells.

Figure 8G:
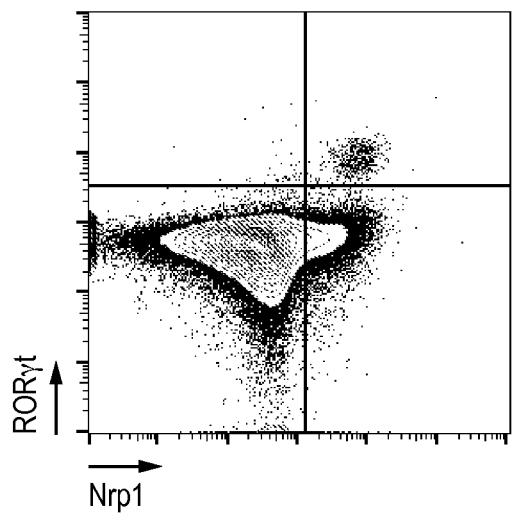

FIG. 8g shows a histogram comparing the expression of Nrp1 and of RORγt in CD4+Foxp3− cells. The y-axis represents RORγt expression and x-axis represents Nrp1 expression. The lack of cells in the upper left quadrant of FIG. 8g indicates all CD4+Foxp3− cells that expressed RORγt+ also expressed Nrp1. The co-expression of RORγt and Nrp1 in all CD4+Foxp3− cells further indicates CD4+ NRp1+Foxp3− cells represent a pathogenic effector T cell population.

Figure 8H:
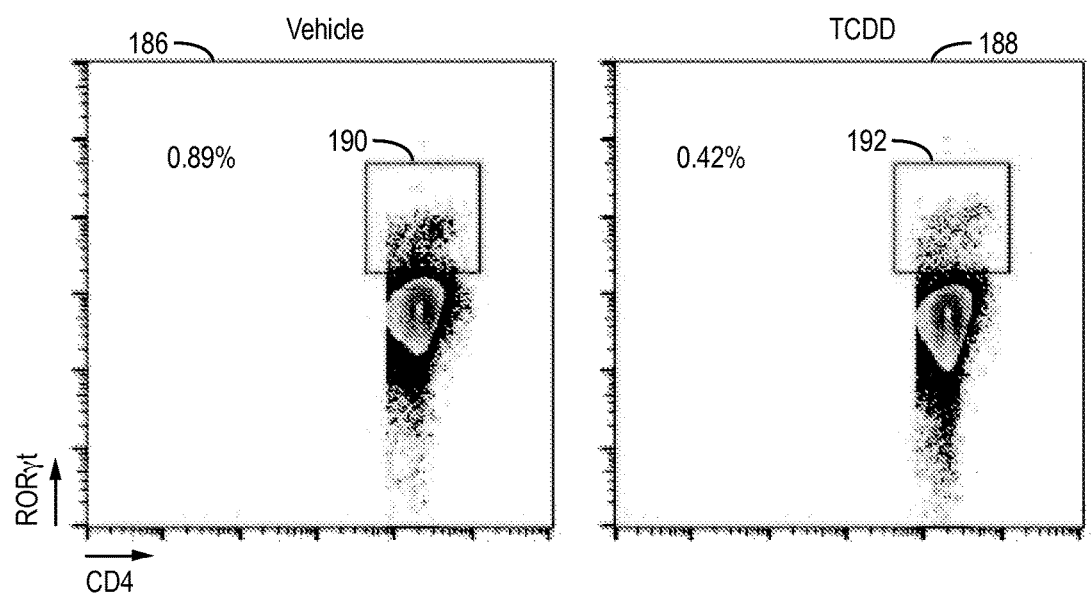
Figure 8I:
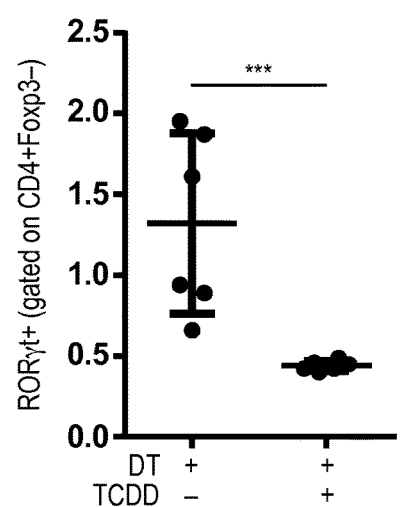
Figure 9A:
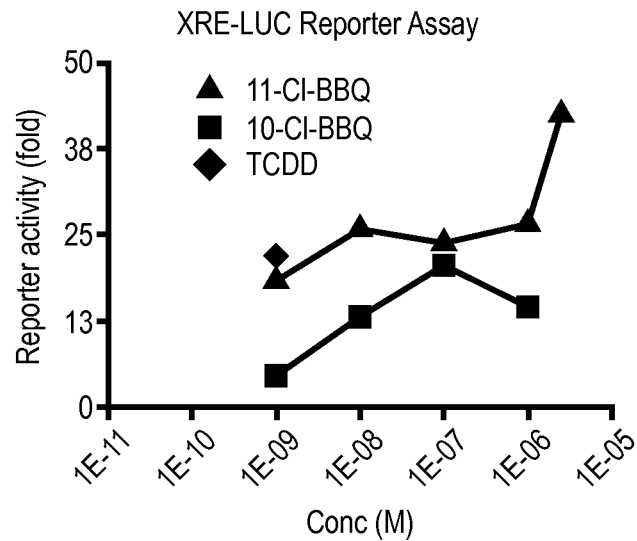
FIGS. 9a-9f illustrate results of activity studies showing 10-Cl-BBQ, 11-Cl-BBQ, and combinations thereof activates AhR.
Figure 9B:
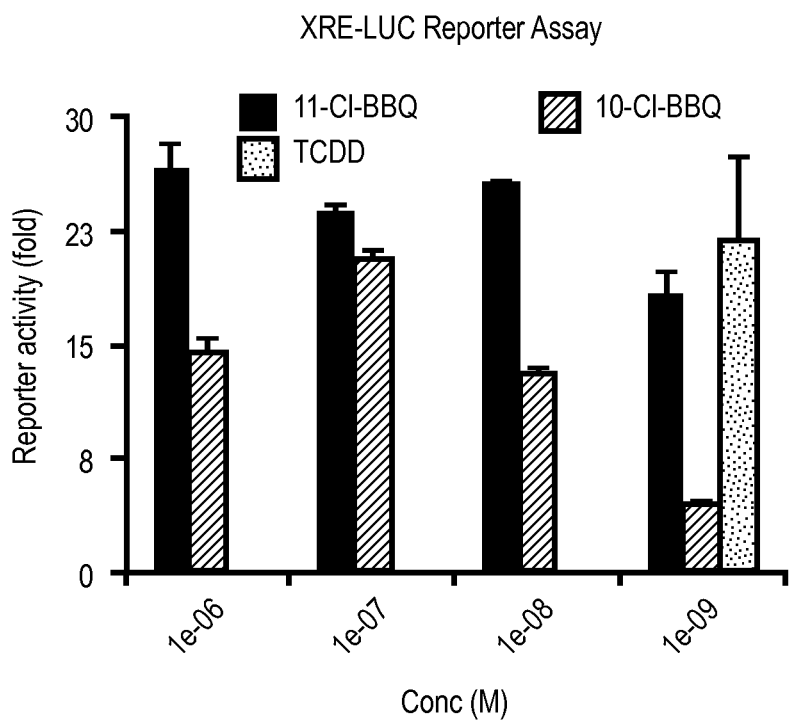
Figure 9C:
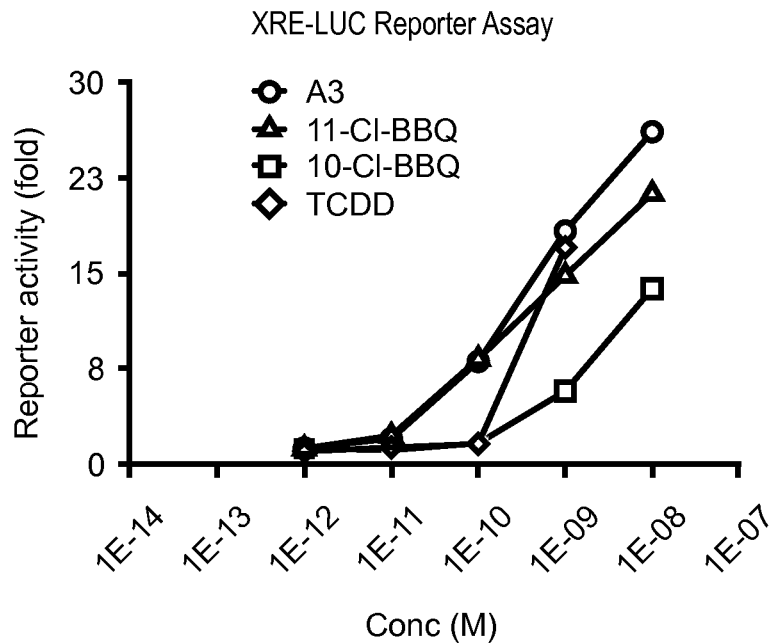
Figure 9D:
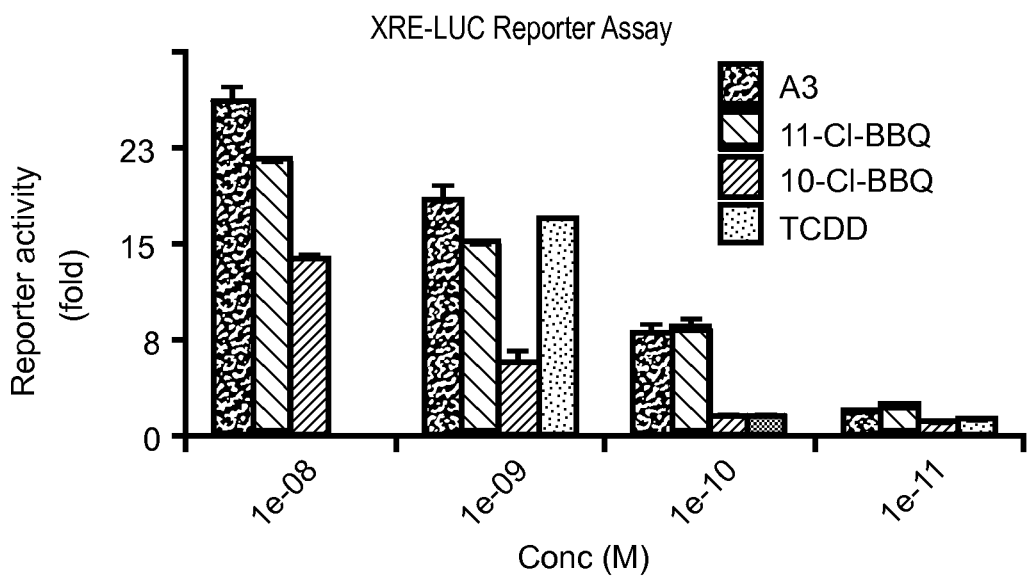
Figure 9E:
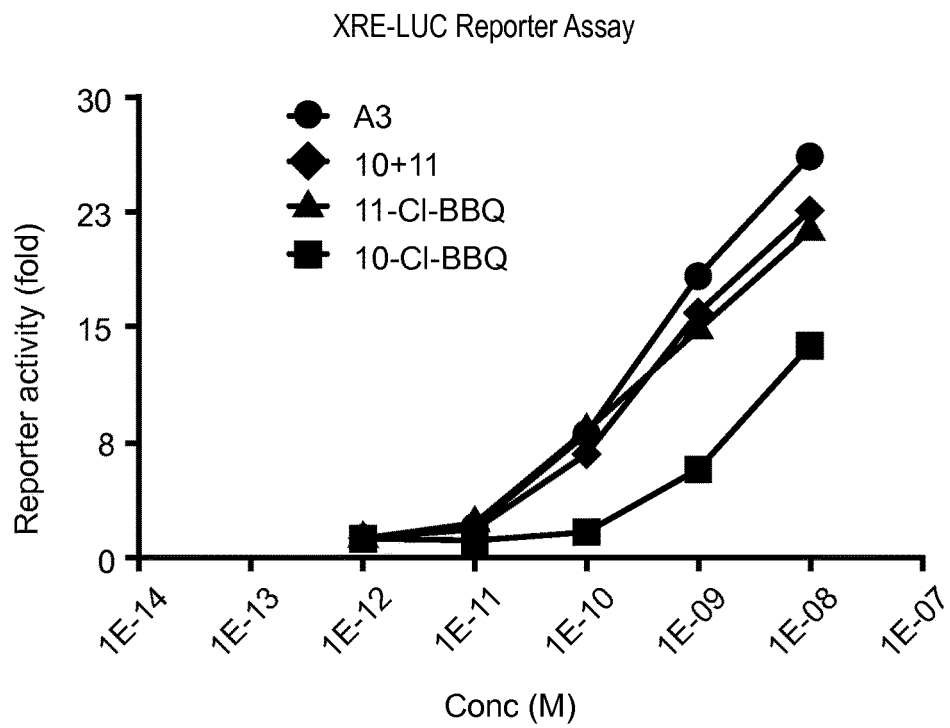
Figure 9F:
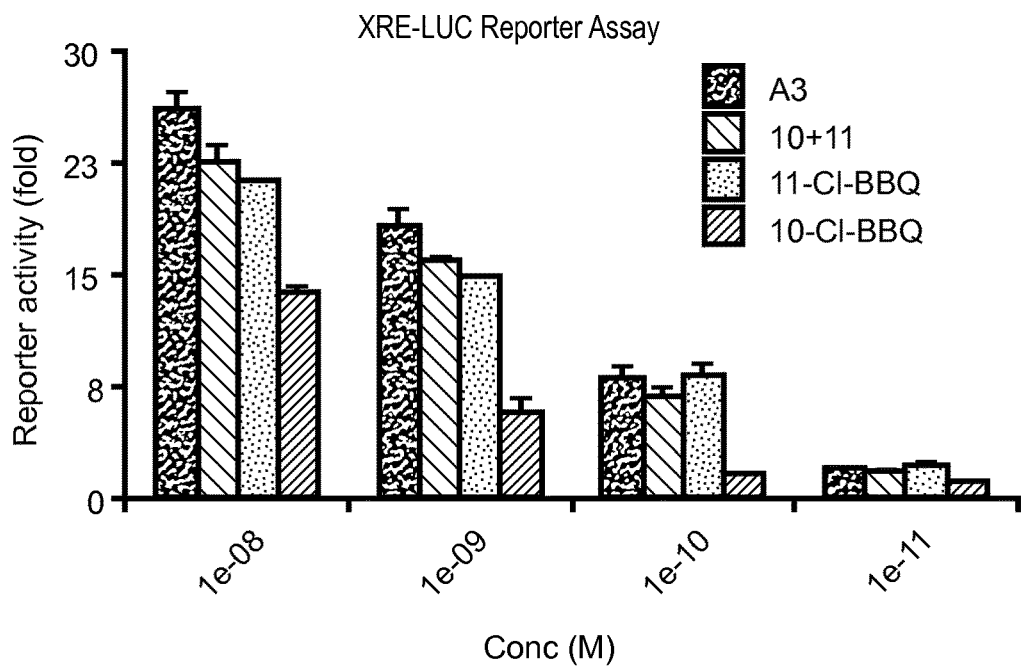

FIG. 8h illustrates two histograms 186 and 188 showing the percentages of CD4+Foxp3− cells that were RORγt positive (RORγt+) in vehicle treated mice (histogram 186) to TCDD treated mice (histogram 188). Rectangular region 190 in histogram 186 shows 0.89% of CD4+Foxp3− cells in vehicle treated mice were RORγt+. Rectangular region 192 in histogram 188 shows 0.42% of CD4+Foxp3− cells in TCDD treated mice were RORγt+. FIG. 8i illustrates a plot of the percentages of CD4+RORγt+Foxp3− cells from FIG. 8h. FIGS. 8h and 8i demonstrate treatment with TCDD, and thus AhR activation, results in a reduction in the percentage of CD4+Foxp3− cells expressing RORγt.

The reduction in percentage of CD4+Nrp1+Foxp3− cells and percentage of CD4+RORγt+Foxp3− cells in AhR ligand treated mice as compared to vehicle treated mice demonstrates AhR activation is capable of mediating the suppression of pathogenic RORγt+ expressing cells independently of Foxp3+ Tregs.

The therapeutic response and reduction of islet infiltration in Foxp3 deficient mice treated with AHRL1 and TCDD demonstrate a reduction in CTL cells is the primary event in AhR-driven suppression of insulitis. The ability of AHRL1 and TCDD to reduce Nrp1 expression in CD4+Foxp3− cells and the correlation between Nrp1 expression in CD4+ Foxp3− cells and increased islet infiltration, demonstrates treatment with AhR ligands can suppress insulitis in a subject that is Foxp3+ Treg deficient. Further, correlation between severity of islet infiltration and expression of CD4+ Nrp1+Foxp3− cells may have utility as a biomarker for the extent of islet infiltration in the pancreas. Both AHRL1 treatment and TCDD treatment reduced the percentage of CD4+Foxp3− cells expressing NRP1+, which directly correlated with reduced islet infiltration.

Functionally, Nrp1 is expressed in the immunological synapse and has been implicated in productive signaling between T cells and dendritic cells (DCs). A decrease in Nrp1 expression following treatment with AhR ligands can alter crosstalk between T cells and DCs. Altering crosstalk between T cells and DCs can lead to impairment in T cell differentiation and preclusion of CTL accumulation. Accordingly, treatment with AhR ligands, for example, AHRL1, 11-Cl-BBQ, 10-Cl-BBQ, an 11-Cl-BBQ analog, or combinations thereof, can be employed to alter T cell differentiation and preclude CTL accumulation. Treatments of autoimmune disease by activating AhR to alter T cell differentiation and suppress CTL development independent of Foxp3+ Treg induction provides an alternative treatment strategy to previous therapies that only attempted to induce Foxp3+ Tregs. Accordingly, treatment with AhR ligands, for example, AHRL1, 11-Cl-BBQ, 10-Cl-BBQ, an 11-Cl-BBQ analog, or combinations thereof, provides a useful therapeutic strategy in the treatment of autoimmune diseases, particularly diseases characterized by an increased CTL cell population and/or by a defective Foxp3+ Treg cell population.

FIGS. 9a-9f illustrate activity studies for 10-Cl-BBQ, 11-Cl-BBQ, and combinations thereof. Hepa-1 cells expressing endogenous AhR were transfected with a xenobiotic responsive element (XRE)-luciferase reporter gene. The transfected cells were treated with indicated concentrations of 11-Cl-BBQ, 10-Cl-BBQ, TCDD, a mixture of approximately 60% 11-Cl-BBQ, 40% 10-Cl-BBQ (A3), or a mixture of approximately 50% 11-Cl-BBQ, 50% 10-Cl-BBQ (10+11). The activity was measured 16 hours after treating the cells with the various concentrations. The mean luciferase activity is shown with standard error of the mean (SEM).

The activity studies shown in FIGS. 9a-9f demonstrate 10-Cl-BBQ, 11-Cl-BBQ, and combinations thereof activate AhR. FIGS. 9a-9f further illustrate 11-Cl-BBQ and compounds including 11-Cl-BBQ produced increased AhR reporter activity as compared to 10-Cl-BBQ alone at the same concentration. Increase in reporter activity correlates with an increase of cells showing AhR activation. Increases in the AhR activation efficacy of 11-Cl-BBQ and mixtures containing 11-Cl-BBQ indicate 11-Cl-BBQ maybe therapeutically effective at lower doses than 10-Cl-BBQ.

Figure 10A:
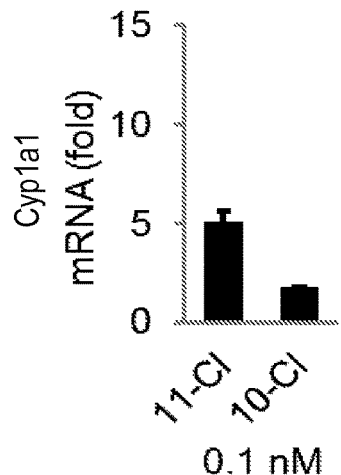
FIGS. 10a-10c compare increases in expression levels of CYP1A1 in Hepa-1 cells after treatment with 10-Cl-BBQ or 11-Cl-BBQ.
Figure 10B:
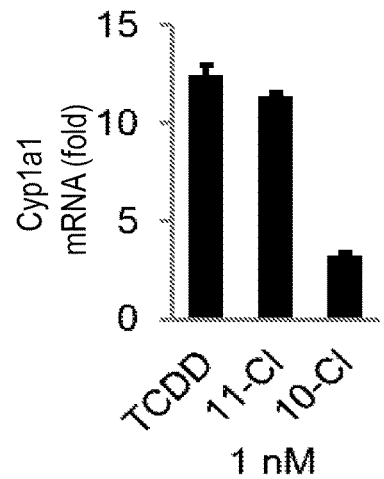
Figure 10C:
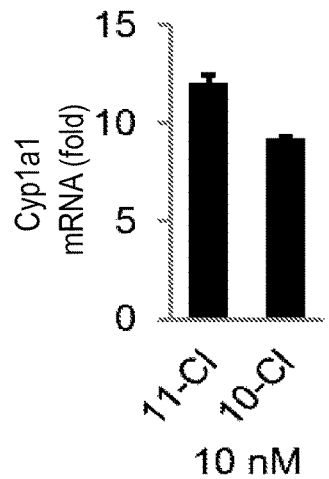

FIGS. 10a-10c illustrate induction of expression of CYP1A1 gene by 10-Cl-BBQ and 11-Cl-BBQ in Hepa-1 cells. The levels of CYP1A1 expression were determined by measuring CYP1A1 messenger ribonucleic acid (mRNA) levels. FIG. 10b shows treatment with 11-Cl-BBQ and TCDD produced a comparable level of induction at a 1 nanomolar (nM) concentration. FIG. 10c shows at 10 nM, 11-Cl-BBQ was saturated and had a similar activity as 10-Cl-BBQ. FIG. 10a shows at 0.1 nM, 11-Cl-BBQ was still active while 10-Cl-BBQ had little activity. FIGS. 10a-10c indicate AhR is activated by both 10-Cl-BBQ and 11-Cl-BBQ, but 11-Cl-BBQ may be therapeutically effective at lower doses than 10-Cl-BBQ.

Figure 11A:
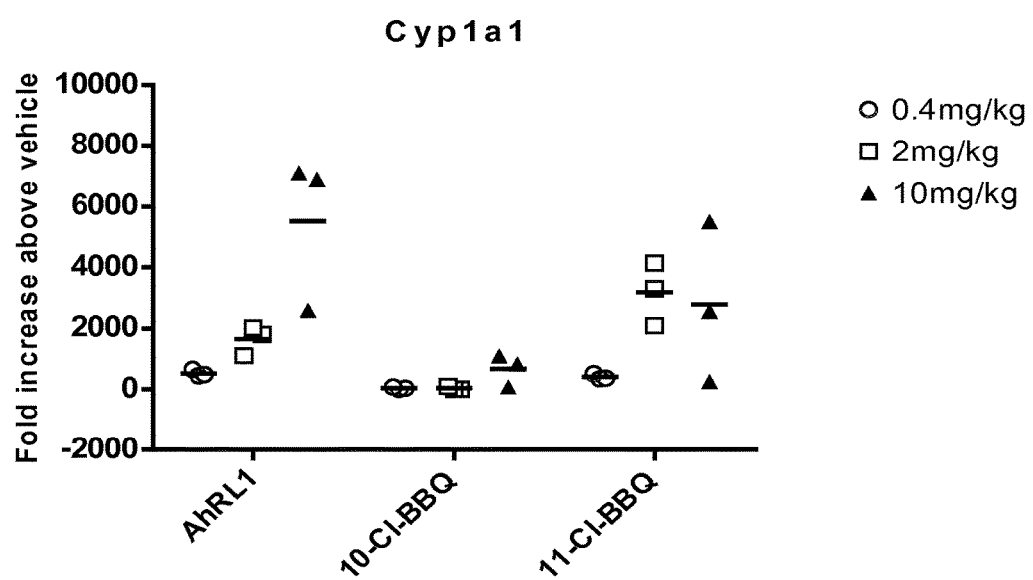
FIGS. 11a-11d compare CYP1A1 expression at varying doses of 10-Cl-BBQ, 11-Cl-BBQ, and AHRL1.
Figure 11B:
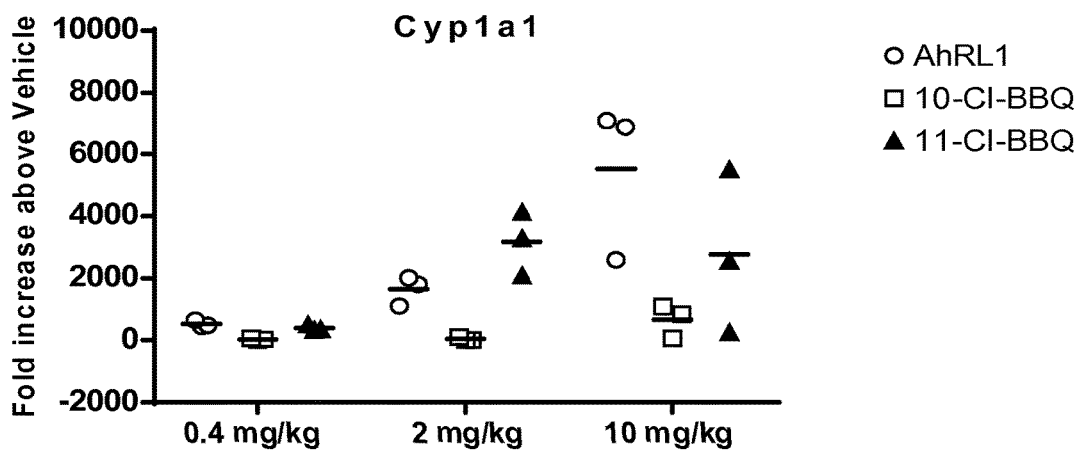

FIGS. 11a-11d illustrate results of a dosing study. FIGS. 11a and 11b illustrate results of a study determining AhR activation at various doses of 10-Cl-BBQ, 11-Cl-BBQ, and AHRL1. 27 mice were split into 3 groups with 3 doses per group, sample sizes of n=3 mice per group were used. 10 mg/kg, 2 mg/kg, or 0.4 mg/kg of AHRL1 (i.e., compound having a mixture of approximately 60% 11-Cl-BBQ, 40% 10-Cl-BBQ) was administrated to a first group of mice. 10 mg/kg, 2 mg/kg, or 0.4 mg/kg of 10-Cl-BBQ was administered to a second group of mice. 10 mg/kg, 2 mg/kg, or 0.4 mg/kg of 11-Cl-BBQ was administer to a third group. Liver samples were taken 20 hours post injection to determine the optimal dose and isomer using CYP1A1 mRNA induction as a readout.

FIGS. 11a and 11b show AhRL1 and 10-Cl-BBQ produced different levels of CYP1A1 expression at all doses. AHRL1 did not produce a significantly different level of CYP1A1 expression as compared to 11-Cl-BBQ at any dose. 10-Cl-BBQ and 11-Cl-BBQ produced different levels of CYP1A1 at 0.4 mg/kg and 2 mg/kg.

Figure 11C:
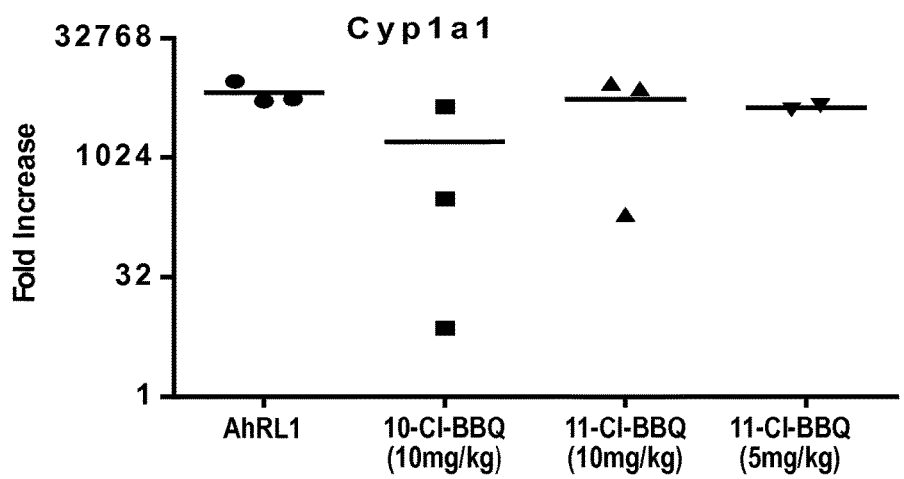
Figure 11D:
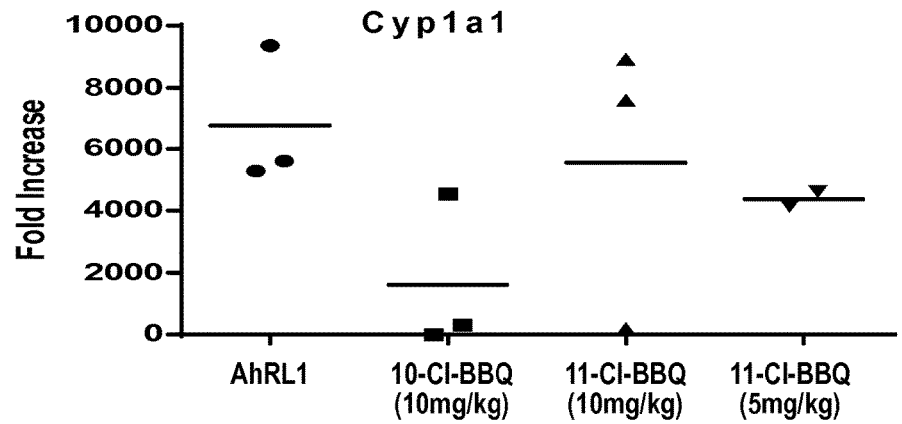

FIGS. 11c and 11d illustrate results of a dosing study using 10 mg/kg of AhRL1, 10 mg/kg 10-Cl-BBQ, 10 mg/kg 11-Cl-BBQ, or 5 mg/kg 11-Cl-BBQ. The mice were sacrificed and liver snips were obtained 20 hours post-injection to determine the optimal dose and isomer using CYP1A1 induction as a readout. FIGS. 11a-11d illustrate that 10-Cl-BBQ, 11-Cl-BBQ, and AHRL1 are each capable of activating AhR, however 11-Cl-BBQ can increases AhR activation at lower doses as compared to 10-Cl-BBQ and AHRL1.

FIGS. 9a-9f, 10a-10c, and 11a-11d illustrate the affinity of 11-Cl-BBQ, 10-Cl-BBQ, and combinations thereof for AhR. The ability 11-Cl-BBQ, 10-Cl-BBQ, and combinations thereof to increase and maintain AhR activation indicates substituted BBQ molecules, e.g., 11-Cl-BBQ, 10-Cl-BBQ, analogs 2-6 in Table 2, or a BBQ molecule having a substitution other than or in addition to 11-chloro, will be effective in the treatment of autoimmune disease. For example, in one embodiment the present invention treats autoimmune disease by administering a BBQ molecule (i.e., analog 1 listed in Table 1 and illustrated in FIG. 15a) including one or more Fluorine (F), Cl, or bromine (Br) substitutions.

The therapeutic potential of AHRL1, 11-Cl-BBQ, 10-Cl-BBQ, an 11-Cl-BBQ analog, or combinations thereof as a therapeutic for treatment of autoimmune disease is further evidences by the activation of AhR by AHRL1 inducing AhR-dependent Tregs. AHRL1 was selected based on small molecule screening for ligands of the AhR that induce AhR-dependent Tregs. Certain AhR ligands induce Treg cells that require AhR expression in CD4+ T cells. AHRL1 activates the AhR in alloantigen-responsive T cells which induces AhR-dependent Tregs. AhR-dependent Tregs are a phenotype identified during initial activation and expansion of the naïve allospecific CD4+ T cells and are characterized by high expression of CD25, CTLA-4, and several other molecules associated with regulatory T cells, but not Foxp3. Thus, AhR is a unique transcription factor driving Treg development. AhR-Tregs showed potent suppression of naïve and allogeneic T cell proliferation in vitro. The induction of AhR-Tregs suppresses the development of effector CTL in vivo, thereby suppressing the development of CTL that attack host cells in GVHD or β cells in the pancreas in T1DM.

Figure 12A:
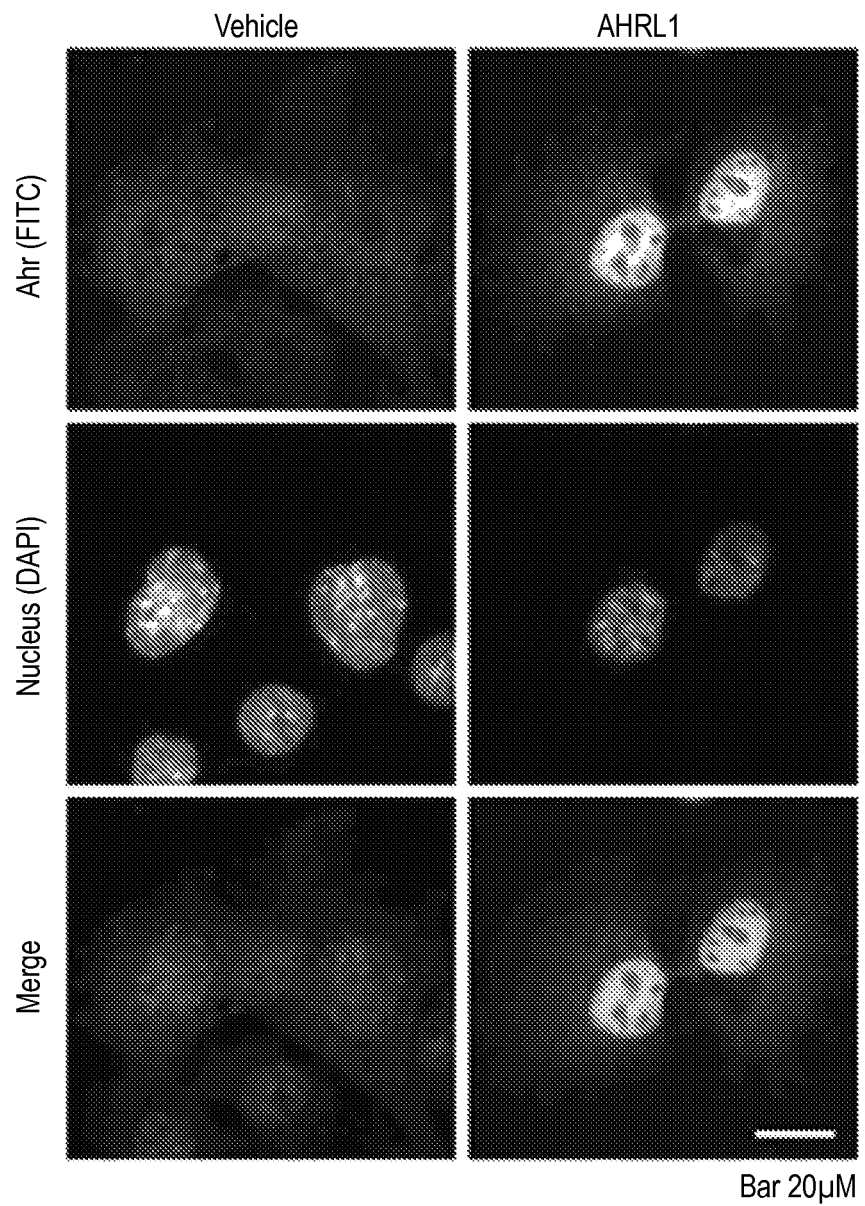
FIGS. 12a-12f illustrate results indicating that AHRL1 is a potent AhR ligand.
Figure 12B:
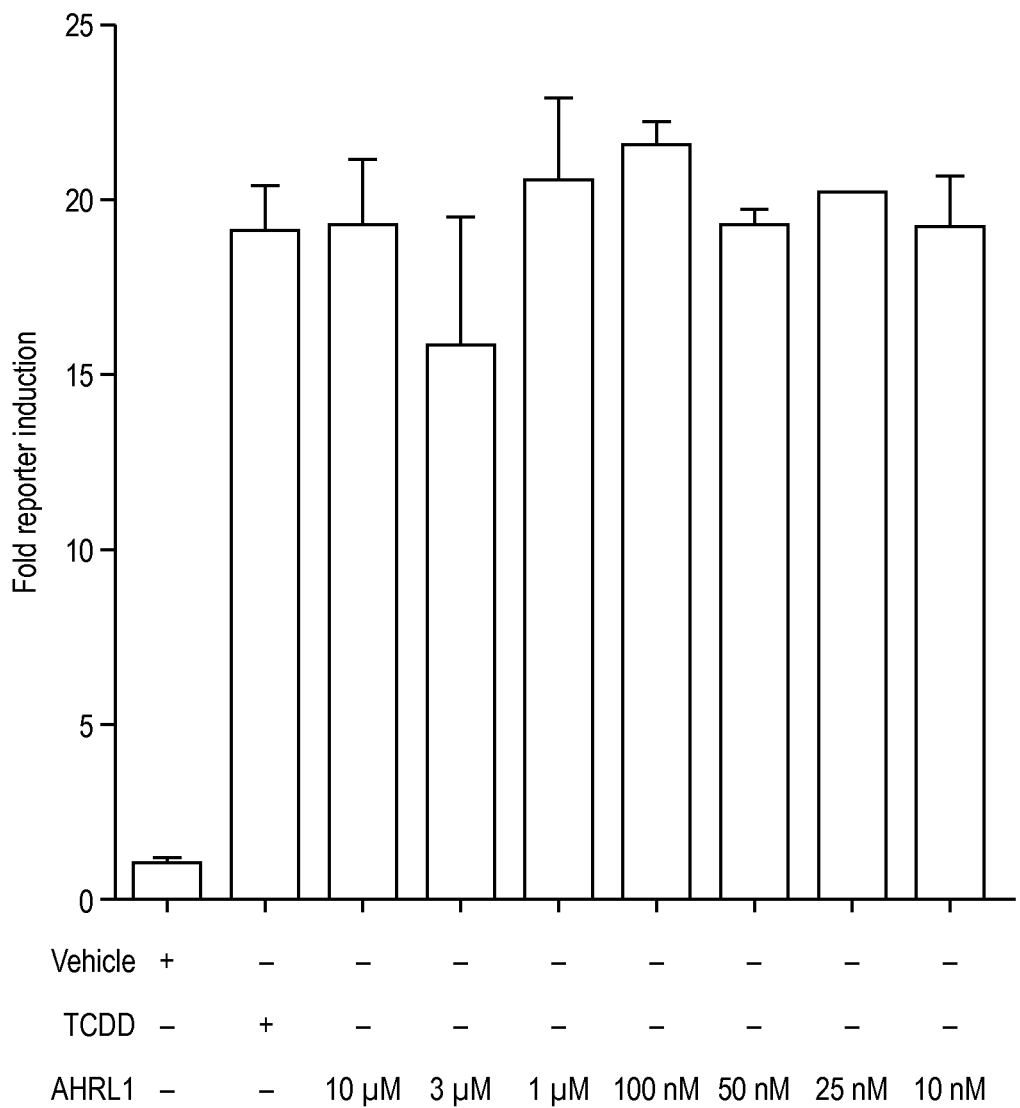

FIGS. 12a-12f show results indicating that AHRL1 is a potent AhR ligand. AHRL1 is comprised of high-affinity AhR ligands 10-Cl-BBQ and 11-Cl-BBQ. AHRL1 activates the AhR by binding to AhR and inducing a transcriptionally-active conformation of AhR. AHRL1 promotes cytosol to nuclear translocation of AhR and activates the AhR-regulated reporter gene at nM concentrations. FIG. 12a shows that 10 nM AHRL1 promoted cytosol to nuclear translocation of AhR after a 1 hour treatment of Hepa-1 cells. FIG. 12b shows Hepa-1 cells expressing endogenous AhR were transfected with an AhR-regulated luciferase reporter gene, specifically, XRE-mouse mammary tumor virus (MMTV)

promoter-luciferase (Luc) or XRE-MMTVpromoter-Luc. The reporter gene activity was measured after 12 hours of treatment with TCDD at a concentration of 1 nM or with the indicated concentrations of AHRL1.

Figure 12C:
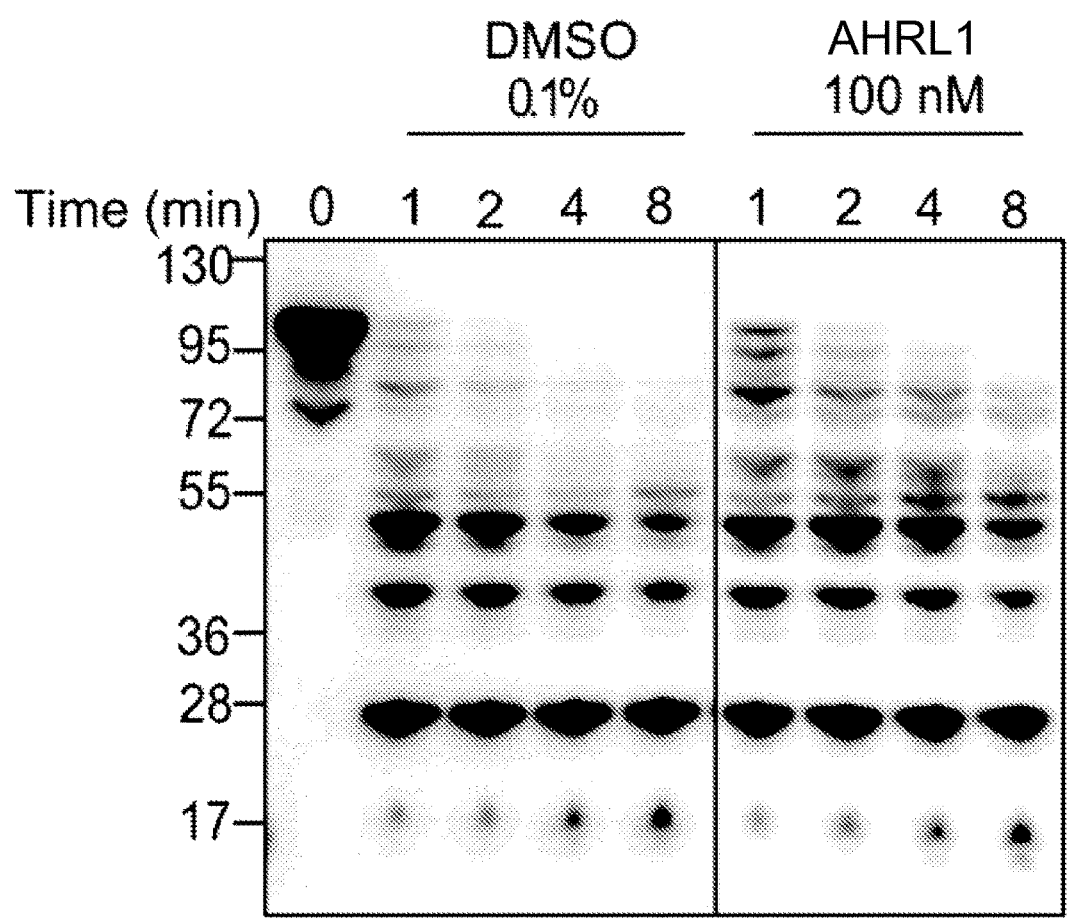
Figure 12D:
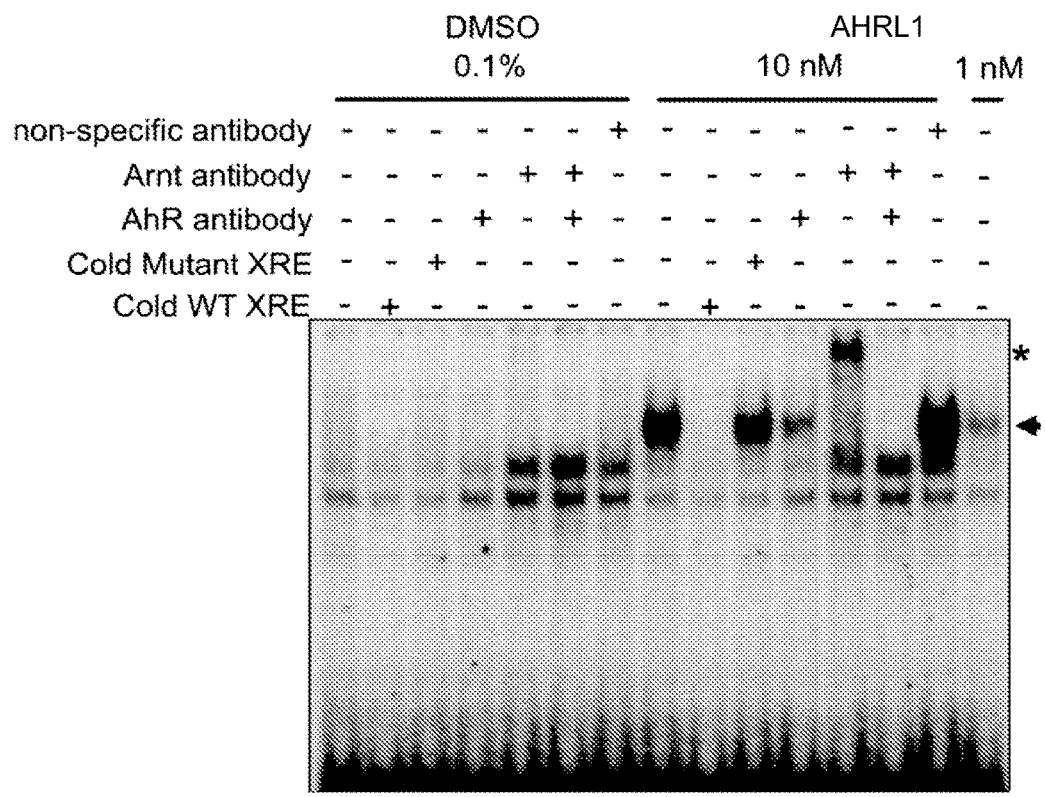

AHRL1 induces deoxyribonucleic acid (DNA) binding of AhR and delays proteolysis of AhR. FIG. 12c shows alteration in the proteolytic pattern of AhR by AHRL1. Whole cell lysate, 45 micrograms (μg) of protein, from mouse hepatoma Hepa1c1c7 cells was incubated with 100 nM AHRL1 or 0.1% DMSO vehicle for 1 hour at room temperature and proteolyzed by 1 microgram per milliliter (μg/ml) subtilisin for 1, 2, 4, and 8 minutes (min) at room temperature. Proteolytic cleavage products of AhR were analyzed by immunoblot. FIG. 12d illustrates an electrophoretic mobility shift assay showing the ligand-stimulated binding of AhR to XRE. Whole cell lysate (18 μg of protein) from mouse hepatoma Hepa1c1c7 cells was incubated with 10 nM AHRL1 or 0.1% DMSO for 2 hours at room temperature and 32P-labeled oligonucleotide containing XRE for 20 min at room temperature. The samples were electrophoresed on a native polyacrylamide gel and the signal was visualized by a phosphorimager. Unlabeled competitor XRE or antibody (Ab) against AhR or AhR nuclear translocator (Arnt) was co-incubated with 32P-labeled oligonucleotide. The arrow indicates specific signal and asterisk (*) shows the supershifted complex.

Figure 12E:
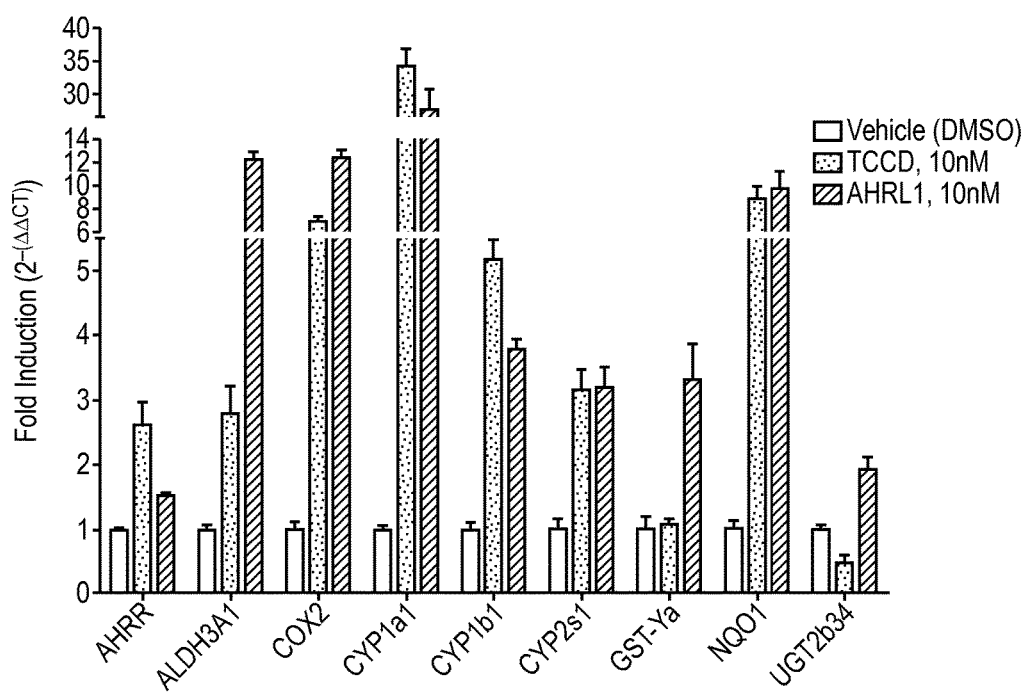

FIG. 12e shows that AHRL1 induces the expression of AhR target genes. Hepa-1 cells were treated with AHRL1 (10 nM), TCDD (10 nM), or vehicle (DMSO) for eight hours. RNA was extracted and real-time reverse transcription polymerase chain reaction (RT-qPCR) was performed for a select set of AhR target genes: aryl hydrocarbon receptor repressor (AHRR); aldehyde dehydrogenase family 3, subfamily A1 (ALDH3A1), cytochrome P450 1B1 (CYP1B1); glutathione S-transferase, mu 3 (Gstm3); glutathione S transferase (GST-Ya); alpha 1, NAD(P)H dehydrogenase quinone 1 (NQO1); UDP glucuronosyltransferase 2 family, polypeptide B34 (UGT2b34).

Figure 12F:
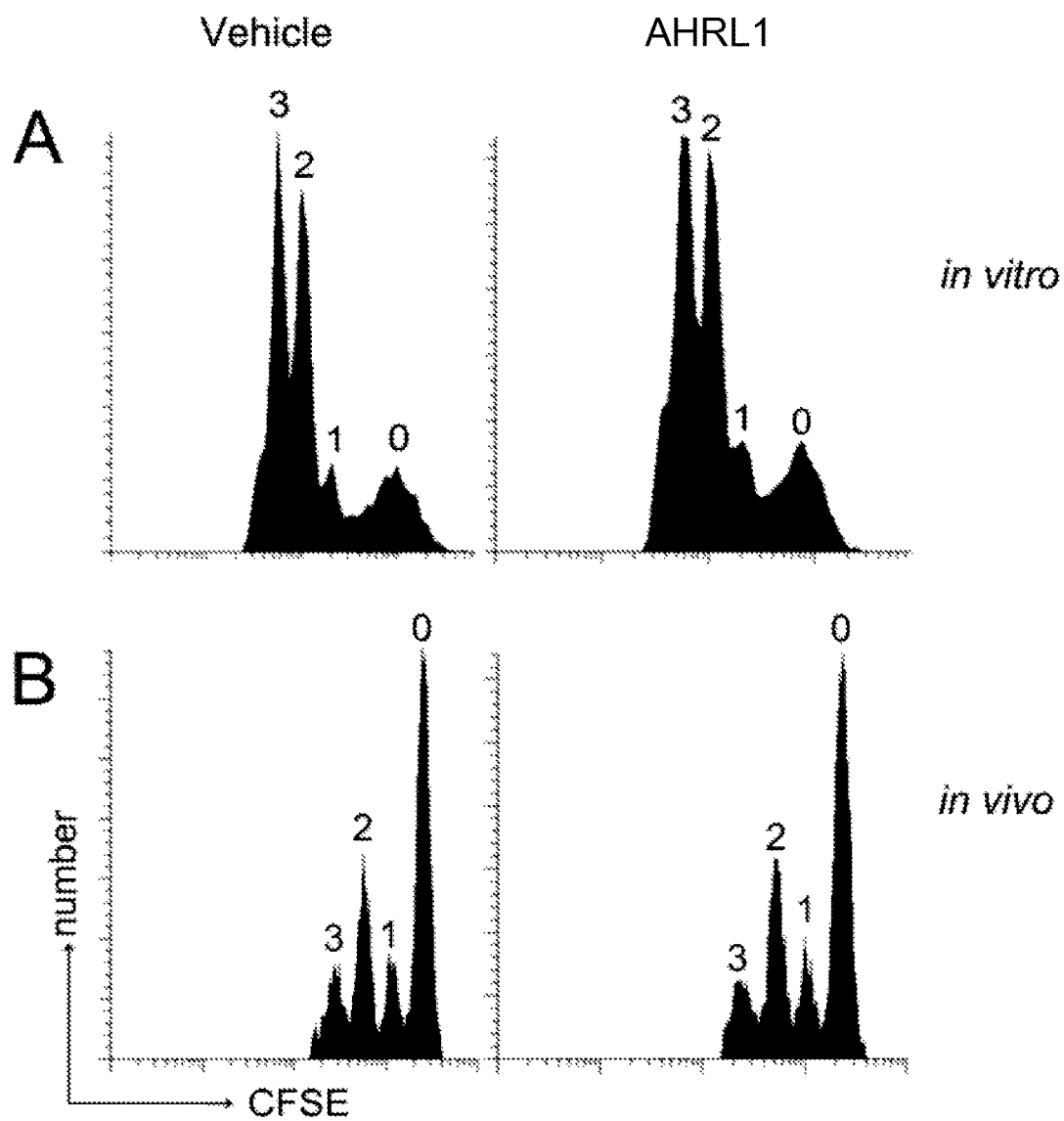

FIG. 12f shows AHRL1 does not inhibit T cell proliferation in vitro or in vivo. In vitro, splenocytes from C57BL/6 mice were labeled with 5-(and 6)-Carboxyfluorescein diacetate succinimidyl ester (CFSE) and activated in vitro with anti-CD3 and anti-CD28 in the presence of 100 nM AHRL1 or DMSO for 72 hours. In vivo, C57BL/6 donor T cells were labeled with CFSE and injected into B6D2F1 host mice. A sample size of n=5 per group of host mice were treated with 10 milligram per kilogram per day (mg/kg/d) vehicle or 10 mg/kg/d of AHRL1 intraperitoneal (i.p.) for two days. Donor cells were identified by gating on CD4+CFSE+ cells. Dilution of CFSE fluorescence demonstrates division of CD4+ T cells. The absence of anti-proliferative effects of AHRL1 toward antigen-responding CD4+ T cells is a key factor for the induction of AhR-Tregs.

Overall, the results in FIGS. 12a-12f indicate that AHRL1 is a high-affinity ligand and potent activator of the AhR and is non-cytotoxic to proliferating T cells. AhR-dependent Tregs are induced by AHRL1 and block the differentiation of effector CTL resulting in suppression of GVHD and autoimmune destruction of pancreatic β-cells. AHRL1 inducing AhR-dependent Tregs indicated AHRL1, 11-Cl-BBQ, 10-Cl-BBQ, an 11-Cl-BBQ analog, or combinations thereof can be used to activate AhR and treat immune-mediated diseases without inducing global immune suppression associated with many current therapies.

Figure 13A:
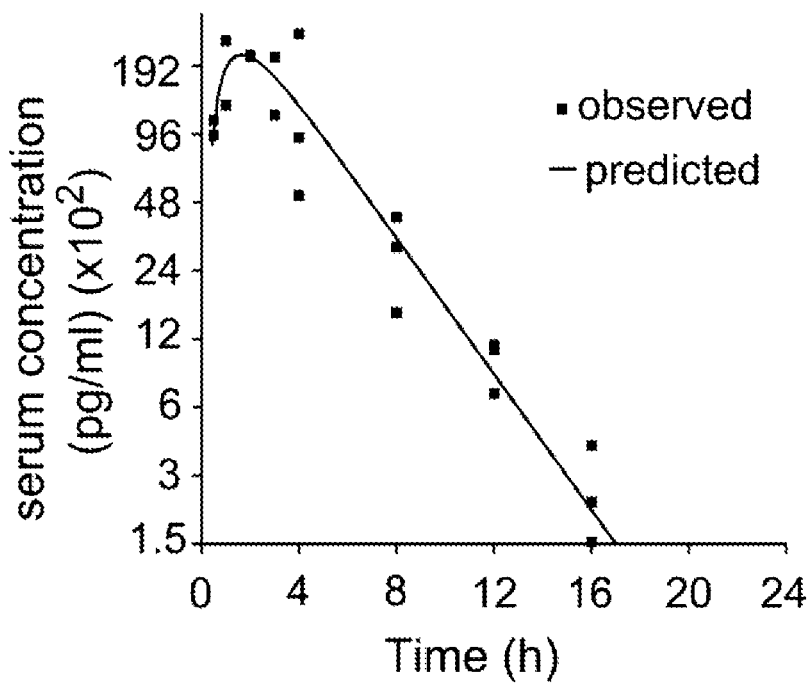
FIGS. 13a-13b illustrate the pharmacokinetics of AHRL1.
Figure 13B:
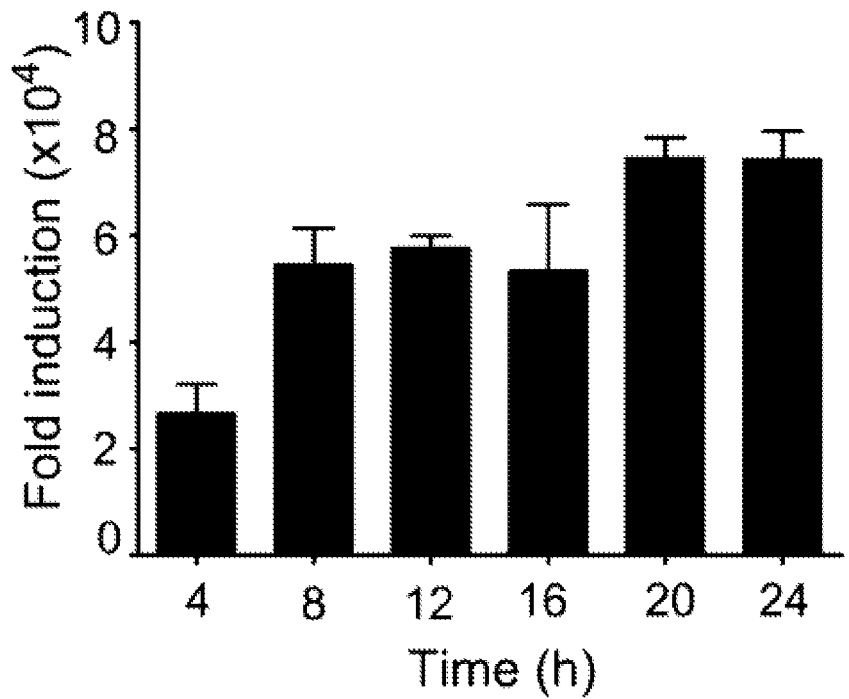

FIGS. 13a and 13b show the pharmacokinetics of AHRL1. To determine the half-life of AHRL1, mice were treated with a single intraperitoneal injection of the chemical, and serum concentrations were measured over time by mass spectrometry. In FIG. 13a, C57BL/6 mice were given 10 mg/kg AHRL1 by i.p. injection. Blood was collected at the indicated times by cardiac puncture. The blood serum was processed to remove protein and the samples were analyzed by QTRAP 4000 LC/MS/MS. The blood serum concentration of AHRL1 was determined from a standard curve based on known concentrations of AHRL1.

As shown in FIG. 13a, the data fits a one compartment model with first-order kinetics. Based on the model, the serum half-life of AHRL1 is approximately 2 hours. Additional kinetic parameters include the absorption rate constant ($k_a$) which was 1.2 $h^{-1}$. The maximum concentration reached in serum ($C_{max}$) was 21.51 μg per liter (L), and the time required to reach $C_{max}$ ($T_{max}$) was 1.64 hours (h). The area under the concentration-time curve ($AUC_{0-\infty}$) was 102.5 mg/L*h. The volume of distribution/bioavailability (V/F) and total clearance/bioavailability (CL/F) constants were 5.66 L and 32.5 mL/min respectively.

To assess the duration of activation of AhR in response to a single AHRL1 treatment, the temporal induction of CYP1A1 mRNA was determined in hepatic tissue following a single i.p. injection of 10 mg/kg AHRL1. In FIG. 14b, liver tissue was harvested and processed for mRNA analysis. CYP1A1 gene expression was determined relative to the β-actin gene, and the fold-induction was determined by the ΔΔCt method using the vehicle treated samples as a control. The mean values are shown with SEM for 2-3 mice per time point.

FIG. 13b shows CYP1A1 was induced 2-fold at 4 hours and up to 7-fold by 20 hours. Induction was no longer apparent at 48 hours (data not shown). The data indicates that although the serum half-life of AHRL1 is relatively short, the extended induction profile of CYP1A1 mRNA suggests that there is tissue retention of the AHRL1 compound and that a once per day dosage regimen is sufficient to sustain AhR activation. Thus, AHRL1 has more favorable pharmacokinetics properties which suggests a lower toxicity compared to other AhR ligands. With a short half-life and no acute toxicity at the dose required for a therapeutic effect, the pharmacokinetic data suggests AHRL1 is a safer treatment approach than previous therapeutic approaches to immune-mediated disease.

FIGS. 14a-14i show AHRL1 induces an AhR-dependent Treg phenotype by a mechanism that is mediated by the AhR in donor CD4+ T cells. The AhR-induced Tregs were identified as the CD4+CD25+CTLA-4+CD62L$^{low}$ population of T cells. To determine if AHRL1 induced changes in donor CD4+ T cells, AHRL1 was compared with TCDD and the vehicle. On day 0, B6D2F1 host mice in groups of 5 were injected with CFSE-labeled C57BL/6 (H-2$^{b/b}$) T cells and given 15 mg/kg of AHRL1, 15 μg/kg of TCDD, or vehicle by i.p. injection. At 24 hours, an additional dose of 7 mg/kg of AHRL1 or vehicle was given. Mice that were treated with TCDD at the time of donor cell transfer were used as positive controls. Splenocytes were isolated on day 2 for phenotypic analysis of the alloresponsive (CFSE-diluted) donor CD4+ T cells. Splenocytes were harvested from the host mice and the CD4+ T cells were identified by flow cytometry.

Figure 14A:
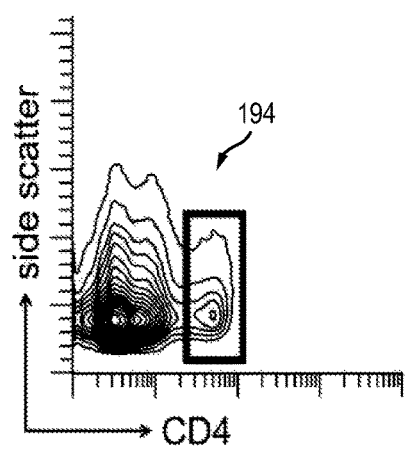
FIGS. 14a-14i illustrate results that AHRL1 induces an AhR dependent regulatory T cell phenotype during GVHD.
Figure 14B:
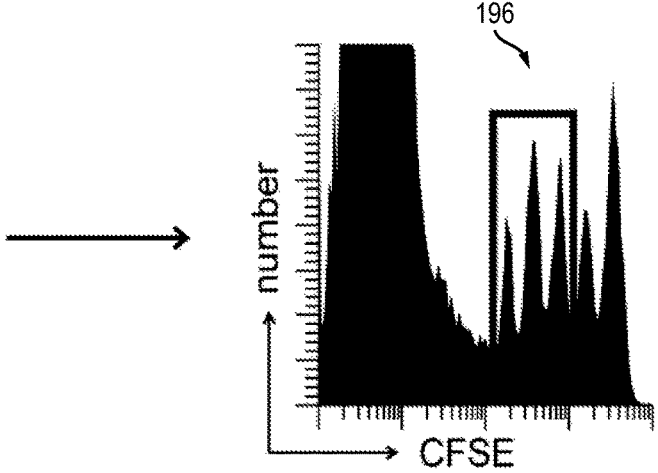

FIG. 14a shows donor CFSE+ cells were gated on CD4+ T cells, indicated by rectangular region 194. The alloactivated population was identified by CFSE dilution, indicated by rectangular region 196 in the histogram of FIG. 14b. The CFSE negative population represent host CD4+ cells.

Figure 14C:
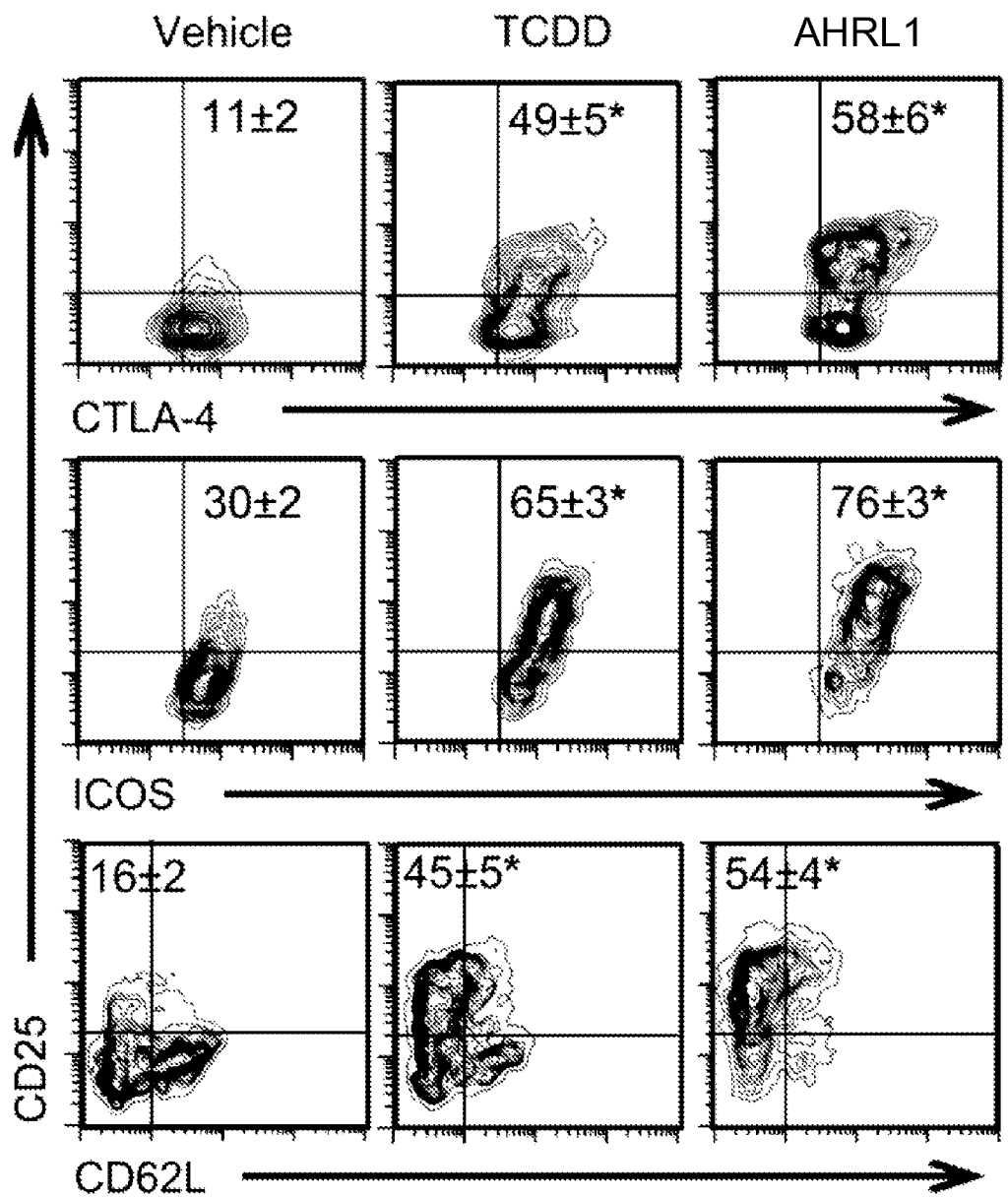

FIG. 14c shows that compared with vehicle treatment, AHRL1 significantly increased the percentage of donor CD4+ T cells that co-expressed CD25 and CTLA-4, along with low expression of CD62L. Expression of inducible T-cell co-stimulator (ICOS or CD278), which is another marker associated with Tregs, was also significantly increased by treatment with AHRL1, as well as TCDD. Histograms reveal the Treg phenotype based on co-expression of CD25 with CTLA-4, ICOS and down-regulated CD62L (CD62L$^{lo}$) on alloactivated CD4+ donor T cells from each treatment group. Treatment mean±SEM is shown in the quadrant of interest. Therefore, daily treatment with AHRL1 induced the Treg phenotype as effectively as the immunosuppressive dose of TCDD (15 µg/kg).

FIG. 14c shows the total number of alloactivated CD4+ CD25+ T cells co-expressing CTLA-4+, ICOS, and low levels of CD62L was increased by treatment with both AhR ligands: AHRL1 and TCDD.

Figure 14D:
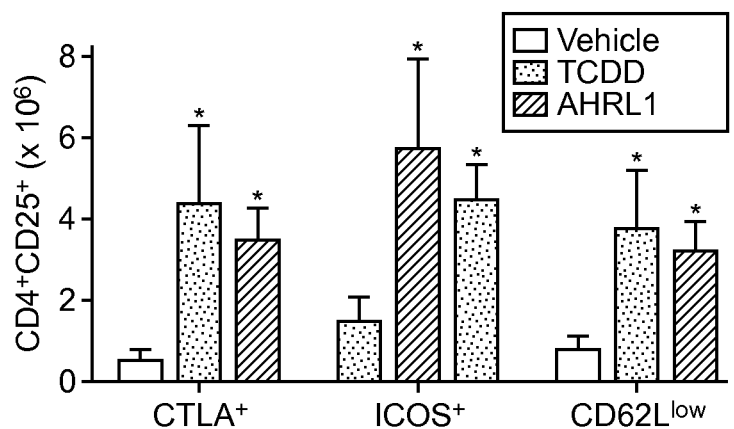

FIG. 14d shows AhR-dependent induction of the donor Treg phenotype by AHRL1. On day 0, B6D2F1 host mice in groups of 5 were injected with donor T cells obtained from AhR$^{+/+}$ or AhR-deficient (AhR$^{-/-}$) C57BL/6 mice. Host mice were treated with 2 mg/kg of AHRL1 or vehicle immediately following donor cell transfer and again at 24 hours. Treg phenotype analyzed on day 2 was significantly increased by AHRL1 treatment when AhR$^{+/+}$ donor T cells were injected but not when AhR$^{-/-}$ donor T cells were used. The results show that AHRL1 does not induce the Treg phenotype when donor T cells were obtained from AhR-deficient mice, demonstrating that the induction of the Treg phenotype by AHRL1 was mediated via the AhR in the donor T cells. Thus, the AhR in the CD4+ T cell is the primary target driving the AhR-Treg phenotype.

Figure 14E:
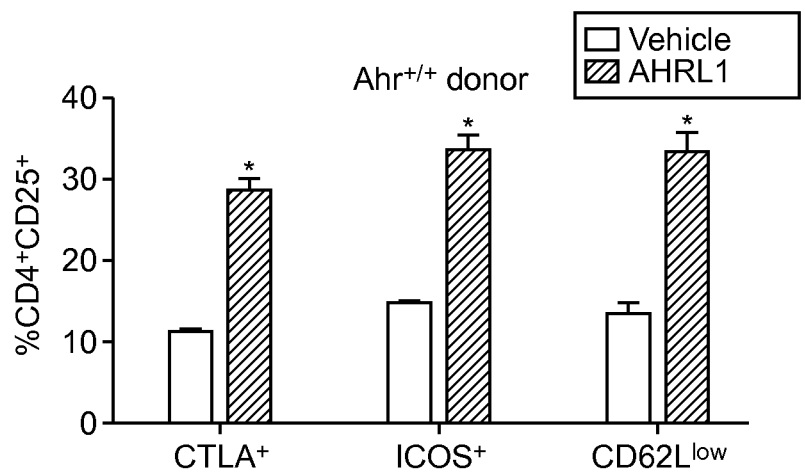

FIG. 14e shows induction of the Treg phenotype increased with increasing dose of AHRL1. On day 0, B6D2F1 host mice in groups of 3-5 were injected with C57BL/6 T cells. Mice were immediately treated with 0 mg/kg, 0.4 mg/kg, 2 mg/kg, or 10 mg/kg of AHRL1 and again on day 1. On day 2, expression of markers associated with the AhR-Treg phenotype increased as the dose of AHRL1 increased. Further, dosing generally correlated with degree of activation of AhR as reflected by CYP1A1, CYP1B1, and AHRR expression in lymph nodes from the same mice. The asterisk (*) indicates a p-value of 0.05 relative to vehicle treatment.

Figure 14F:
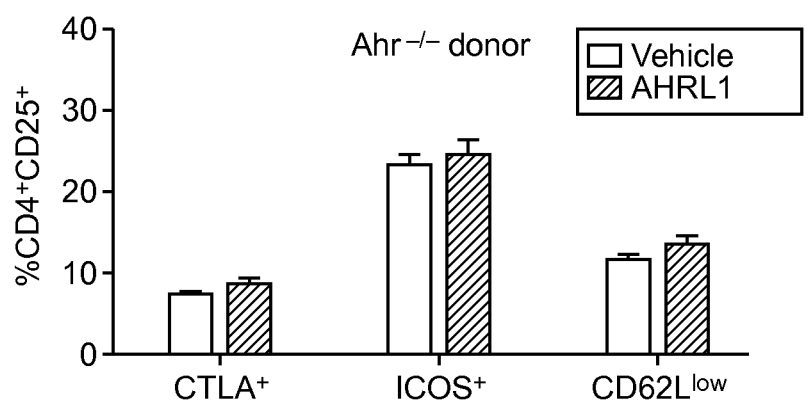
Figure 14G:
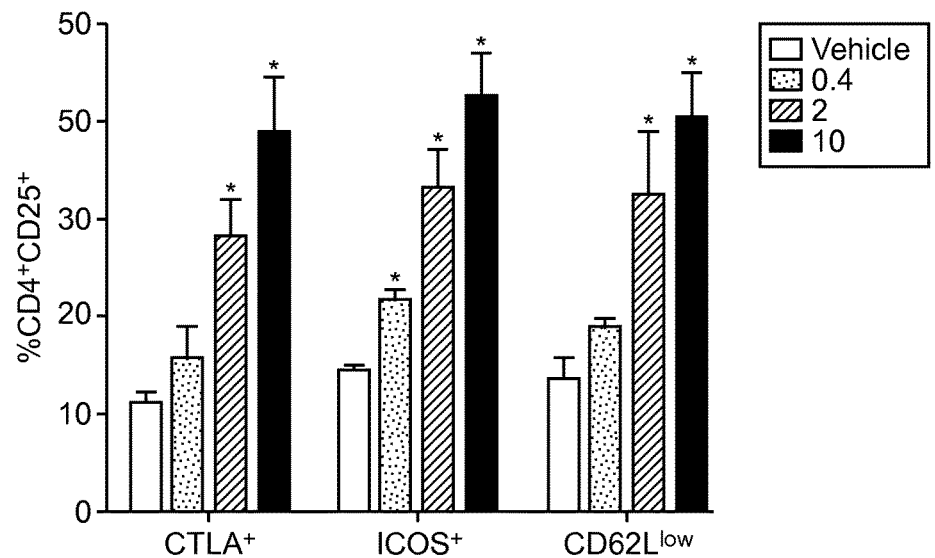
Figure 14H:
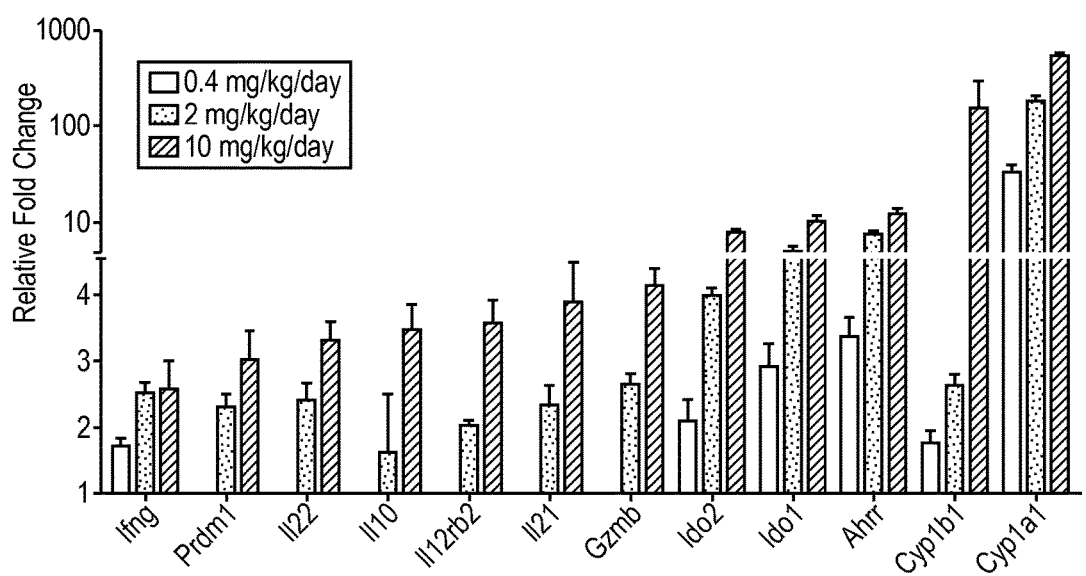

FIG. 14f shows changes in gene expression after treatment with AHRL1. In the same mice as discussed with respect to FIG. 14e, lymph nodes were harvested and analyzed for expression of genes that also increase with treatment with TCDD, an AhR ligand that induces AhR-Tregs. Results show a similar profile of gene expression that is induced by treatment with AHRL1 as with TCDD. Changes in gene expression were calculated relative to the β-actin gene, and the fold-induction was calculated by the ΔΔCt method using the vehicle treated samples as a control.

Expression of several other genes, in addition to CYP1A1, CYP1B1, and AHRR, that are up-regulated in lymph node cells (host- and donor-derived) by TCDD, another AhR ligand, were also induced by AHRL1, including Il10, Il21, Il22, Il12rb2, Gzmb, Ido1 and Ido2. The dose of 2.0 mg/kg/day of AHRL1 was the minimum effective dose as 0.4 mg/kg/day did not induce significant changes in most of the parameters associated with AhR-Tregs. AHRL1 did not induce expression of Foxp3 at any dose, and thus, Foxp3 does not appear to be a direct, AhR-inducible target gene in activated T cells in vivo. The increase in Foxp3+ cells demonstrated using the NOD mice models is likely caused indirectly, as a consequence of downstream effects of AhR activation (e.g., fewer effector T cells, induction of tolerogenic DC, etc.). AhR-Tregs are induced by direct activation of AhR in donor CD4+ T cells and differ from the Foxp3+ Tregs that are induced indirectly via AhR signaling in dendritic cells. Both types of Tregs may contribute to the suppression of autoimmune and allergic diseases. The ability of AhR ligands to directly induce antigen-specific Tregs via AhR activation in antigen-responsive CD4+ T cells bypasses many of the barriers associated with current approaches used to enhance Treg function that rely on infusion of ex vivo expanded cells.

Figure 14I:
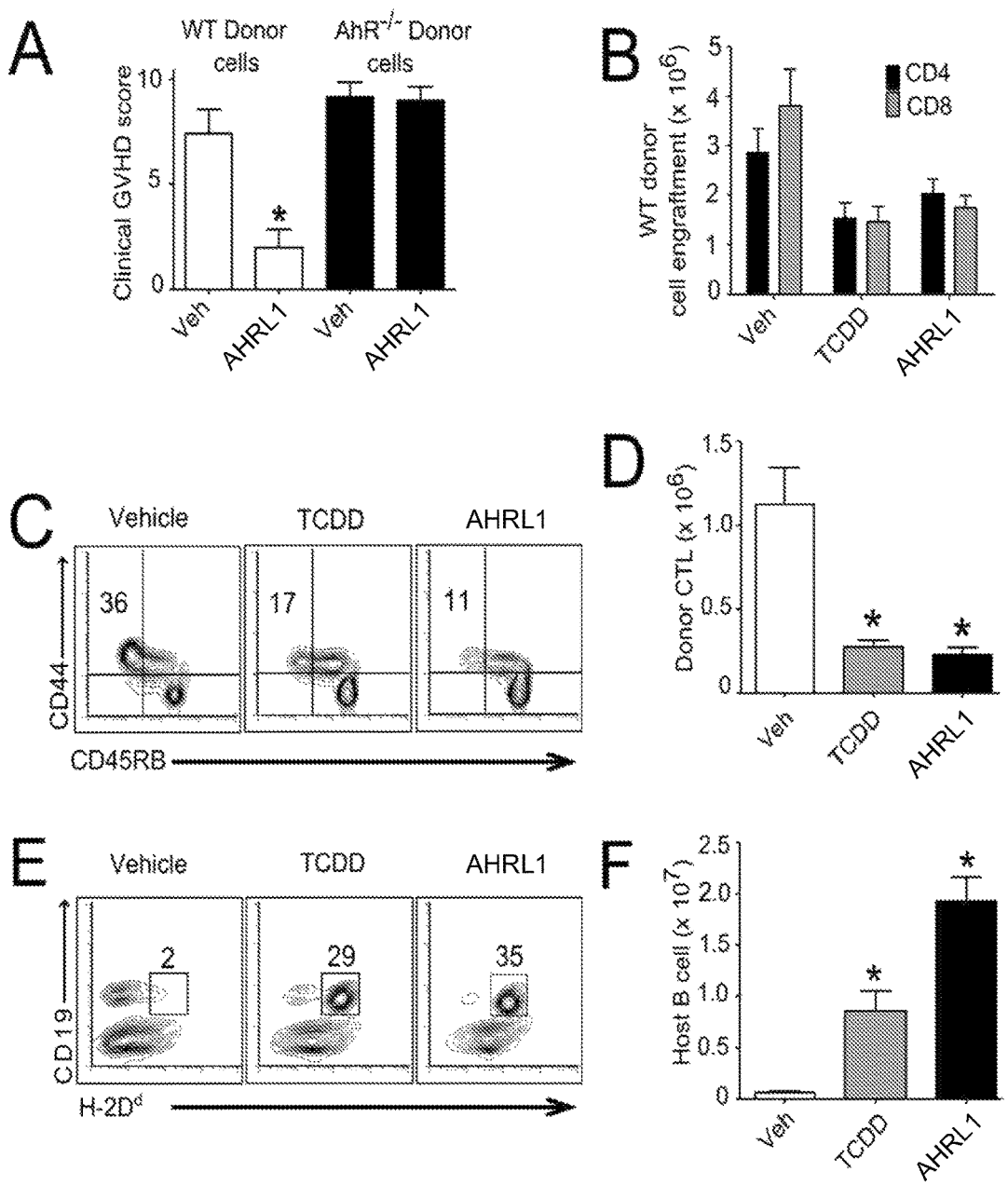

FIG. 14i shows results that indicate AHRL1 suppresses GVHD in an AhR-dependent manner. The results shown in FIGS. 14a-14h show that AHRL1 induces AhR-Tregs. FIG. 14i shows results of a study determining that AHRL1 suppresses GVHD and that AHRL1 suppression of GVHD is dependent on AhR expression in the donor cells. GVHD was established using donor cells obtained from wild type or AhR-deficient mice. B6D2F1 host mice were injected with wild type (WT) or AhR$^{-/-}$ splenocytes to initiate the graft versus host (GVH) response. Due to a limited number of AhR-deficient mice available, whole splenocytes rather than purified T cells were used to initiate the GVH response. Host mice were given AHRL1 or vehicle treatments daily for 15 days. The vehicle consisted of a mixture of 6.7% anisole and peanut oil. A single loading dose of 10 mg/kg AHRL1 was given at the time of donor cell injection and a maintenance dose of 2 mg/kg AHRL1 was given every day thereafter until termination of the experiment on day 15.

The progression of GVHD in the host mice was monitored and a clinical GVHD pathology score was calculated. At termination of the 15-day study, each animal was evaluated and given a clinical GVHD pathology score based on five criteria: changes in weight, posture, activity, fur texture, and mortality. The clinical GVHD pathology score was assessed on a scale of 0 to 3, where 0 was normal, 1 was moderate morbidity, 2 was severe morbidity, and 3 was death. Graph A in FIG. 14i shows that GVHD pathology was significantly reduced by treatment with AHRL1 in mice that received AhR-wild type donor cells whereas the pathology score was not affected by AHRL1 in mice that received AhR-deficient donor cells. Thus, GVHD was suppressed by AHRL1 if the donor cells expressed AhR.

In a separate study, the effect of AHRL1 on donor cell engraftment was examined and directly compared with the effect of TCDD. B6D2F1 host mice in groups of 6 were injected with splenocytes from C57Bl/6 mice to initiate the GVH response, and treated with AHRL1 or vehicle daily for 15 days. The vehicle consisted of a mixture of 6.7% anisole and peanut oil. A single loading dose of 10 mg/kg AHRL1 was given at the time of donor cell injection and a maintenance dose of 2 mg/kg AHRL1 was given every day thereafter until termination of the experiment on day 15. 15 µg/kg of TCDD was given to an additional group of 6 mice on day 0 as a positive control. Graph B in FIG. 14i shows that GVHD is suppressed by AHRL1 and TCDD as evidenced by the reduced total number of donor CD4+ and CD8+ T cells engrafted in the host spleen at day 15. Graphs C and D in FIG. 14i show that AHRL1 and TCDD reduce the percentage and number of activated donor CD8+ T cells expressing a CTL phenotype (CD8+CD44$^{hi}$CD45RB$^{low}$) in the spleen of host mice. The reduction in CTL was reflected in the higher percentage and number of host B cells remaining in the spleen compared with those in the vehicle treated mice. Graphs E and F in FIG. 14i show an increased percentage and number of host B cells (CD19+ cells) in the spleen at day 15. The donor cells were identified in the host spleen as the H-2D$^d$ negative population. The efficacy of daily treatment with AHRL1 in suppressing GVHD was equivalent to the single dose of TCDD given on day 0. The results discussed with respect to FIG. 14i are statistically significant, with a p-value of 0.05, as compared to the vehicle control.

FIGS. 15a-15e show the chemical structure of examples of several 11-Cl-BBQ analogs. Table 2 shows the chemical names of the example analogs of 11-Cl-BBQ.

TABLE 2

| Analog Reference Number | Analog Name |
| --- | --- |
| analog 1 (BBQ) | 7H-Benzimidazo[2,1-a]benzo[de]isoquinolin-7-one |
| analog 2 | 2-Amino-10-chlorobenzimidazo[2,1-b]benzo[lmn][3,8]phenanthroline-1,3,6(2H)-trione |
| analog 3 | 11-Chloro-8H-benzimidazo[2,1-a]phenanthro[3,4,5-defg]isoquinolin-8-one |
| analog 4 | 4,11-Dichloro-7H-benzimidazo[2,1-a]benzo[de]isoquinolin-7-one |
| analog 5 (STO-609) | 7-Oxo-7H-benzimidazo[2,1-a]benzo[de]isoquinoline-3-carboxylic acid |
| analog 6 | 11-Trifluoro-7H-Benzimidazo[2,1-a]benzo[de]isoquinolin-7-one |
| analog 7 | 10-Chloro-7H-Benzimidazo[2,1-a]benzo[de]isoquinolin-7-one |

Figure 15B:
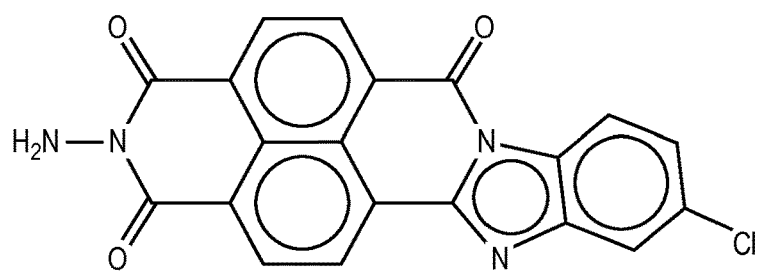
Figure 15C:
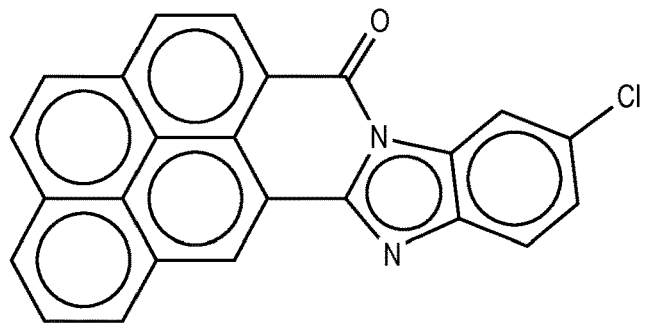
Figure 15D:
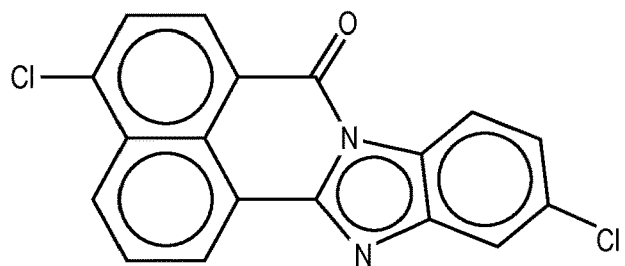
Figure 15E:
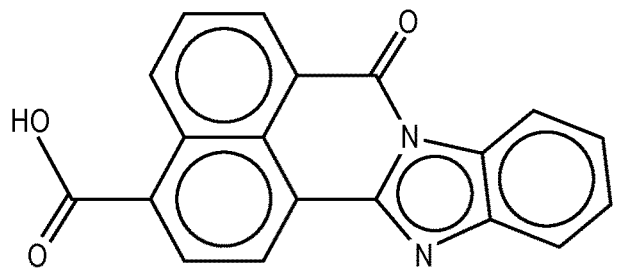

FIG. 15a shows analog 1 from Table 2. Analog 1 includes the unsubstituted BBQ molecule. In comparison to analog 1 (BBQ), the addition of one or two chlorine atoms increases the potency of the BBQ molecule to bind AhR and induce Tregs. FIG. 15b shows analog 2 from Table 2. FIG. 15c shows analog 3 from Table 2. FIG. 15d shows analog 4 (4,11-diCl-BBQ) from Table 2. FIG. 5e shows analog 5 (STO-609) from Table 2. Analog 5 (STO-609) is a carboxylic acid-substituted BBQ that is used experimentally to inhibit $Ca^{2+}$/calmodulin-dependent protein kinase kinase (CaMKK) activity. Analogs 6 and 7 represent alternative fluoro and chloro BBQ substitutions, respectively.

Figure 16A:
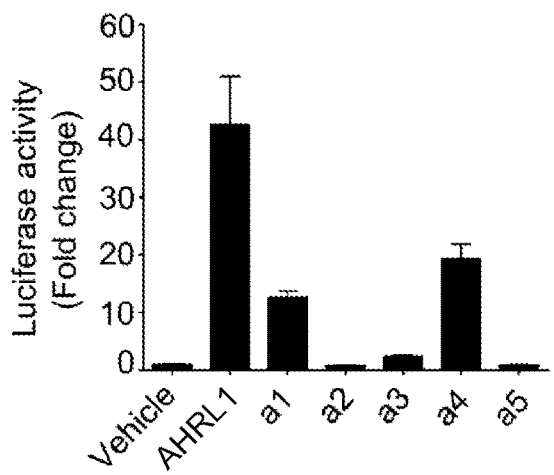
FIGS. 16a-16d show results of activity studies for analogs 1-5 compared to vehicle and AHRL1.

FIGS. 16a-16d show results of activity studies for analogs 1-5, vehicle, and AHRL1. The analogs 1-5 were tested at 10 nM for each analog's ability to induce the AhR-regulated reporter gene activity. Hepa-1 cells expressing endogenous AhR were transfected with a XRE-luciferase reporter gene. A sample size of n=3 of the transfected cells were treated for 12 hours with 10 nM of each compound: vehicle, AHRL1, and analogs 1-5. The mean luciferase activity is shown with SEM. FIG. 16a shows that analog 1 (a1) BBQ and analog 4 (a4) 4,11-diCl-BBQ induced 13- and 19-fold activation of AhR, respectively, while analog 3 (a) induced 2-fold increase. Analog 2 (a2) and analog 5 (a5) (STO-609) did not induce reporter activity at the 10 nM concentration tested. However, other evidence shows that analog 5 alters T cell effector and regulatory functions through other pathways and at a higher dose than 10 nM. FIG. 16a illustrates BBQ, and other analogs of 11-Cl-BBQ activate AhR, indicating BBQ, and other analogs of 11-Cl-BBQ will induce Tregs and alter T cell differentiation to suppress CTL production.

Figure 16B:
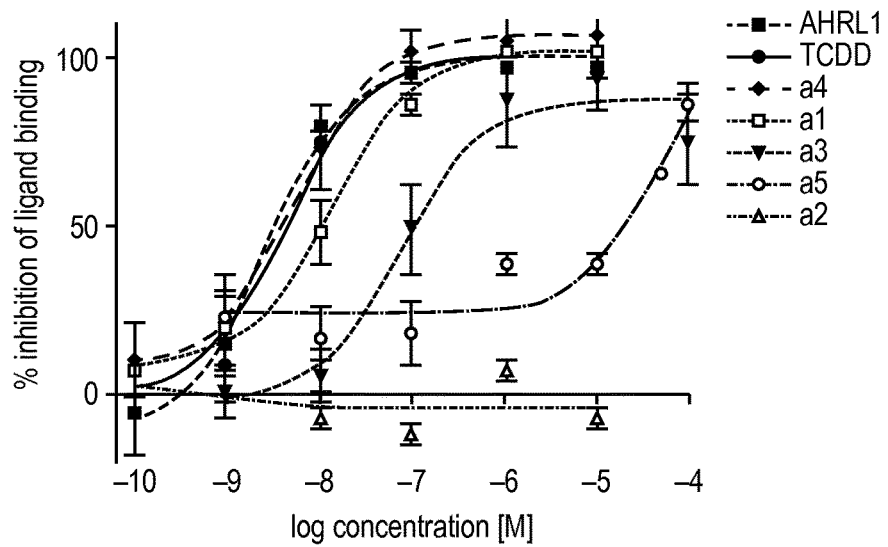

FIG. 16b shows dose response curves for the competitive inhibition of [$^3$H] 3-MC binding to AhR. The ligand binding affinity of each analog was determined by the analog's ability to competitively inhibit the binding of [$^3$H] 3-methylcholanthrene (3-MC) to AhR. The concentration that inhibited binding by 50% (IC50) was calculated from the dose-response curves for each analog and compared to the IC50 of 4.7 nM for TCDD. The IC50s of AHRL1 and analog 4 (4,11-diCl-BBQ) were similar to TCDD at 2.6 and 5.2 nM while the affinity of analog 1 (BBQ) was lower at 13.7 nM. The IC50 of analog 3 was 10-fold lower (77.3 nM), and analog 5 (STO-609) was 1000-fold less active than TCDD at 45.2 µM. Analog 2 was inactive over the concentration range tested.

Figure 16C:
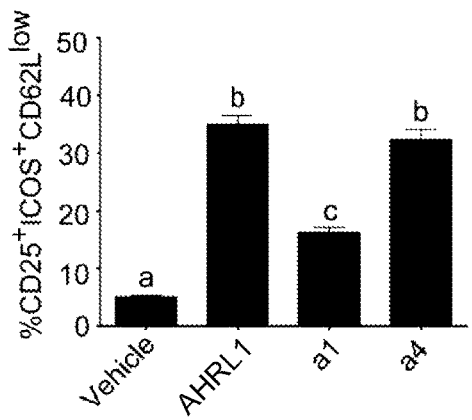
Figure 16D:
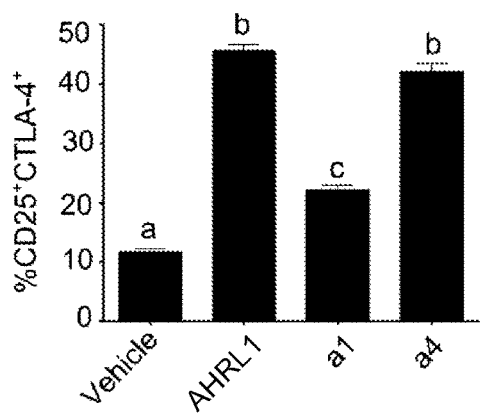

FIGS. 16c and 16d show expression of phenotypic markers, CD25+ICOS+CD62L$^{low}$ and CD25+CTLA-4+, associated with AhR-Tregs in mice treated with AHRL1. Host mice were treated with 10 mg/kg of AHRL1, 11-Cl-BBQ analog, or vehicle on day 0 and day 1 following donor cell transfer. On day 2, the alloactivated CD4+ donor T cells were identified based on CFSE dilution. The percentage of donor cells in each group expressing the Treg markers were derived from flow histograms. The data represents mean±SEM of 5 mice per treatment. FIG. 16c shows expression of the phenotypic marker CD25+ICOS+CD62L$^{low}$. AHRL1, analog 1, and analog 4 are statistically different from vehicle (p-value=0.05) in terms of expression of CD25+ICOS+CD62L$^{low}$. Analog 1 is statistically different from AHRL1 and analog 4 (p-value=0.05). FIG. 16d shows expression of phenotypic marker, CD25+CTLA-4+. AHRL1, analog 1, and analog 4 are statistically different from vehicle (p-value=0.05) in terms of expression of CD25+CTLA-4+. Analog 1 is statistically different from AHRL1 and analog 4 (p-value=0.05). Therefore, analog 1, and analog 4 are shown to be AhR ligands that are capable of inducing Tregs in vivo. Accordingly, analogs 1 and 4 are expected to have a similar therapeutic effect in a subject as AHRL1 by suppressing an autoimmune response. Additionally, analog 6, analog 7, and other analogs of 11-Cl-BBQ, that are found to be active AhR ligands using the disclosed screening method, are expected to induce Tregs and suppress CTL to provide treatment and/or prevention of immune-mediated diseases.

Figure 17A:
FIGS. 17a-17c illustrate results of study in AHRL1 treatment of T1DM in NOD mice.
Figure 17B:
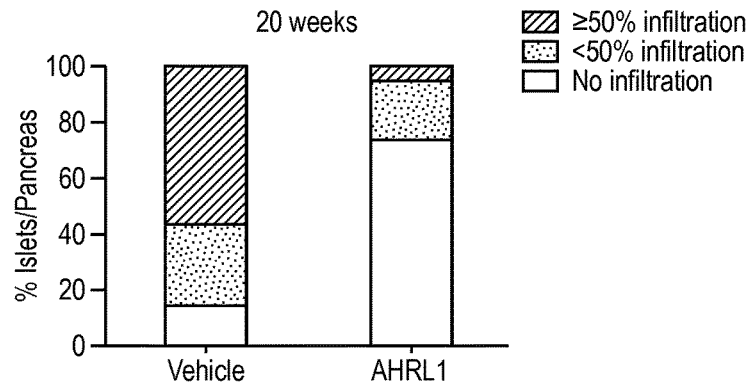
Figure 17C:
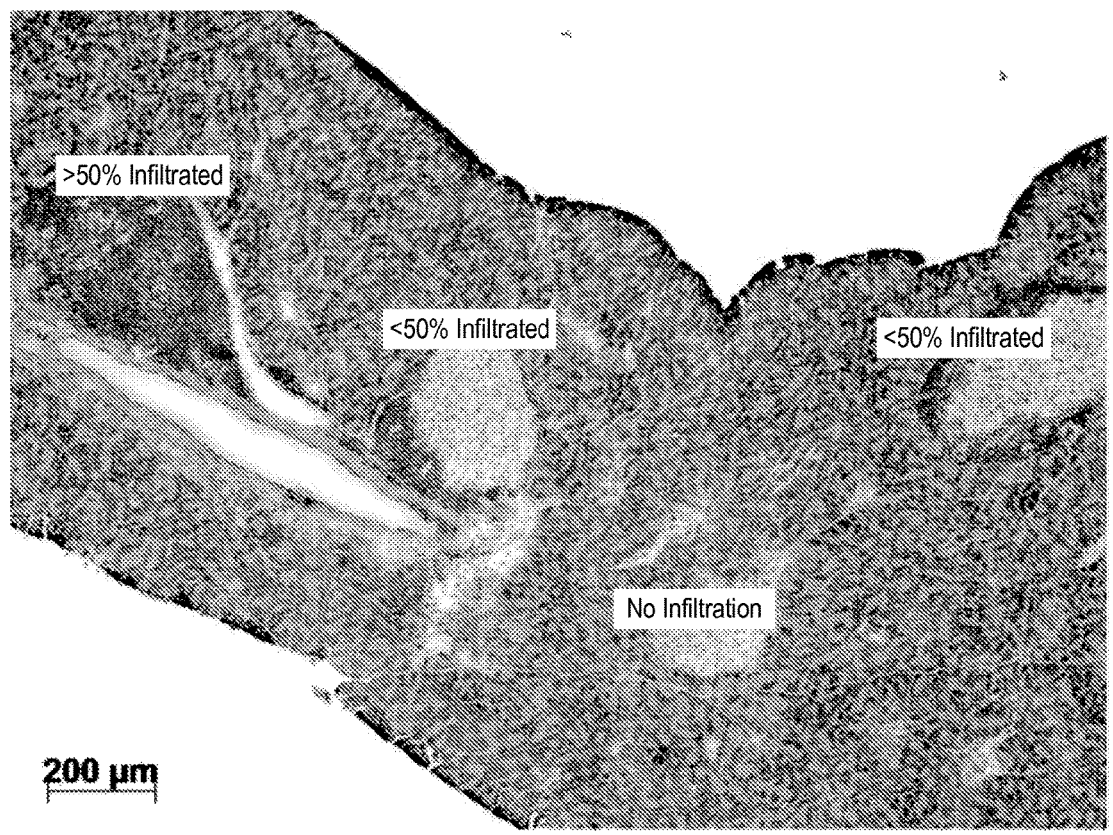

FIGS. 17a-17c show that oral treatment of NOD mice with AHRL1 is highly effective in suppressing pancreatic insulitis, the pathogenic mechanism underlying the development of type-1 diabetes. NOD mice develop diabetes due to a breakdown in self-tolerance to several antigens expressed on pancreatic islet cells and the infiltration of the pancreas by self-reactive T cells. Overt diabetes develops in parallel with an age-related decline in the number and function of CD4+CD25+FoxP3+ Tregs. Prevention of progressive insulitis and β-cell destruction in NOD mice has been shown to depend on the maintenance or expansion of a population of CD4+CD25+FoxP3+ Tregs that suppress the activation and effector functions of pathogenic T cells.

FIG. 17a shows the results of AHRL1 treatment in NOD mice at 12 weeks of age. FIG. 17b shows the results of AHRL1 treatment in NOD mice at 20 weeks of age. NOD mice were treated with 60 mg/kg of AHRL1 or vehicle by oral gavage, three times per week, starting at 7 weeks of age. At 12 or 20 weeks of age, mice were sacrificed and pancreata were collected and processed for histological examination. Pancreas sections were scored for islet infiltration by inflammatory cells. Islet infiltrations were scored according to the histology example in FIG. 17c. FIG. 17c shows an example of pancreas histology from an NOD mouse showing different degrees of islet infiltration. At both 12 weeks (FIG. 17a) and 20 weeks (FIG. 17b), there was a statistically significant treatment effect with AHRL1 treatment compared to vehicle treatment based on chi-squared test for trend. A sample size of n=7-9 mice per group was used with a minimum of 50 islets counted per mouse. The results in FIGS. 17a and 17b show that treatment of NOD mice with 60 mg/kg three times per week of AHRL1 protects from the development of pancreatic insulitis. The results show that oral treatment of mice with AHRL1 suppresses T1DM even when given after the pancreas has been infiltrated with inflammatory CTL cells implying that clinical use of AHRL1 during the "honeymoon period," notable in many new onset T1DM patients, will be effective at preventing T1DM progression.

Based on the 60 mg/kg oral dose shown herein to be effective in mice, a human equivalent dose (HED) is expected to be approximately 4.3 mg/kg. The HED is calculated based on equation (1).

$$HED = D_{animal} \times \left(\frac{W_{animal}}{W_{human}}\right)^{(1-b)} \quad (1)$$

where: $D_{animal}$=animal dose in mg/kg
$W_{animal}$=animal reference body weight in kg
$W_{human}$=human reference body weight in kg
b=allometric exponent Following industry standards, a reference body weight of 0.02 kg was used for $W_{animal}$ based on a working weight range of 0.011 to 0.034 kg for a mouse. A reference body weight of 60 kg was used for $W_{human}$. A normalization b was selected as 0.67 based on conventional conversions. Depending upon the route of administration, greater doses of the AhR ligand, e.g., AHRL1, 11-Cl-BBQ, 10-Cl-BBQ, an 11-Cl-BBQ analog, or combination thereof, may be administered. For example, significantly lesser amounts of 11-Cl-BBQ may be absorbed when the route of administration is oral as compared to parenteral or other forms of systemic administration.

Routes of administration of the compound AHRL1, 11-Cl-BBQ, 10-Cl-BBq, an 11-Cl-BBQ analog, or combination thereof include oral and parenteral routes, such as intravenous, subcutaneous, intraperitoneal, intramuscular, and intraarterial injection, as well as inhalation, topical, transdermal, nanoparticle, and other suitable delivery methods. Nanoparticles include structures having at least one dimension of less than 100 nm. Nanoparticles may include lipids, liposomes, polymers, dendrimers, silicon materials, carbon materials, magnetic materials, or other nanoparticle delivery systems. A physiologically or pharmaceutically acceptable carrier or vehicle is selected according to the mode of administration. Examples of pharmaceutically acceptable carriers include saline, phosphate buffered saline (PBS), water, aqueous ethanol, emulsions such as oil/water emulsions, triglyceride emulsions, wetting agents, tablets, and capsules. Oral treatment of T1DM-prone mice with AHRL1 thereof prevents the underlying pathogenic process of islet cell destruction in an oral dosing regimen that does not induce toxicity. AHRL1 appears to induce its own metabolism such that chronic use may require dose and therapeutic regimen adjustments. In one embodiment, AHRL1, 11-Cl-BBQ, 10-Cl-BBQ, an 11-Cl-BBQ analog, or combination thereof is delivered orally together with a pharmaceutically acceptable carrier. Orally available AHRL1, 11-Cl-BBQ, 10-Cl-BBQ, an 11-Cl-BBQ analog, or combination thereof may prevent T1DM progression. The route of administration is expected to be oral at a daily dose. In another embodiment, AHRL1, 11-Cl-BBQ, 10-Cl-BBQ, an 11-Cl-BBQ analog, or combination thereof is administered topically, transdermally, or parenterally.

FIGS. 18a-18r show the clinical chemistry profile from a toxicology screen for three groups: AHRL1 treated mice, vehicle treated mice, and untreated mice. For the test group, the mice were treated with AHRL1. The vehicle given was the carrier for the AHRL1 compound. The carrier included 30% DMSO, 20% Cremaphor, and 50% Peceol. The mice were tested after 12 weeks of exposure. The clinical chemistry panel includes tests for substances in the blood that have biological functions, metabolites or waste products, and substances that indicate cell damage or disease. FIG. 18a shows the chemistry profile for BUN in the three groups. FIG. 18b shows the chemistry profile for creatinine in the three groups. FIG. 18c shows the chemistry profile for glucose in the three groups. FIG. 18d shows the chemistry profile for cholesterol in the three groups. FIG. 18e shows the chemistry profile for total protein in the three groups. FIG. 18f shows the chemistry profile for albumin in the three groups. FIG. 18g shows the chemistry profile for total bilirubin in the three groups. FIG. 18h shows the chemistry profile for CK in the three groups. FIG. 18i shows the chemistry profile for alkaline phosphatase in the three groups. FIG. 18j shows the chemistry profile for GGT in the three groups. FIG. 18k shows the chemistry profile for ALT in the three groups. FIG. 18l shows the chemistry profile for sodium in the three groups. FIG. 18m shows the chemistry profile for potassium in the three groups. FIG. 18n shows the chemistry profile for chloride in the three groups. FIG. 18o shows the chemistry profile for calcium in the three groups. FIG. 18p shows the chemistry profile for phosphorus in the three groups. FIG. 18q shows the chemistry profile for carbon dioxide in the three groups. FIG. 18r shows the anion gap measurement in the three groups. The results in FIGS. 18a-18r and in Table 1 show no change or statistical difference in clinical chemistry parameters for AHRL1 treated mice as compared with vehicle treated mice.

In summary, AHRL1 is a high-affinity ligand and potent activator of the AhR. Activating AhR blocks the differentiation of effector CTL resulting in suppression of autoimmune destruction of pancreatic β-cells. Treatment with AHRL1 prevents the autoimmune destruction of β-cells without inducing global immune suppression associated with many current therapies. AHRL1 is rapidly metabolized, with a half-life of approximately 2 hours, which is a favorable pharmacokinetic property. Rapid metabolism of AHRL1 is expected to have reduced toxicity compared to other AhR ligands, e.g., TCDD. Despite the relatively short half-life of AHRL1, the extended induction profile of CYP1A1 mRNA suggests that there is tissue retention of AHRL1 and that a once-a-day dosage regimen is sufficient to sustain AhR activation.

The induction of Tregs in vivo by treatment with AhR ligands represents a therapeutic approach for treatment of immune-mediated diseases. AhR-Tregs can be induced by targeting the AhR directly in CD4+ T cells, or indirectly via AhR activation in tolerogenic dendritic cells. The data disclosed herein show that AHRL1 directly targets CD4+ T cells to induce AhR-dependent Tregs while simultaneously suppressing murine GVHD and T1DM without overt toxicity. Together with historical and structure-activity data, the disclosed results provide support for further clinical development of the BBQ class of compounds for use in AhR-based therapy. The activation of AhR by AHRL1, 11-Cl-BBQ, 10-Cl-BBQ, 11-Cl-BBQ analogs, and combinations thereof indicates AHRL1, 11-Cl-BBQ, 10-Cl-BBQ, an 11-Cl-BBQ analog, or combinations thereof can be administered to treat autoimmune disease.

Diagnosis and genetic counseling provides patients with the opportunity to discover T1DM in the early stages of the disease. Treatment with AHRL1 or analogs thereof will prevent development of T1DM and provide patients with the opportunity to avoid dependence on insulin therapy and the numerous disease complications. Blocking CTL differentiation by inducing AhR-Tregs and/or suppressing differentiation of CTL cells with AHRL1, 11-Cl-BBQ, 10-Cl-BBQ, an 11-Cl-BBQ analog, or combinations thereof can also suppress other autoimmune diseases with similar Treg compartments as T1DM, such as GVHD, Celiac disease, autoimmune hepatitis, autoimmune pancreatitis, Crohn's disease, interstitial cystitis, microscopic colitis, and ulcerative colitis. Topical administration could treat T cell mediated autoimmune diseases of the skin including alopecia areata, atopic dermatitis, cicatricial pemphigoid, dermatomyositis, dermatitis herpetiformis, lichen planus, pemphigus vulgaris, and psoriasis.

The present invention demonstrates the therapeutic efficacy of AHRL1 in treating autoimmune disease. For example, AHRL1 can be administered in a repeated dosing scheme to maintain AhR activation over time, without cytotoxicity. The similar activation of AhR by 11-Cl-BBQ, 10-Cl-BBQ, and analogs of 11-Cl-BBQ indicates 11-Cl-BBQ, 10-Cl-BBQ, and analogs of 11-Cl-BBQ can also be administered in a repeated dosing scheme to maintain AhR activation over time, without cytotoxicity. AHRL1 replicates the efficacy of TCDD, is rapidly metabolized compound, and with a proper dosing schedule ensures continued activation of AhR. The strong suppression of islet infiltration in AHRL1 treated mice demonstrates the therapeutic potential of AHRL1, 11-Cl-BBQ, 10-Cl-BBQ, an 11-Cl-BBQ analog, or combinations thereof to prevent and treat T1DM.

The present invention demonstrates chronic treatment with AHRL1 resulted in an almost complete prevention of the development of insulitis in NOD mice. The almost complete prevention of the development of insulitis in NOD mice by AHRL1 indicates treatment during the early stages of T1DM with AHRL1, 11-Cl-BBQ, 10-Cl-BBQ, an analog of 11-Cl-BBQ, or combinations thereof will prevent the autoimmune destruction of pancreatic β-cells and consequently prevent the progression and development of T1DM. Similarly, treatment of an individual after a tissue transplant with AHRL1, 11-Cl-BBQ, 10-Cl-BBQ, an analog of 11-Cl-BBQ, or combinations thereof will suppress GVHD.

Furthermore, the results of tests on NOD.Foxp3D$^{DTR}$ mice illustrate that AhR ligands suppress insulitis in the absence of Foxp3+ Tregs and that inhibition of T cell differentiation into CTL does not necessarily rely on induction of Foxp3+ Tregs. The ability of AHRL1 and TCDD to suppress insulitis in the absence of Foxp3+ Tregs directly challenges the widely supported proposition that induction of Foxp3+ Tregs is the primary mechanism by which AhR ligands mediate suppression of immune-mediated diseases. The ability of AHRL1 to suppress insulitis indicates AhR ligands, e.g., TCDD, 11-Cl-BBQ, 10-Cl-BBQ, an 11-Cl-BBQ analog, or combination thereof may be used to treat a subject having an autoimmune or other immune-mediated disease characterized by increased pathogenic CTL cell populations and/or absence of functional Foxp3+ Treg cells.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method of treating an autoimmune disease treatable through induction of regulatory T-cells comprising administering a therapeutically effective amount of an aryl hydrocarbon receptor (AhR) ligand to a subject in need thereof, wherein the aryl hydrocarbon receptor (AhR) ligand is 11-chloro-7H-benzimidazo[2,1-a]benzo[de]Iso-quinolin-7-one (11-Cl-BBQ), 7H-benzimidazo[2,1-a]benzo[de]isoquinolin-7-one, 4,11-dichloro-7H-benzimidazo[2,1-a]benzo[de]isoquinolin-7-one, 7-oxo-7H-benzimidazo[2,1-a]benzo[de]-isoquinoline-3-carboxylic acid, 11-trifluoro-7H-benzimidazo[2,1-a]benzo[de]isoquinolin-7-one, or 10-chloro-7H-benzimidazo[2,1-a]benzo[de]isoquinolin-7-one.

2. The method of claim 1, wherein the autoimmune disease is diabetes mellitus type 1.

3. The method of claim 1, wherein the autoimmune disease is graft versus host disease.

4. The method of claim 1, wherein the autoimmune disease is Celiac disease, autoimmune hepatitis, autoimmune pancreatitis, Crohn's disease, interstitial cystitis, microscopic colitis, or ulcerative colitis.

5. The method of claim 1, wherein the autoimmune disease is alopecia areata, atopic dermatitis, cicatricial pemphigoid, dermatomyositis, dermatitis herpetiformis, lichen planus, pemphigus vulgaris, or psoriasis.

6. The method of claim 1, wherein the aryl hydrocarbon receptor (AhR) ligand is administered topically.

7. The method of claim 1, wherein the aryl hydrocarbon receptor (AhR) ligand is administered orally, transdermally, intravenously, subcutaneously, or with a nanoparticle.

8. The method of claim 1, wherein the aryl hydrocarbon receptor (AhR) ligand is 11-chloro-7H-benzimidazo[2,1-a]benzo[de]Iso-quinolin-7-one (11-Cl-BBQ).

9. The method of claim 1, further including administering the AhR ligand with a pharmaceutically acceptable carrier.

* * * * *